United States Patent

Naylor-Olsen et al.

[11] Patent Number: 5,872,138
[45] Date of Patent: Feb. 16, 1999

[54] THROMBIN INHIBITORS

[75] Inventors: Adel M. Naylor-Olsen; Gerald S. Ponticello, both of Lansdale; Joseph P. Vacca, Telford; Randall W. Hungate, Lansdale; Craig Coburn, Skippack; Brian T. Phillips, Telford; S. D. Lewis, Lansdale; Mark E. Fraley, North Wales, all of Pa.

[73] Assignee: Merck & Co., Inc., Rahway, N.J.

[21] Appl. No.: 926,606

[22] Filed: Sep. 10, 1997

[51] Int. Cl.[6] .................... A61K 31/44; C07D 213/72
[52] U.S. Cl. .................... 514/352; 514/255; 514/637; 544/383; 546/312; 564/245
[58] Field of Search .................... 546/312; 544/383; 564/245; 514/352, 255, 637

[56] References Cited

U.S. PATENT DOCUMENTS

| 5,084,466 | 1/1992 | Alig | 514/353 |
|---|---|---|---|
| 5,260,307 | 11/1993 | Ackermann et al. | 514/323 |
| 5,405,854 | 4/1995 | Ackermann et al. | 514/315 |
| 5,459,142 | 10/1995 | Tonee et al. | 514/252 |
| 5,510,369 | 4/1996 | Lumma et al. | 514/422 |
| 5,518,735 | 5/1996 | Sturzebecher et al. | 424/449 |
| 5,612,363 | 3/1997 | Mohan et al. | 514/392 |

FOREIGN PATENT DOCUMENTS

| 0 262 096 | 3/1988 | European Pat. Off. |
| 0 509 769 A2 | 10/1992 | European Pat. Off. |
| 94/25051 | 11/1994 | WIPO |
| 96/11697 | 4/1996 | WIPO |
| 96/31504 | 10/1996 | WIPO |
| 96/32110 | 10/1996 | WIPO |
| 97/01338 | 1/1997 | WIPO |

OTHER PUBLICATIONS

Johnson RA et al. J. Med Chem. 29(8), pp. 1461–1468, 1986.

Cohen T and Deets GL. J. Am. Chem. Soc. 94 (3), pp. 932–937, Feb. 1972.

Efange MN et al. J. Med. Chem. 33 (12), pp. 3133–3138, 1990.

Archibald JI and Benke GA. J Med. Chem. 17 (7), pp. 736–739, 1974.

Mack et al., J. Enzyme Inhibition, "Design, Synthesis and Biological Activity of Novel Rigid Amidino–Phenylalanine . . . ", vol. 9, pp. 73–86 (1965).

Bernstein, et al., J. Med. Chem., 37, 3313–3326 "Nonpeptidic Inhibitors of Human Leukocyte Elastase . . . ", 1994.

*Primary Examiner*—John Kight
*Assistant Examiner*—Evelyn Huang
*Attorney, Agent, or Firm*—Richard S. Parr; Melvin Winokur

[57] ABSTRACT

A compound which inhibits human thrombin and which has the general structure

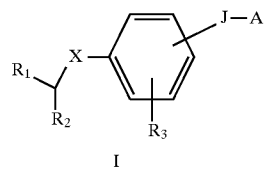

such as

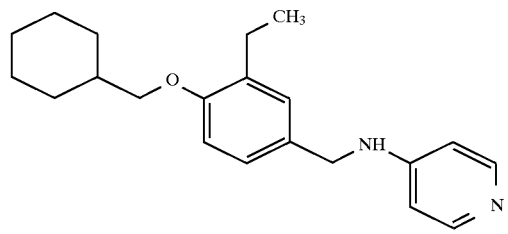

13 Claims, No Drawings

THROMBIN INHIBITORS

This application claims benefit of the provisional application 60/026,033, filed on Sep. 13, 1996.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or α-keto carboxyl derivatives.

Thrombin inhibitors described in prior publications contain sidechains of arginine and lysine. These structures show low selectivity for thrombin over other trypsin-like enzymes. Some of them show toxicity of hypotension and liver toxicity.

European Publication 601 459 describes sulfonamido heterocyclic thrombin inhibitors, such as N-[4-[(aminoiminomethyl)amino]butyl]-1-[N-(2-naphthalenylsulfonyl)-L-phenylalanyl]-L-prolinamide.

WO 94/29336 describes compounds which are useful as thrombin inhibitors.

SUMMARY OF THE INVENTION

A compound which inhibits human thrombin and which has the general structure

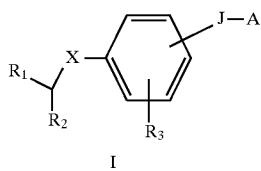

such as

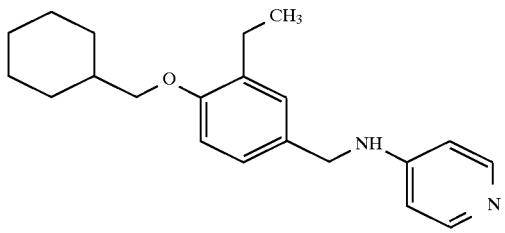

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes the use of a compound of the invention in the manufacture of a medicament for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal.

The invention also includes a method for reducing the thrombogenicity of a surface in a mammal by attaching to the surface, either covalently or noncovalently, a compound of the invention.

DETAILED DESCRIPTION OF THE INVENTION

Compounds of the invention have the following structure:

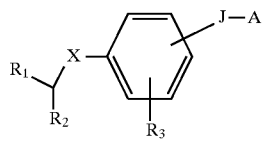

and pharmaceutically acceptable salts thereof wherein
X is
—N($R^4$)—,
—O—,
—S—,
—$SO_2$—,
—SO—,
—$OCH_2(CH_2)_n$ aryl-, or
—$OCH_2(CH_2)_n$ $C_{3-8}$cycloalkyl-,
wherein n is 1 or 2;
J is
—$(CH_2)_m$—,
—$(CH_2)_m$NH—,
—$SO_2$NH—,
—$SO_2(CH_2)_m$—,
—$NHSO_2$—,
—$SO_2$—, or
—$(CH_2)_mSO_2$—,
wherein m is 1 or 2;
$R^1$, $R^2$, and $R^4$ are independently selected from
hydrogen,
aryl,
—$CO_2R^5$,
aryl $C_{1-4}$ alkyl,
diaryl $C_{1-4}$ alkyl,
dicyclo $C_{3-8}$ alkyl $C_{1-4}$ alkyl, cyclo $C_{3-8}$ alkyl $C_{1-4}$ alkyl,

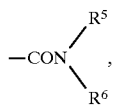

wherein $R^5$ and $R^6$ are independently hydrogen or $C_{1-4}$ alkyl,
substituted aryl with one or two substituents selected from
$C_{1-4}$ alkyl,
$C_{1-4}$ alkoxy,

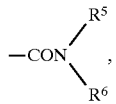

wherein $R^5$ and $R^6$ are independently hydrogen or $C_{1-4}$ alkyl,
aryloxy,
cyclo $C_{3-8}$ alkoxy,
methylenedioxy,
halogen, or
hydroxy,
heteroaryl with one or two heteroatoms selected from N, O, and S, cyclo $C_{3-7}$ alkyl unsubstituted or substituted with one or more of $C_{1-4}$ alkyl, $C_{1-4}$ alkoxy, benzyl, cyclohexylmethyl or aryl,
a $C_{4-10}$ carbocyclic or bicyclic ring, or
$R^1$ and $R^2$ along with the carbon to which they attach form a cyclo $C_{3-7}$ alkyl ring;
$R^3$ is
hydrogen,
$C_{1-4}$ alkyl,
$C_{1-4}$ alkenyl,
$C_{1-4}$ alkoxy,
—$NHR^7$ wherein $R^7$ is hydrogen or $C_{1-4}$ alkyl, or
—$NHSO_2CH_2$aryl;
A is selected from one of the following fragments

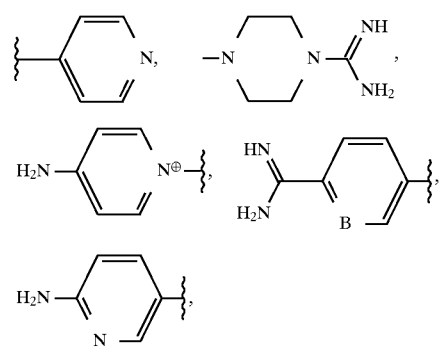

One group of compounds of the invention have the following structure:

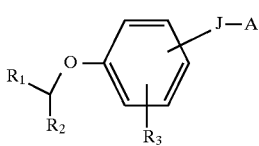

and pharmaceutically acceptable salts thereof wherein
J is $(CH_2)_m$, $(CH_2)_m NH$, or $SO_2$, where m is 1 or 2;
$R^1$ and $R^2$ are independently selected from
hydrogen,
aryl, or
cyclo $C_{3-7}$ alkyl unsubstituted or substituted with one or more of $C_{1-4}$ alkyl, $C_{1-4}$ alkoxy, benzyl, cyclohexylmethyl or aryl;
$R^3$ is
hydrogen,
$C_{1-4}$ alkyl, or
$C_{1-4}$ alkenyl;
A is selected from one of the following fragments

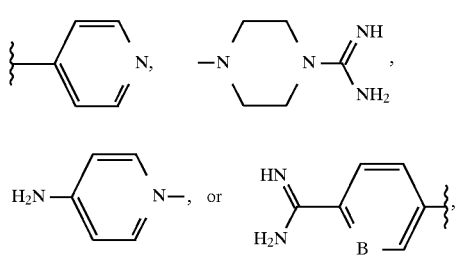

One class of this group of compounds has the following structure:

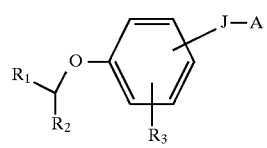

and pharmaceutically acceptable salts thereof wherein

J is $CH_2$, $CH_2NH$, or $SO_2$;
$R^1$ and $R^2$ are independently selected from
hydrogen,
aryl, or
cyclohexyl;
$R^3$ is
hydrogen,
—$CH=CH_2$ or
—$CH_2CH_3$; and
A is selected from one of the following fragments

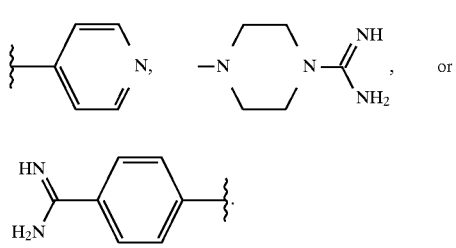

Specific exemplifications of this class are

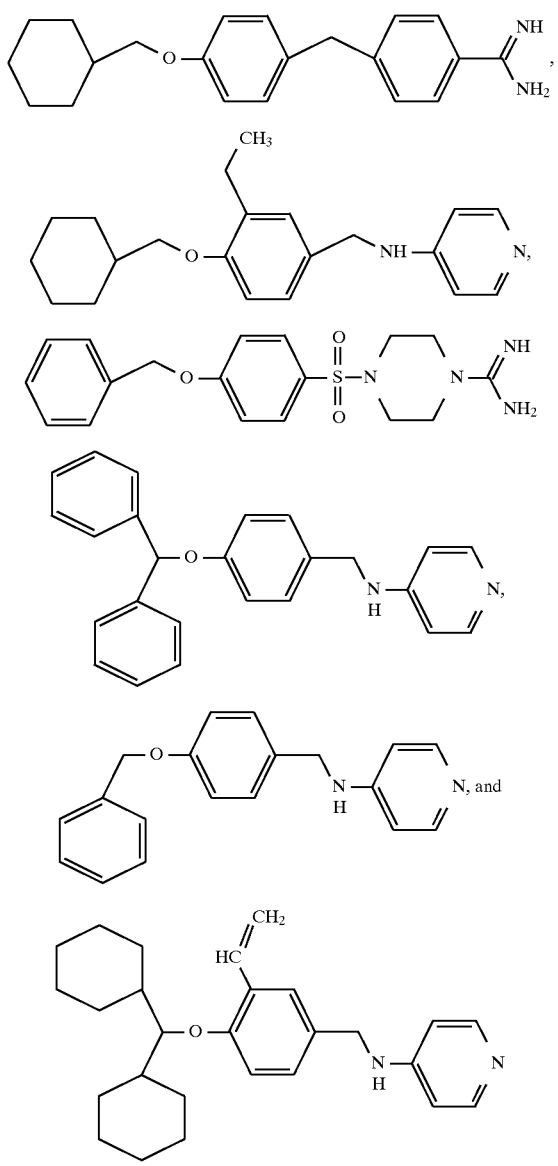

and pharmaceutically acceptable salts thereof.

ABBREVIATIONS

| Designation | |
|---|---|
| BOC (Boc) | t-butyloxycarbonyl |
| HBT(HOBT or HOBt) | 1-hydroxybenzotriazole hydrate |
| BBC reagent | benzotriazolyloxy-bis(pyrrolidino)-carbonium hexafluorophosphate |
| PyCIU | 1,1,3,3-bis(tetramethylene)-chlorouronium hexafluorophosphate |
| EDC | 1-ethyl-3-(3-dimethylaminopropyl)carbodiimide hydrochloride |
| (BOC)$_2$O | di-t-butyl dicarbonate |
| DMF | dimethylformamide |
| Et$_3$N or TEA | triethylamine |
| EtOAc | ethyl acetate |
| TFA | trifluoroacetic acid |
| DMAP | dimethylaminopyridine |
| DME | dimethoxyethane |
| BH3-THF | Borane-tetrahydrofuran complex |
| D-Phe(3,4-Cl$_2$) | D-3,4-Dichlorophenylalanine |

-continued

| Designation | |
|---|---|
| D-3,3-dicha | D-3,3-Dicyclohexylalanine |
| Pro | Proline |
| Arg | Arginine |
| Gly | Glycine |
| D-3,3,-diphe | D-3,3-Diphenylalanine |

The compounds of the present invention may have chiral centers and occur as racemates, racemic mixtures and as individual diastereomers, or enantiomers with all isomeric forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

As used herein, except where noted, "alkyl" is intended to include both branched- and straight-chain saturated aliphatic hydrocarbon groups having 1–8 carbon atoms (Me is methyl, Et is ethyl, Pr is propyl, Bu is butyl). "Alkenyl" is intended to include both branched- and straight-chain unsaturated aliphatic hydrocarbon groups having 1–8 carbon atoms, e.g. ethenyl, propenyl, etc. "Cycloalkyl" includes cyclic saturated aliphatic hydrocarbon groups having 3–8 carbon atoms. "Aryl" means a 6-membered organic radical derived from an aromatic hydrocarbon by removal of one hydrogen atom. "Heteroaryl" means a 5- or 6-membered organic radical having 1 or 2 heteroatoms selected from N, O, and S. "Alkoxy" represents an alkyl group having 1–8 carbon atoms attached through an oxygen bridge. "Halo", as used herein, means fluoro, chloro, bromo and iodo. "Counterion" is used to represent a small, single negatively-charged species, such as chloride, bromide, hydroxide, acetate, trifluroacetate, perchlorate, nitrate, benzoate, maleate, tartrate, hemitartrate, benzene sulfonate, and the like.

Under standard nonmenclature used throughout this disclosure unless specified otherwise, the terminal portion of the designated side chain is described first followed by the adjacent functionality toward the point of attachment. For example, an ethyl substituent substituted with "methylcarbonylamino" is equivalent to

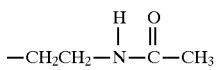

The term heterocycle or heterocyclic, as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quatemized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others.

Amide couplings used to form the compounds of this invention are typically performed by the carbodiimide method with reagents such as dicyclohexylcarbodiimide, or 1-ethyl-3-(3-dimethylaminopropyl) carbodiimide. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice.

Compounds of the invention can be prepared according to the general procedures outlined in Schemes I–VI.

Compounds found in table 1 were synthesized by the general method outlined in Scheme I and are exemplified by, but not limited to the examples 1–9. A phenolic ester such as ethyl 4-hydroxybenzoic acid (1) is alkylated with an alkyl bromide such as benzyl bromide by using a base such as cesium carbonate to afford the product I-3. The ester group is then reduced with a hydride reducing agent such as lithium aluminum hydride to afford the benzylic alcohol I-4. The benzylic alcohol is converted into a leaving group (such as a bromide or triflate) and the benzylic leaving group is reacted with 4-aminopyridine to afford the final product.

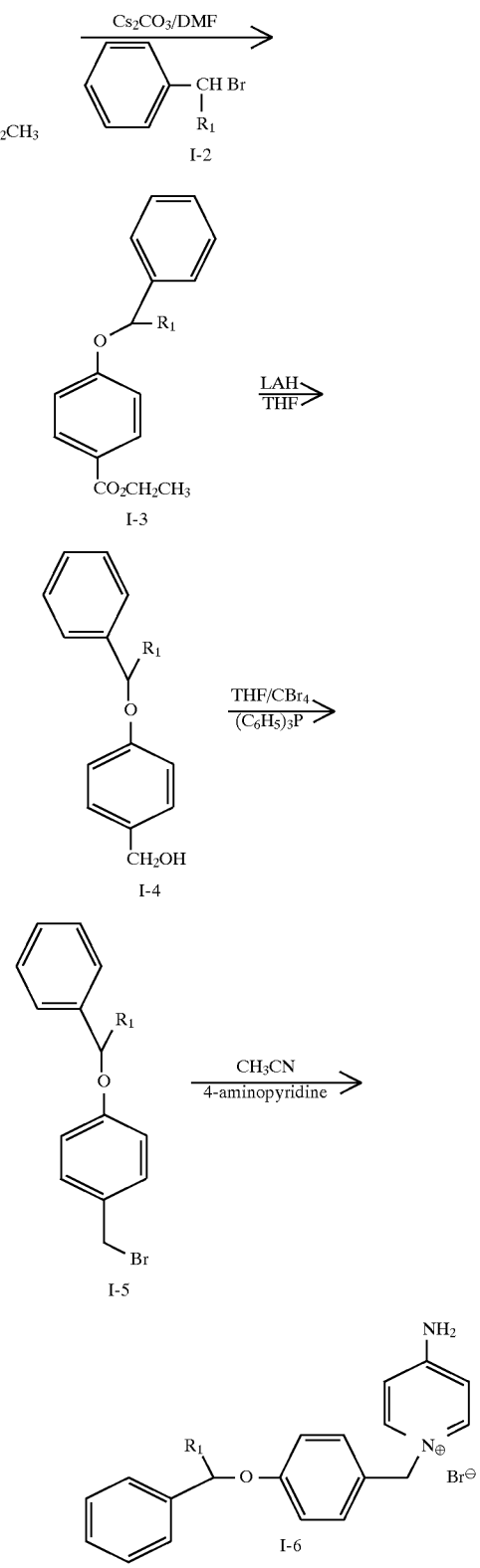

A general method for synthesizing compounds found in tables 2 and 3 is outlined Scheme II. A benzoic acid such as II-1 (obtained in standard fashion) is coupled to 4-aminopyridine under standard amide bond coupling conditions. The resultant amide II-2 is then reduced with lithium aluminum anhydride to afford the desired product II-3.

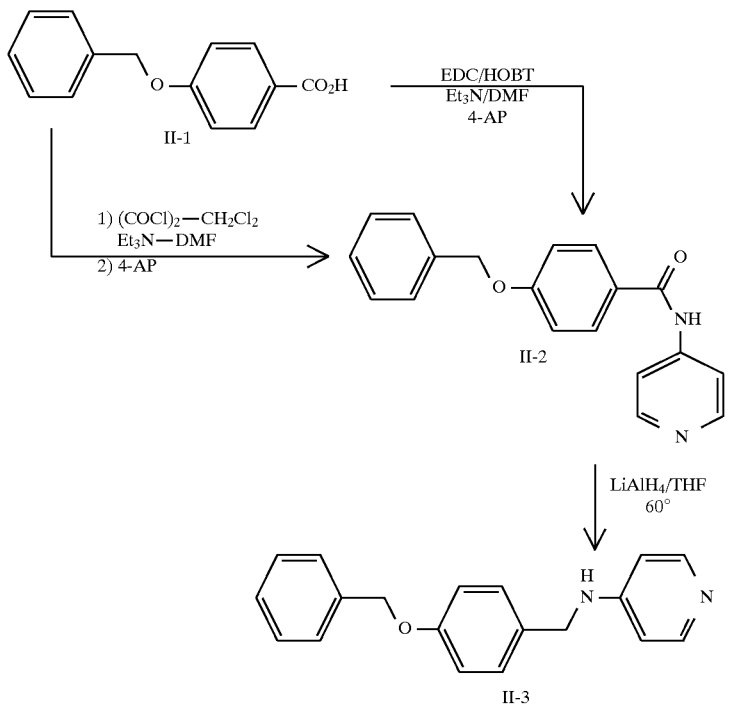

A general method for synthesizing compounds found in table 2 is outlined Schemes II and III. A benzoate ester such as III-4 (obtained in standard fashion) is reacted with an alkylating reagent (such as bromomethyl cyclohexane) to afford O-alkylated product III-5. The ester is hydrolyzed with an aqueous base and is coupled to 4-aminopyridine under standard amide bond coupling conditions. The resultant amide III-7 is then reduced with lithium aluminum hydride to afford the desired product III-8.

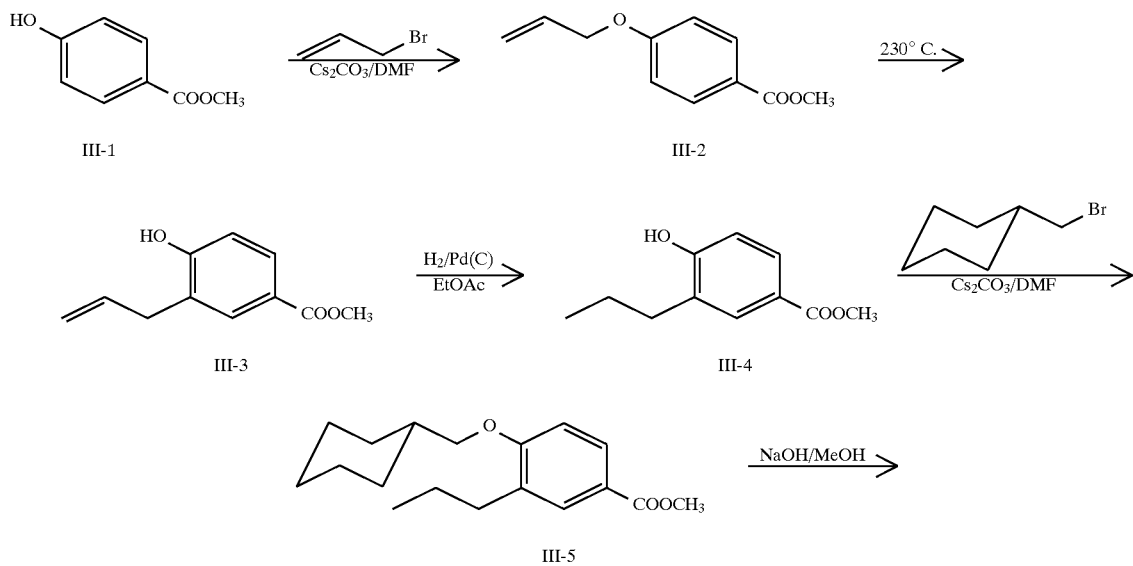

-continued
SCHEME III

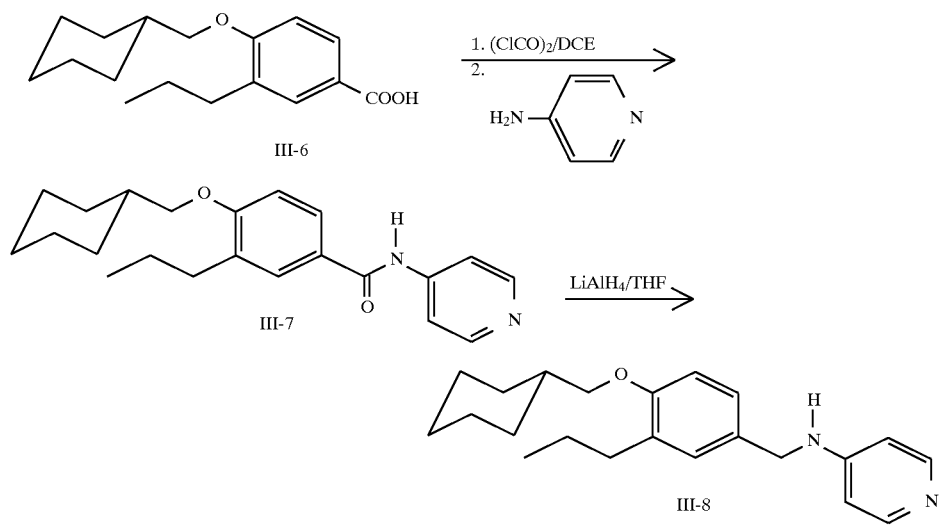

SCHEME IV

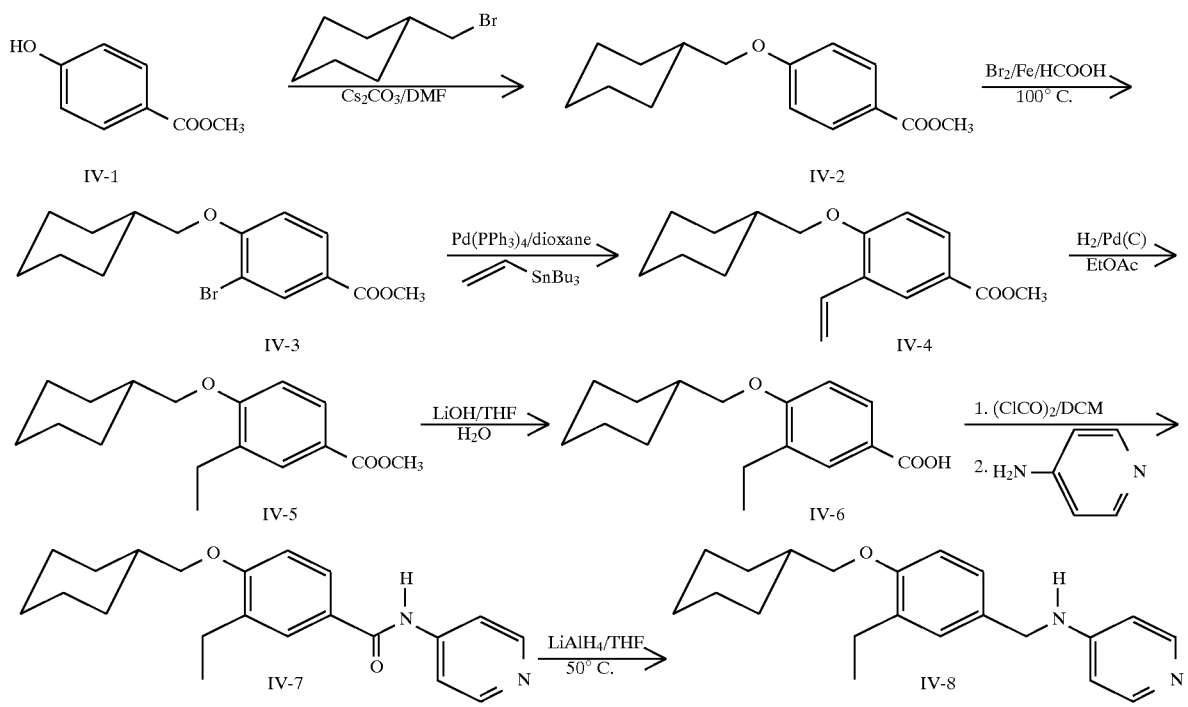

A method for preparing compounds found in table 4 is outlined in Scheme V. Substituted benzene compound such as 4-benzyloxy-benzene (V-1) is reacted with sulfuryl chloride at 80°–120° C. to give a sulfonyl chloride. The sulfonyl chloride (V-2) is reacted with Boc-piperazine and the Boc protecting group is removed with a strong acid to afford the deprotected piperazine. The free nitrogen is converted to the amidine with a guanylating reagent such as amidinosulfonic acid.

SCHEME V

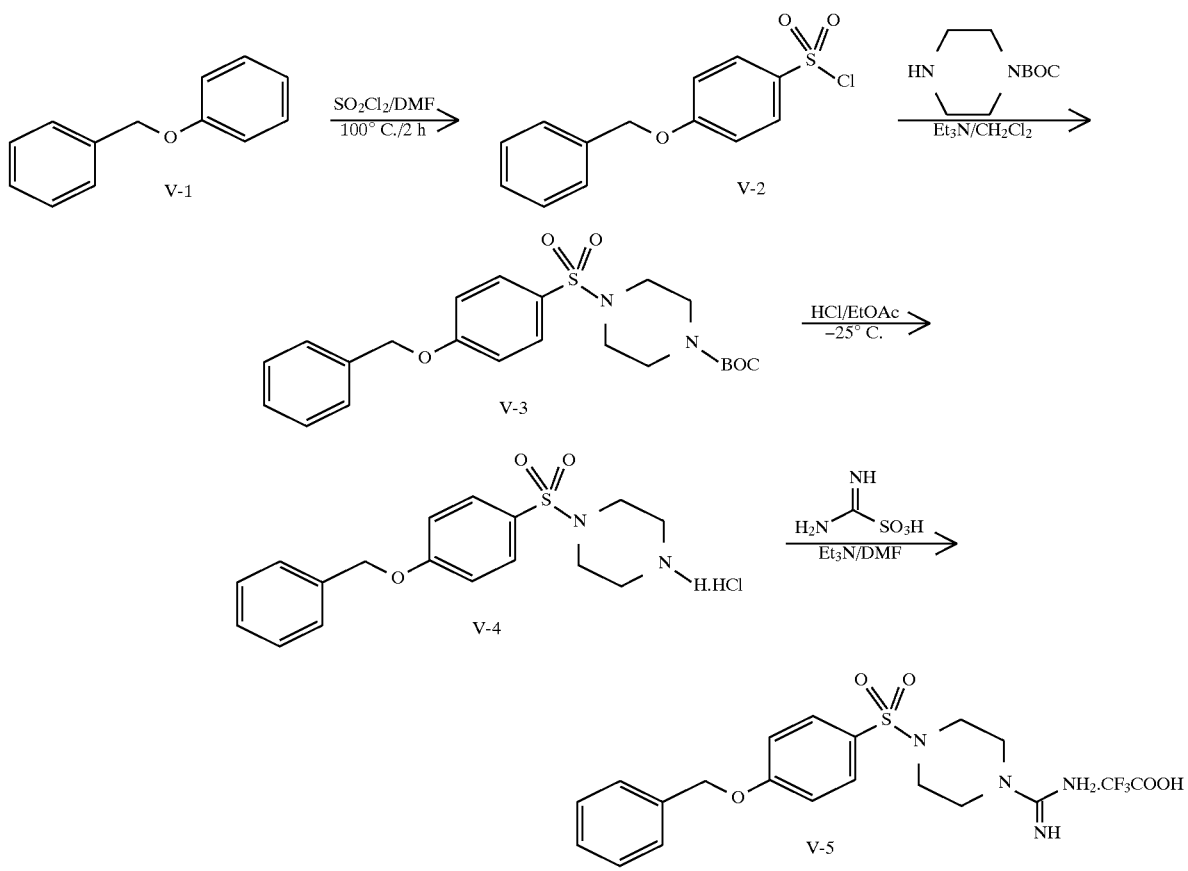

A general method for synthesizing compounds found in table 5 is outlined in Scheme VI. The ketone of a cyano-benzophenone such as 1 is reduced with a metal hydride reagent such as sodium borohydride and the resultant alcohol is removed by treatment with dimethyldichlorosilane to afford the diphenylmethane VI-3. The methoxy group is removed with borontribromide and the phenol is alkylated with an alkylating reagent such as benzyl bromide. The cyano group is then treated with sodium hexamethyldisilazane and the silylimidate is hydrolyzed with an acidic workup to afford the final product.

SCHEME VI

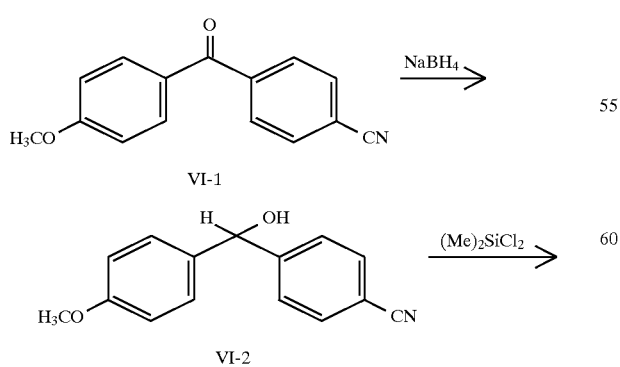

-continued
SCHEME VI

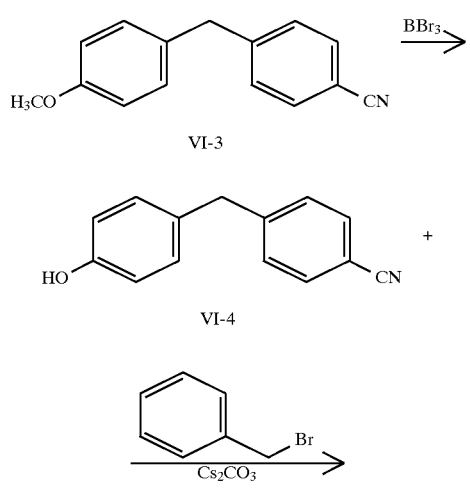

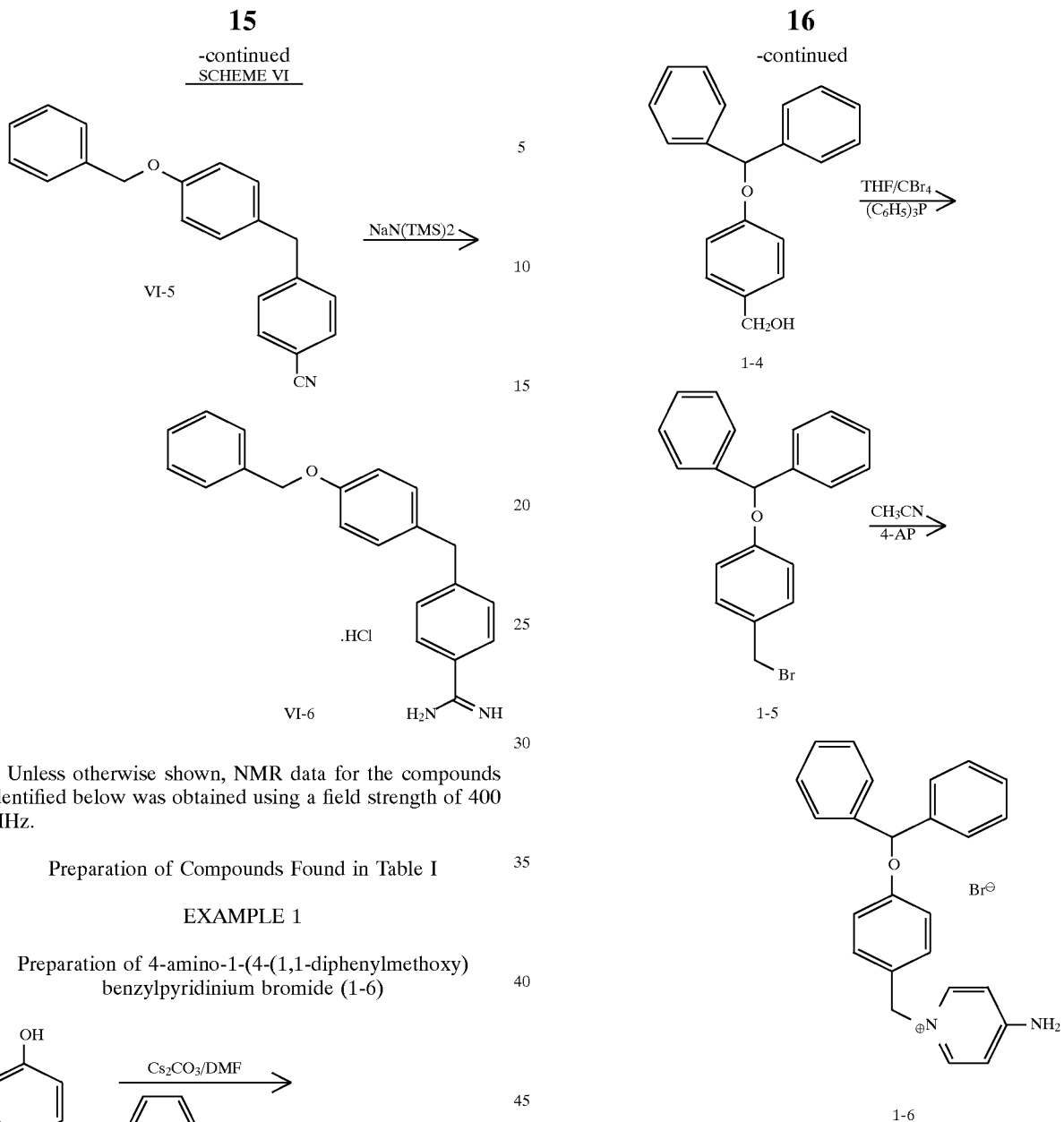

Unless otherwise shown, NMR data for the compounds identified below was obtained using a field strength of 400 MHz.

Preparation of Compounds Found in Table I

EXAMPLE 1

Preparation of 4-amino-1-(4-(1,1-diphenylmethoxy) benzylpyridinium bromide (1-6)

Step A:
Preparation of ethyl 4-(1,1-diphenylmethoxy)benzoate (1-3)
Under $N_2$, a mixture of ethyl 4-hydroxybenzoic acid (2.5 g, 15 mmol) 1-1, and $Cs_2CO_3$ (5.0 g, 15 mmol) in DMF (50 ml) was stirred at room temperature. After 15 min, diphenylmethyl bromide 1-2 (4.0 g, 16 mmol) was added and then heated at 60° C. After 1 h, saturated $Na_2CO_3$ was added and the mixture extracted with EtOAc (3×). The combined extracts were washed with $H_2O$, dried, filtered and concentrated to dryness to yield 1-3.
$^1$H NMR (CDCl$_3$) δ 1.3 (3H, t), 4.3 (2H, q), 6.95 (2H, s), 7.3 (10H, m) and 7.95 (2H, d).

Step B:
Preparation of 4-(1,1-diphenylmethoxy)benzyl alcohol (1-4)
To a suspension of LAH (3.2 g, 0.084 mmol) in THF (400 ml) under $N_2$ was added dropwise a solution of 1-3 (21 g, 0.063 mol) in THF (100 ml). After stirring overnight at room temperature, saturated $Na_2SO_4$ was added to the reaction until a white suspension was observed. The mixture was filtered and the filtrate was combined with H$_2$O and CHCl$_3$, separated, and extracted further with CHCl$_3$ (2×). The combined organic extracts were dried, filtered and concentrated to dryness. The residue was triturated with hexane to yield 1-4.

$^1$H NMR δ 1.6 (1H, bs), 4.55 (2H, s), 6.2 (1H, s), 6.95 (2H, d), and 7.3 (12H, m).

Step C:

Preparation of 4-(1,1-diphenylmethoxy)benzyl bromide (1-5)

A solution of 1-4 (3.6 g, 12 mmol), triphenyl phosphine (3.1 g, 11.8 mmol) in THF (100 ml) was treated with carbon tetrabromide (3.9 g, 11.8 mmol). After 12 h additional triphenylphosphine (3.1 g, 11.8 mmol) was added and the mixture allowed to stir at room temperature overnight. Some triphenyl phosphine oxide was then filtered off and the filtrate concentrated to dryness. The residue was chromatographed on a Still column (70 mm) and the product eluted with 5% EtOAc-hexane to yield 1-5.

$^1$H NMR (CDCl$_3$) δ 4.4 (2H, s), 6.2 (1H, s), 6.9 (2H, d) and 7.35 (12H, m).

Step D:

Preparation of 4-amino-1-(4-(1,1-diphenylmethoxy)benzyl)pyridium bromide (1-6)

A solution of 1-5 (0.58 g, 1.6 mmol) in CH$_3$CN (25 ml) was treated under N$_2$ with 4-aminopyridine (0.16 g, 1.7 mmol). After stirring overnight at room temperature, the solid was filtered off to yield 1-6. An analytical sample was crystallized from CH$_3$CN.

mp: 254°–5°.

Analysis calculated for C$_{25}$H$_{23}$BrN$_2$O C, 67.12; H, 5.18; N, 6.26

Found: C, 67.25; H, 5.07; N, 6.25

$^1$H NMR (d$_6$-DMSO) δ 5.2 (2H, s), 6.55 (1H, s), 6.8 (2H, d), 7.05 (2H, d), 7.3 (8H, m), 7.47 (4H, d), 8.13 (2H, bs exch) and 8.25 (2H, d).

EXAMPLE 2

Preparation of 4-amino-1-(4-(2-phenyl-1-ethoxy)benzyl)pyridinium bromide (2-2)

2-2 was prepared as described for the preparation of 1-6 except 2-phenyl-1-bromoethane (2-1) was used in place of 1-2 in Step A and synthesized. mp: 170°–1° C. (CH$_3$CN);

$^1$H NMR (d$_6$-DMSO) δ 3.0 (2H, t), 4.2 (2H, t), 5.3 (2H, s), 6.82 (2H, d), 6.96 (2H, d), 7.3 (7H, m), 8.15 (2H, exch bs) and 8.27 (2H, d).

Analysis calculated for C$_2$OH$_{21}$BrN$_2$O C, 59.96; H, 5.71; N, 6.99

Found: C, 59.62; H, 5.22; N, 7.14

EXAMPLE 3

Preparation of 4-amino-1-(4-(cyclohexylmethoxy)benzyl)pyridinium bromide (3-3)

3-3 was prepared as described for the synthesis of 1-6 except 4-hydroxy-benzyl alcohol (3-1) and cyclohexylmethyl bromide (3-2) were used in Step A to yield 4-(cyclohexylmethoxy)benzyl alcohol directly. mp: 241°–3° C.;

$^1$H NMR (d$_6$-DMSO) δ 1.2 (5H, m), 1.75 (6H, m), 3.8 (2H, d), 5.28 (s, 2H), 6.8 (2H, d), 6.95 (2H, d), 7.34 (2H, d), 8.1 (2H, exch bs), 8.25 (2H, d).

Analysis calculated for C$_{19}$H$_{25}$BrN$_2$O C, 60.47; H, 6.68; N, 7.42

Found: C, 60.57; H, 6.70; N, 7.15

EXAMPLE 4

Preparation of 4-amino-1-(4-(1-phenyl-1-carbomethoxy)methoxybenzyl)pyridinium bromide (4-2)

4-2 was prepared as described for the synthesis of 1-6 except methyl 1-bromo-1-phenylacetate (4-1) was used in place of 1-2 in Step A. The compound was crystallized from CH$_3$CN; mp: 188°–90° C.;

$^1$H NMR (d$_6$-DMSO) δ 3.65 (3H, s), 5.27 (2H, s), 6.05 (1H, s), 6.83 (2H, d), 7.2 (2H, d), 7.34 (2H, d), 7.42 (3H, m), 7.54 (2H, d), 8.14 (2H, exch bs) and 8.27 (2H, d).

Analysis calculated for C$_{21}$H$_{21}$BrN$_2$O.0.25 H$_2$O C, 58.14; H, 5.00; N, 6.46

Found: C, 57.77; H, 4.94; N, 6.69

EXAMPLE 5

Preparation of 4-amino-1-(4-(2,2-dicyclohexyl-1-ethoxy)benzyl)pyridinium bromide (5-5)

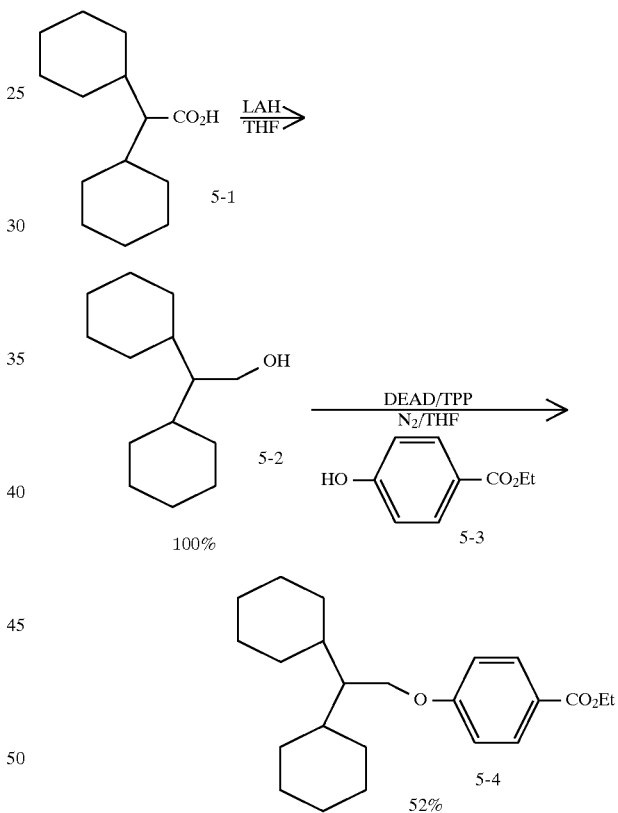

Step A:

Preparation of 1,1-dicyclohexyl-2-hydroxy ethane (5-2)

A solution of 1,1-dicyclohexylacetic acid (5-1) (2.8 g, 12.5 mmol) in THF (5 ml) under N$_2$ was cooled in an ice bath and then 1.0M borane in THF (17 ml, 17 mmol) was added dropwise. After addition, the solution was stirred at room temperature and then a 1:1 mixture of THF/H$_2$O (10 ml) was added carefully. The mixture was added to saturated Na$_2$CO$_3$ and extracted with EtOAc (3×). The organic extracts were dried, filtered and concentrated to dryness to yield 5-2.

$^1$H NMR (CDCl$_3$); δ 1.1 (11H, m), 1.6 (12H, m), 3.65 (2H, d).

Step B:

Preparation of ethyl 4-(1,1-dicyclohexyl)ethoxybenzoate (5-4)

Under $N_2$, 5-2 (1.1 g, 5.2 mmol), ethyl 4-hydroxybenzoate (5-3) (0.9 g, 5.2 mmol), triphenylphosphine (1.6 g, 5.2 mmol), diethyl azodicarboxylate (1.1 g, 6.2 mmol) in THF (15 ml) were placed in a flask and stirred at room temperature. After 2 days, water and $Et_2O$ were added and separated. The aqueous layer was further extracted with $Et_2O$ (2×) and the combined layers backwashed with saturated $Na_2CO_3$, brine, dried, filtered and concentrated to dryness. The residue was chromatographed on a Still column (40 mm) and the product eluted with 20% EtOAc/hex to yield 5-4.

5-4 was converted to 5-5 as described in Example 1; mp: 223°–5° C.;

$^1$H NMR ($d_6$-DMSO) δ 1.4 (23H, m), 3.93 (2H, s), 5.26 (2H, s), 6.85 (2H, d), 6.95 (2H, d), 7.37 (2H, d), 8.15 (2H, exch bs) and 8.3 (2H, d).

Analysis calculated for $C_{26}H_{37}N_2OBr.0.75 H_2O$ C, 64.12; H, 7.97; N 5.75

Found: C, 64.25; H, 7.66; N 5.83

EXAMPLE 6

Preparation of 4-amino-1-[4-(1,3-diphenyl-1-propoxy) benzyl]pyridinium bromide (6-8)

Step A:

Preparation of 1,3-diphenylpropanol (6-2)

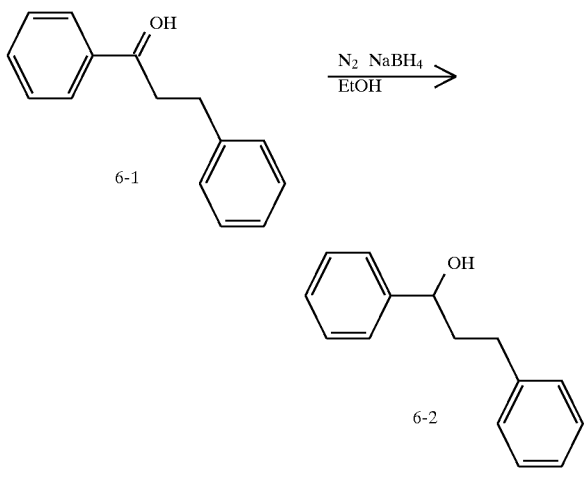

β-Phenylpropiophenone (6-1) (7.5 g, 36.0 mmol) was suspended in ethanol (100 ml) and sodium borohydride (0.68 g, 18.0 mmol) was added under $N_2$. The resulting solution was stirred at ambient temperature overnight. The ethanol was removed in vacuo and the residual oil-solid was taken up in ethyl acetate (100 ml) and water (30 ml). The ethyl acetate layer was removed, washed with water, dried, filtered and concentrated in vacuo to give 6-2 as a colorless oil.

$^1$H NMR ($d_6$-DMSO) δ 1.88 (2H, q), 2.6 (2H, m), 4.51 (1H, q), 5.28 (1H, d), 7.1–7.37 (10H, m).

Step B:

Preparation of ethyl 4-(1,3-diphenyl-1-propoxy)benzoate (6-4)

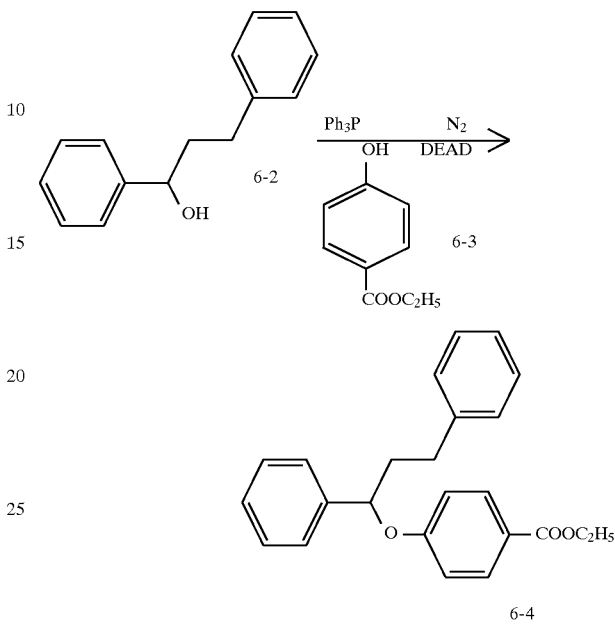

To 6-2 (2.12 g, 10.0 mmol) in tetrahydrofuran (25 ml) under a nitrogen atmosphere was added ethyl 4-hydroxybenzoate (6-3) (1.66 g, 10.0 mmol) followed by triphenyl phosphine (3.15 g, 12.0 mmol). The mixture was cooled in an ice bath and diethyl azodicarboxylate (2.09 g, 12 mmol) was added. This mixture was stirred overnight at ambient temperature and the solvent was removed in vacuo. The residue was taken up in the water and the ether layer was separated, washed with sodium bicarbonate and water, dried, filtered and concentrated in vacuo to yield an oil. Chromatographic purification on silica gel gave 6-4 as a colorless oil.

$^1$H NMR ($d_6$-DMSO) δ 1.25 (3H, t), 2.1 (1H m), 2.25 (1H, m), 2.66 (1H, m), 2.75 (1H, m), 4.22 (2H, q), 5.4 (1H, t), 6.99 (2H, d), 7.12–7.44 (10H, m), 7.8 (2H, d).

Step C:

Preparation of 4-(1,3-diphenyl-1-propoxy)benzyl alcohol (6-5)

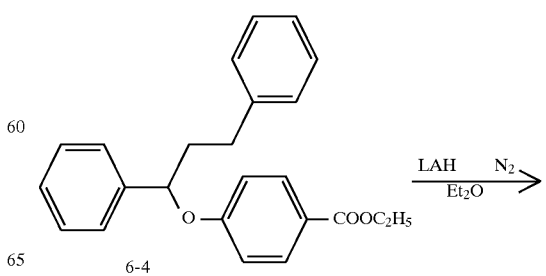

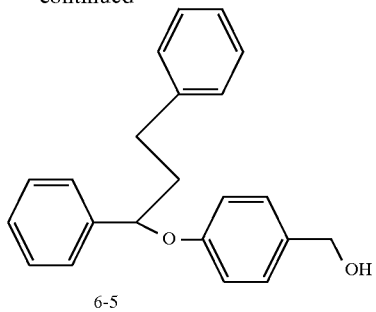

6-5

A solution of 6-4 (2.46 g, 6.8 mmol) in ether (30 ml) was added dropwise under nitrogen atmosphere to a stirred cold suspension of lithium aluminum hydride (0.285 g, 7.5 mmol) in ether (5 ml). The mixture was stirred for 3 hrs at ambient temperature and was decomposed by carefully adding water and sodium hydroxide. This mixture was extracted with ethyl acetate. The extract was washed with water, dried, filtered and concentrated in vacuo to yield 6-5 as a colorless viscous oil.

$^1$H NMR (d$_6$-DMSO) δ 2.05 (1H, m), 2.2 (1H, m), 2.66 (1H, m), 2.75 (1H, m), 4.34 (2H, d), 4.99 (1H, t), 5.26 (1H, t), 6.81 (2H, d), 7.04–7.4 (12H, m).

Step D:

Preparation of 4-(1,3-diphenyl-1-propoxy)benzyl bromide (6-6)

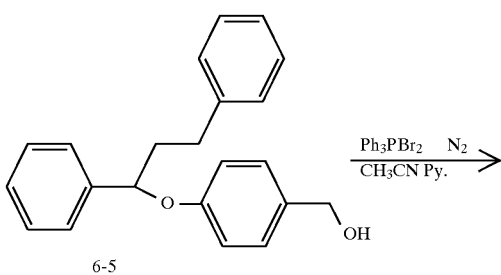

To an ice cold solution of 6-5 (1.19 g, 6.0 mmol) in acetonitrile (15 ml) was added pyridine (0.76 g, 9.6 mmol) and then triphenylphosphine dibromide (3.29 g, 7.8 mmol). The mixture was stirred at ice bath temperature for ¼ hr under N$_2$ and at ambient temperature for 1 &¾ hrs and then was filtered. Concentration of the filtrate in vacuo gave a crude oil. The pure product 6-6 was obtained after three silica gel chromatographic separations.

$^1$H NMR (d$_6$-DMSO) δ 2.06 (1H, m), 2.2 (1H, m), 2.66 (1H, m), 2.75 (iH, m), 4.62 (2H, s), 5.3 (1H, t), 6.82 (2H, d), 7.16–7.4 (12H, m).

Step E:

Preparation of 4-amino-1-[4-(1,3-diphenyl-1-propoxy)-benzyl]pyridinium bromide (6-8)

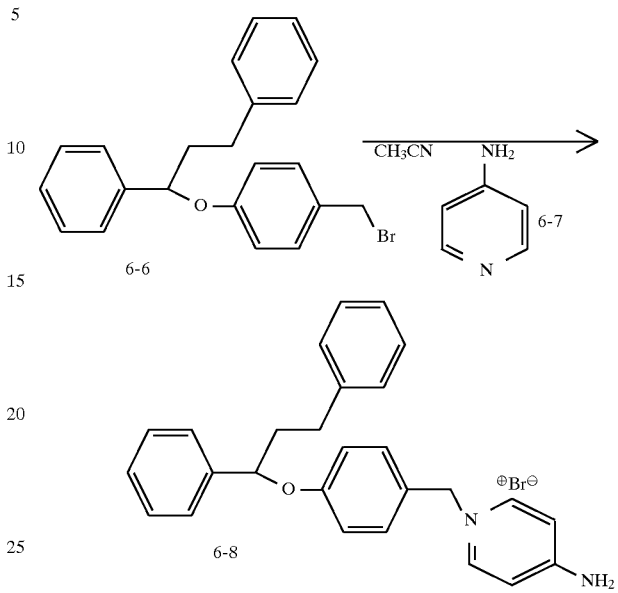

To a solution of 4-(1,3-diphenyl-1-propoxy)benzyl bromide 6-6 (0.381 g, 1.0 mmol) in acetonitrile (7 ml) was added 4-aminopyridine (6-7) (94 mg, 1.0 mmol) with stirring at room temperature. The mixture was stirred for 3 hrs and the resulting white suspension was filtered. The white solid obtained 6-8, melted at 215°–216.5° C. Recrystallization from acetonitrile raised the melting point to 218.5°–220° C.

$^1$H NMR (d$_6$-DMSO) δ 2.06 (1H, m), 2.2 (1H, m), 2.65 (1H, m), 2.75 (1H, m), 5.2 (2H, s), 5.3 (1H, m), 6.8 (2H, d), 6.9 (2H, d), 7.16–7.41 (12H, m), 8.12 (2H, s), 8.24 (2H, d).

Analysis calculated for C$_{27}$H$_{27}$N$_2$OBr C, 68.21; H, 5.73; N, 5.89

Found: C, 68.48; H, 5.68; N, 5.98

EXAMPLE 7

Preparation of 4-amino-1-[4-(2,2-diphenylethoxy) benzyl]pyridinium bromide (7-7)

Step A:

Preparation of ethyl 4-(2,2-diphenylethoxy)benzoate (7-3)

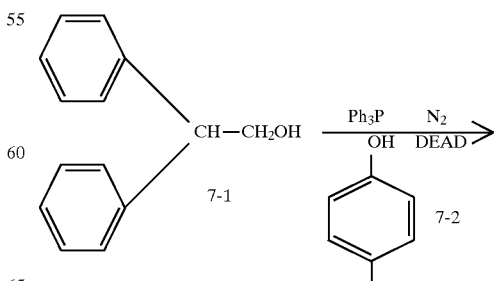

-continued

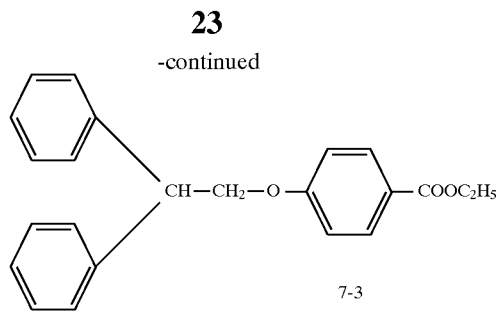

7-3

2,2-Diphenylethanol (7-1) (5.95 g, 30 mmol) and ethyl 4-hydroxybenzoate (7-2) (5.48 g, 30 mmol) were reacted, as in Example 6. 7-3 was obtained after chromatography as a colorless oil.
$^1$H NMR (CDCl$_3$): δ 1.36 (3H, t), 4.33 (2H, q), 4.52 (3H, s), 6.9 (2H, d), 7.2–7.36 (10H, m), 7.96 (2H, d).

Step B:

Preparation of ethyl 4-(2,2-diphenylethoxy)benzyl alcohol (7-4)

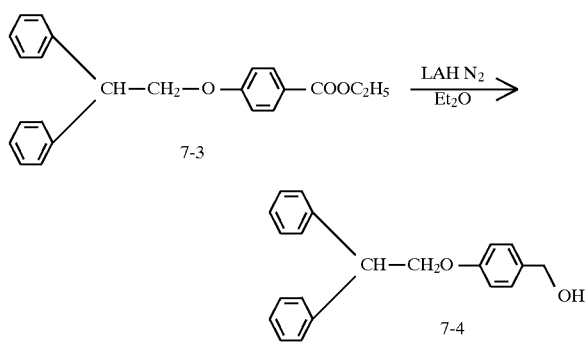

7-3 (0.757 g, 2.2 mmol) was dissolved in ether (20 ml) and was reduced with lithium aluminum hydride (92 mg, 2.4 mmol) under nitrogen as in Example 6, Step B. 7-4 was obtained as a colorless oil.
$^1$H NMR (d$_6$-DMSO) δ 1.55 (1H, t), 4.45–4.52 (3H, m), 4.61 (2H, d), 6.88 (2H, d), 7.2–7.35 (12H, m).

Step C:

Preparation of 4-(2,2-diphenylethoxy)benzyl bromide (7-5)

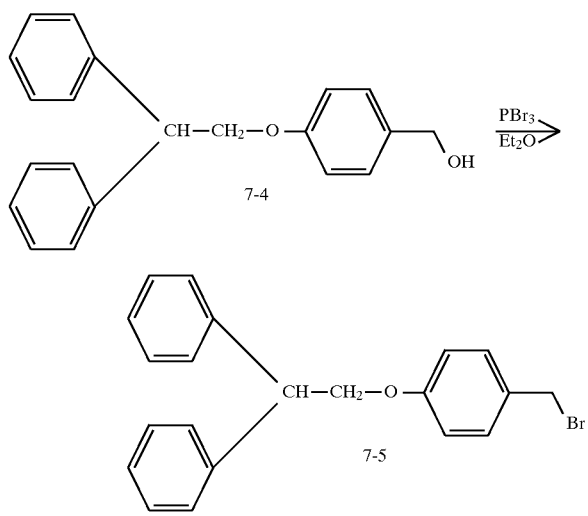

7-4 (0.572 g, 1.9 mmol) was dissolved in ether (10 ml). The solution was cooled in ice and phosphorus tribromide (0.204 g, 0.75 mmol) was added. After ½ hr. the reaction was diluted with methanol (2 ml) and water (5 ml). The ether layer was separated, washed with sodium bicarbonate and water, dried and filtered. Concentration of the filtrate in vacuo gave 7-5 as a white solid. mp: 70°–73° C.
$^1$H NMR (d$_6$-DMSO): δ 4.43–4.62 (3H, m), 4.64 (2H, s), 6.9 (2H, d), 7.15–7.4 (12H, m).

Step D:

Preparation of 4-amino-1-[4-(2,2-diphenyl-ethoxy)-benzyl]pyridinium bromide (7-7)

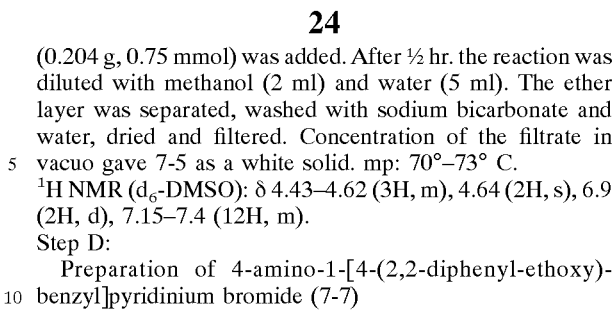

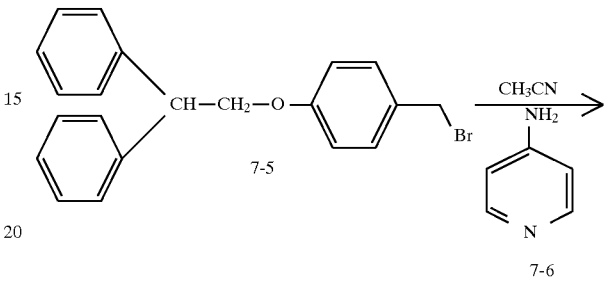

7-5 (100 mg, 0.27 mmol) was reacted with 4-aminopyridine 7-6 (28 mg, 0.30 mmol) in acetonitrile (3 ml) as in Example 6, Step E. The white solid product 7-7 was obtained.
mp: 137°–139° C.
$^1$H NMR (d$_6$-DMSO) δ: 4.45–4.59 (3H, m), 5.27 (2H, s), 6.82 (2H, d), 6.98 (2H, d), 7.17–7.4 (12H, m), 8.13 (2H, s), 8.27 (2H, d).
Analysis calculated for (C$_{26}$H$_{25}$N$_2$OBr.0.5 H$_2$O): C, 66.38; H, 5.57; N, 5.96
Found: C, 66.57; H, 5.42; N, 5.98

EXAMPLE 8

Preparation of 4-amino-1-[4-(dicyclohexylmethoxy)benzyl]pyridinium bromide (8-7)

Step A:

Preparation of ethyl 4-(dicyclohexylmethoxy)benzoate (8-3)

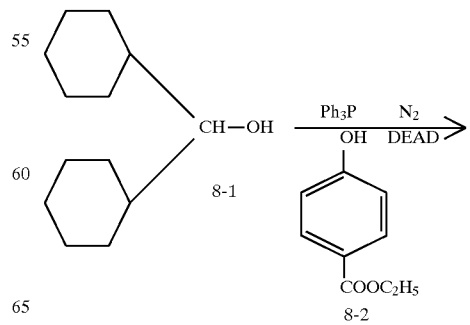

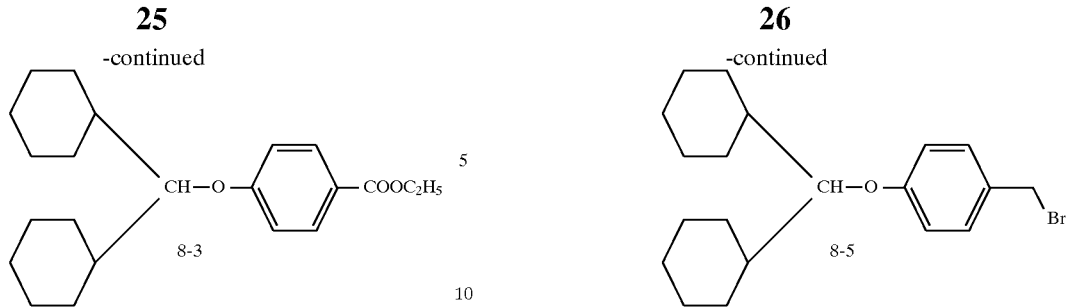

Dicyclohexylmethanol (8-1) (4.91 g, 25 mmol) and ethyl 4-hydroxybenzoate (8-2) (4.15 g, 25 mmol) were reacted, as in Example 6, Step B, to obtain a colorless oil 8-3 after chromatography. $^1$H NMR (CDCl$_3$): δ 0.98–1.3 (11H, m), 1.36 (3H, t), 1.58–1.86 (11H, m), 4.02 (1H, t), 4.33 (2H, q), 6.92 (2H, d), 7.94 (2H, d).

Step B:

Preparation of 4-(dicyclohexylmethoxy)benzyl alcohol (8-4)

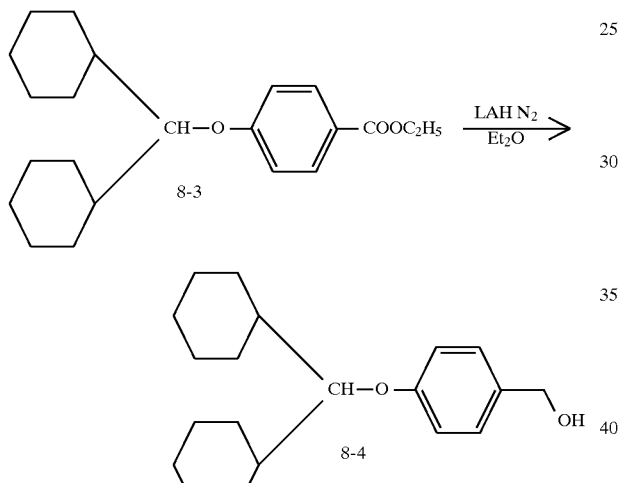

Reduction of 8-3 (2.8 g, 8.1 mmol) with lithium aluminum hydride (0.338 g, 8.9 mmol) in ether (30 ml) as in Example 6 gave 8-4 as a colorless oil.

$^1$H NMR (CDCl$_3$): δ 1.01–1.31 (11H, m), 1.45–1.86 (11H, m), 3.91 (1H, t), 4.6 (2H, d), 6.9 (2H, d), 7.23 (2H, d).

Step C:

Preparation of 4-(dicyclohexylmethoxy)benzyl bromide (8-5)

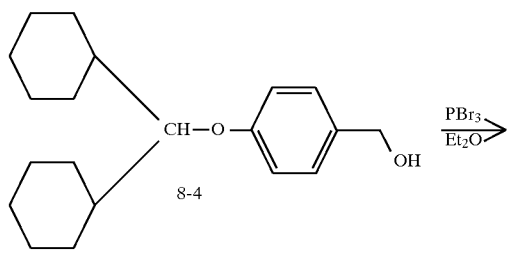

8-4 (1.93 g, 6.4 mmol) was converted to the bromide using phosphorus tribromide (1.69 g, 2.6 mmol) in ether (25 ml) as in Example 7. Recovered 8-5 liquid.

$^1$H NMR (CDCl$_3$) δ 1.0–1.32 (11H, m), 1.53–1.84 (11H, m), 3.91 (1H, t), 4.49 (2H, s), 6.85 (2H, d), 7.25 (2H, d).

Step D:

Preparation of 4-amino-1-[4-(dicyclohexylmethoxy)-benzyl]pyridinium bromide (8-7)

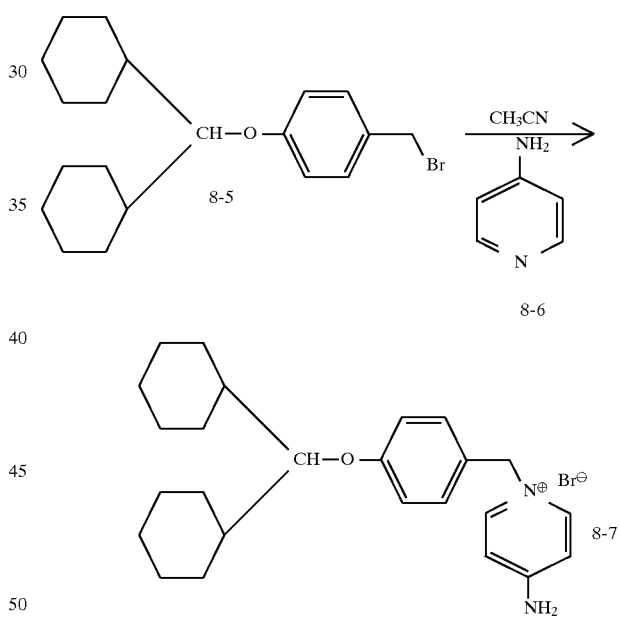

8-5 (183 mg, 0.5 mmol) and 4-aminopyridine 8-6 (47 mg, 0.5 mmol) were reacted in acetonitrile (4 ml) as in Example 1. Recovered white solid 8-7. mp: 248°–249° C.

$^1$H NMR (d$_6$-DMSO) δ 0.94–1.28 (11H, m), 1.5–1.75 (11H, m), 4.1 (1H, t), 5.24 (2H, s), 6.83 (2H, d), 6.98 (H, d), 7.28 (2H, d), 8.14 (2H, s), 8.3 (2H, d).

Analysis calculated for C$_{25}$H$_{35}$N$_2$OBr C, 65.35; H, 7.68; N, 6.10

Found: C, 65.45; H, 7.62; N, 6.17

EXAMPLE 9

Preparation of 3,4-diamino-1-(4-benzyloxybenzyl) pyridinium bromide (9-7)

Step A:
Preparation of 4-benzyloxybenzyl bromide (9-2)

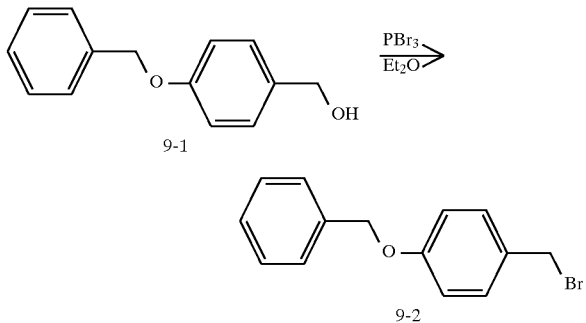

To a cold suspension of 4-benzyloxybenzyl alcohol 9-1 (21.4 g, 0.10 mol) in ether (250 ml) was added phosphorus tribromide (10.8 g, 40 mmol) as in Example 7. Recovered 27.2 g of white solid which was recrystallized from hexane (200 ml). Obtained pure bromide 9-2.
$^1$H NMR (CDCl$_3$) δ 4.5 (2H, s), 5.05 (2H, s), 6.94 (2H, d), 7.26–7.45 (7H, m).

Step B:
Preparation of 3,4-diamino-1-(4-benzyloxybenzyl)-pyridinium bromide (9-4)

9-2 (1.38 g, 5.0 mmol) was reacted with 3,4-diaminopyridine (9-3) (0.573 g, 5.25 mmol) in acetonitrile (50 ml) as in Example 1. Recovered white solid 9-4. Recrystallized from acetonitrile, mp: 240°–241° C.

$^1$H NMR (d$_6$-DMSO) δ 5.1 (2H, s), 5.25 (2H, s), 5.56 (2H, s), 6.74 (1H, d), 7.05 (2H, d), 7.24–7.46 (9H, m), 7.61 (1H, s), 7.96 (1H, d).

Analysis calculated for (C$_{19}$H$_{20}$N$_3$O$^+$Br$^-$): (0.25 Et$_2$O) C, 59.09; H, 5.22; N, 10.88

Found: C, 59.33; H, 5.60; N, 10.38

The compounds shown in the table below are exemplary compounds of the present invention. The range of Ki values associated with the specifically listed compounds is represented as follows:

| | |
|---|---|
| + | <0.1 μM |
| ++ | >0.1 μM and <1.0 μM |
| +++ | >1.0 μM |

TABLE I

| R | R$^1$ | Z | Y | R$^2$ | Ki (thr) μM | mp |
|---|---|---|---|---|---|---|
| PhCH$_2$O— | H | CH | CH | H | ++ | |
| Ph— | H | CH | CH | H | +++ | |

TABLE I-continued
| R | R¹ | Z | Y | R² | Ki (thr) $\mu M$ | mp |
|---|---|---|---|---|---|---|
| 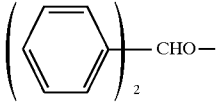 | H | N | CH | H | +++ | |
| 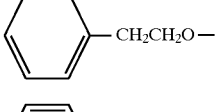 | H | CH | CH | H | + | 254–5° |
| 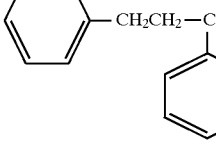 | H | CH | CH | H | ++ | 170–1° |
| 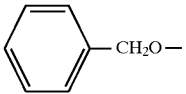 | H | CH | CH | H | ++ | 218.5–220° |
| 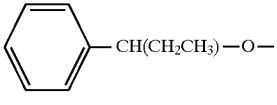 | H | CH | CH | H | + | 241–3° |
| 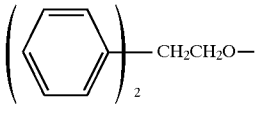 | H | CH | CH | H | ++ | 188–190° |
| 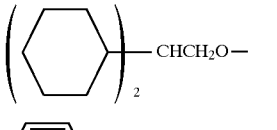 | H | CH | CH | H | ++ | 137–9° |
| 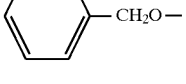 | H | CH | CH | H | ++ | 223–5° |
| 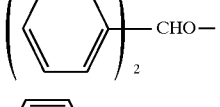 | H | CH | N | H | +++ | 212–4° |
| 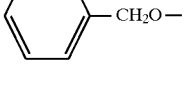 | H | CH | CH | H | ++ | 248–9° |
|  | —OCH₃ | CH | CH | H | +++ | 183–4° |

TABLE I-continued

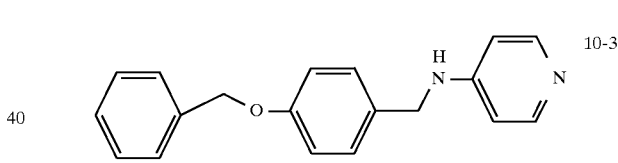

| R | R¹ | Z | Y | R² | Ki (thr) µM | mp |
|---|----|---|---|----|----|----|
| 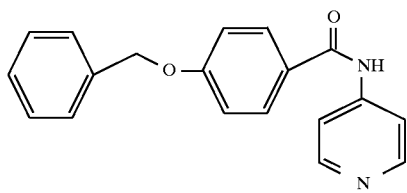 —CH₂O— | —OCH₂— <Ph> | CH | CH | H | +++ | 125–7° |
| 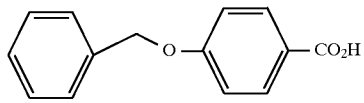 —CH₂O— | H | CH | CH | NH₂ | ++ | 240–1° |

The general procedure outlined in Scheme II can be used to make the following compounds.

EXAMPLE 10

Preparation of N-4-(4-benzyloxybenzyl) aminopyridine (10-3)

Step A:

<chemical structure 10-2>

Method 1
Preparation of 4-(4-benzyloxyphenyl) carboxamidopyridine (10-2)
A solution of <chemical structure 10-1>

(1.1 g, 4.8 mmol), 1-hydroxybenzotriazole (HOBT) (1.0 g, 7.4 mmol), 1-ethyl-3-(3-dimethylaminopropyl) carbodiimide.HCl (EDC) (1.4 g, 7.3 mmol), Et₃N (1 ml, 7.6 mmol) in DMF (40 ml) was treated under N₂ with 4-aminopyridine (4-AP) (0.54 g, 5.0 mmol). After stirring overnight at room temperature, the reaction was poured into saturated NaHCO3 and extracted with EtOAc (3×). The organic layers were washed with H₂O and brine, dried, filtered and concentrated to dryness. The residue was triturated with hexane to yield 10-2. mp: 126°–7° C.; ¹H NMR (CDCl₃) δ 5.15 (2H, s), 7.04 (2H, d), 7.4 (5H, m), 7.6 (2H, d), 7.84 (2H, d), 8.12 (1H, exch bs), 8.42 (2H, d).

Method 2:
Oxalyl chloride (3.3 g, 26 mmol) was added under N₂ dropwise to a suspension of 10-1 (5.0 g, 22 mmol) in CH₂Cl₂ (75 ml) with 4 drops of DMF. After 1 h the solution was concentrated to dryness and flushed once with CHCl₃. The residue was dissolved in CHCl₃ (60 ml) and added dropwise to a suspension of 4-AP (6.2 g, 66 mmol) in CHCl₃ (100 ml). After 1 h at room temperature the solution was poured into saturated Na₂CO₃ and separated. The aqueous was further extracted with EtOAc (3×). The combined extracts were dried, filtered and concentrated to dryness. The residue was chromatographed on a Still column (80 mm) and the product eluted with 10% CH₃OH—CHCl₃ to yield 10-2.

<chemical structure 10-3>

Preparation of 10-3:
A solution of 10-2 (3.5 g, 11.5 mmol) in THF (40 ml) was treated dropwise under N₂ with 1.0M LAH in THF (17 ml, 17 mmol). After addition, the solution was heated at 60° C. After 18 h, the solution was treated with saturated Na₂SO₄ to a white suspension. The mixture was filtered and the pad washed with EtOAc (200 ml). The organic extracts were washed with saturated Na₂CO₃, dried, filtered and concentrated to dryness to yield 10-3. An analytical sample was crystallized as the HCl salt from EtOH—Et₂O; mp: 224°–6° C.;
¹H NMR (d₆-DMSO) δ 4.45 (2H, s), 5.1 (2H, s), 6.95 (4H, d and m), 7.4 (7H, m), 8.2 (2H, d), 9.2 (1H, exch bs).
Analysis calculated for C₁₉H₁₈N₂O—HCl.0.25 H₂O C, 68.87; H, 5.93; N, 8.46
Found: C, 68.49; H, 5.80; N, 8.25

EXAMPLE 11

Preparation of N-4-(1,1-diphenylmethoxy) benzylaminopyridine (11-1)

The desired compound was prepared as described in Example 10 using Method 1 in Step A and then Step B; mp: 220°–1° (EtOH.Et₂O);
¹H NMR (d₆-DMSO) δ 3.4 (1H, exch bs), 4.4 (2H, s), 6.5 (1H, s), 6.9 (2H, dd), 7.05 (2H, d), 7.6 (8H, m), 7.5 (4H, d), 8.15 (2H, dd), 9.1 (1H, exch t).

Analysis calculated for C$_{25}$H$_{22}$N$_2$O.HCl.¾ H$_2$O C, 72.10; H, 5.93; N, 6.75
Found: C, 72.35; H, 5.71; N, 6.97

EXAMPLE 12

Preparation of N-4-(cyclohexylmethoxy) benzylaminopyridine (12-1)

The desired compound was prepared as described for 10-3 in Example 10 using Method 1 in Step A and then Step B; mp: 273°–4° C. (EtOH);
$^1$H NMR (d$_6$-DMSO) δ 1.1 (5H, m), 1.7 (6H, m), 3.75 (2H, s), 4.45 (2H, s), 6.9 (4H, bd), 7.28 (2H, bd), 8.15 (2H, bd), 9.25 (1H, exch bs).
Analysis calculated for C$_{19}$H$_{24}$N$_2$O.HCl C 68.55, H 7.57, N 8.42
Found: C 68.35, H 7.53, N 8.33

EXAMPLE 13

Preparation of 4-[4-(2-methyl-1-phenylpropoxy) benzylamino]pyridine (13-2)

Step A:
Preparation of 1-phenyl-2-methyl-1-propanol (13-2)

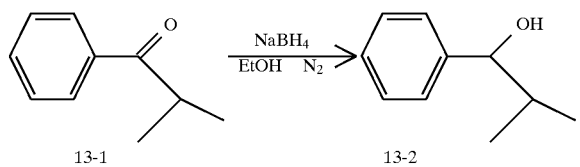

Isobutyrophenone 13-1 (29.6 g, 0.20 mmol) was dissolved in ethanol (300 ml) and was reduced under N$_2$ with sodium borohydride (7.57 g, 0.20 mmol) for 4 hrs. at room temperature. The ethanol was removed in vacuo and the residue was taken up in ethyl acetate (200 ml) and water (100 ml). The ethyl acetate extract was washed with water, dried, filtered and concentrated in vacuo to obtain alcohol 13-2.
$^1$H NMR (CDCl$_3$): δ 0.82 (3H, d), 1.0 (3H, d), 1.83 (1H, s), 2.0 (1H, m), 4.4 (1H, d), 7.26 (5H, m).

Step B:
Preparation of ethyl 4-(2-methyl-1-phenylpropoxy) benzoate (13-5)

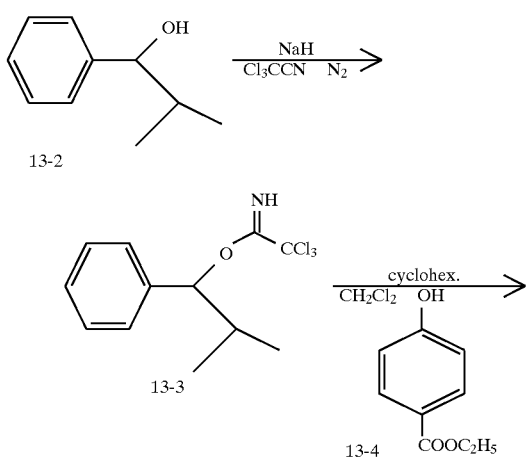

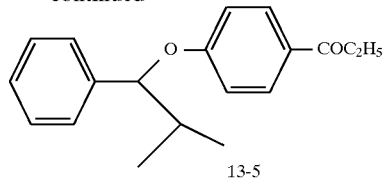

Sodium hydride (60% in mineral oil) (200 mg, 5 mmol) was washed with hexane under nitrogen and was suspended in anhydrous ether (30 ml). To the stirred suspension was added 13-2 (7.5 g, 50 mmol) in ether (10 ml) and the mixture was stirred at RT for ½ hr. After cooling to −5° C., trichloroacetonitrile (7.58 g, 52.5 mmol) was added. Stirring was continued for ½ hr. at 0° C. and at ambient temperature for 1 hr. The ether was removed in vacuo and the residual oil 13-3 was taken up in cyclohexane (20 ml) and methylene chloride (10 ml). To this solution was added ethyl 4-hydroxybenzoate (13-4) (8.3 g, 50 mmol) followed by methylene chloride (25 ml) and trifluoromethanesulfonic acid (0.2 ml). The mixture was stirred at ambient temperature overnight and was filtered and concentrated to an oil. Chromatography on silica gel gave 13-5.

$^1$H NMR (CDCl$_3$) δ 0.91 (3H, d), 1.05 (3H, d), 1.32 (3H, t), 2.15 (1H, m), 4.3 (2H, q), 4.88 (1H, d), 6.83 (2H, d), 7.2–7.4 (5H, m), 8.7 (2H, d).

Step C:

Preparation of 4-(2-methyl-1-phenylpropoxy)benzoic acid (13-6)

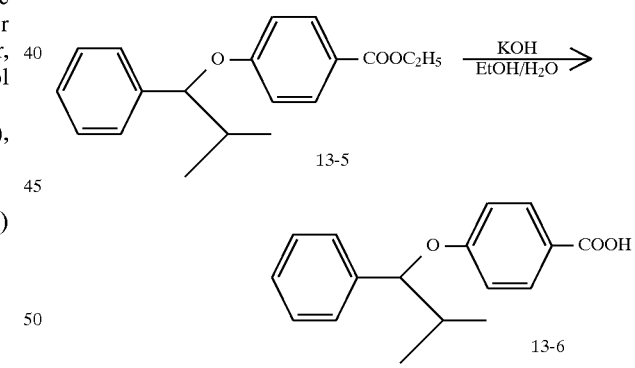

To 13-5 (8.89 g, 29.8 mmol) was added 2N potassium hydroxide (100 ml) and ethanol (50 ml). The mixture was stirred at 100° C. overnight. The ethanol was removed in vacuo and the aqueous solution was cooled in ice and acidified with 6N HCl (35 ml, 0.21 mol). The acid was extracted into ethyl acetate (50 ml) and the extract was washed with water, dried, filtered and concentrated in vacuo to obtain the oil 13-6, which solidified. The white solid melted at 125°–129° C.

$^1$H NMR (CDCl$_3$) δ 0.91 (3H, d), 1.05 (3H, d), 2.15 (1H, m), 4.9 (1H, d), 6.85 (2H, d), 7.2–7.35 (5H, m), 7.91 (2H, d).

Step D:

Preparation of 4-(2-methyl-1-phenylpropoxy)benzoyl chloride (13-7)

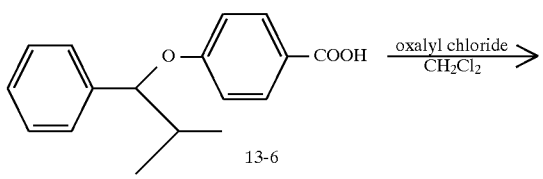

13-6 (0.541 g, 2.0 mmol) was stirred in methylene chloride (3 ml) at room temperature and oxalyl chloride (0.381 g, 3.0 mmol) was added. After 3 hrs. at room temperature the solution was concentrated in vacuo to a pale yellow liquid 13-7. The acid chloride was used without purification.

Step E:

Preparation of 4-(2-methyl-1-phenylpropoxy)-N-(4-pyridyl)benzamide (13-9)

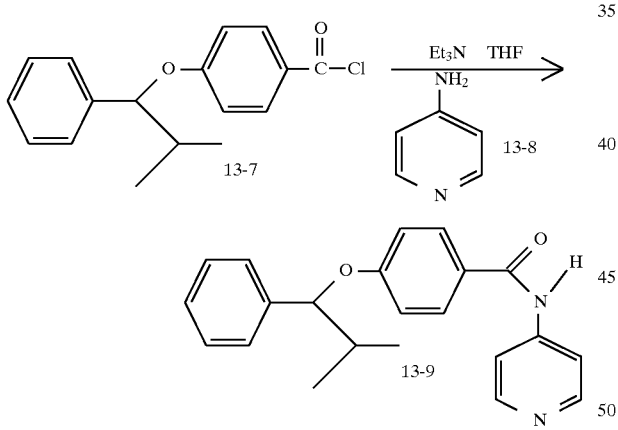

To an ice cold stirred solution of 13-8 (0.188 g, 2.0 mmol) and triethylamine (0.233 g, 2.0 mmol) in tetrahydrofuran (10 ml) was added a solution 13-7 (0.54 g, 2.0 mmol) over a 5-10 min period. The reaction was stirred at ambient temperature overnight. Then the THF was removed in vacuo and the residue was taken up in ethyl acetate (50 ml) and water (25 ml). The ethyl acetate extract was separated, washed with water, dried and concentrated in vacuo to yield the oil 13-9.

$^1$H NMR (d$_6$-DMSO) δ 0.84 (3H, d), 1.02 (3H, d), 2.12 (1H, m), 5.2 (1H, d), 7.0 (2H, d), 7.2–7.4 (5H, m), 7.72 (2H, d), 7.82 (2H, d), 8.42 (2H, d), 10.33 (1H, s).

Step F:

Preparation of 4-[4-(2-methyl-1-phenylpropoxy)-benzylamino]pyridine (13-10)

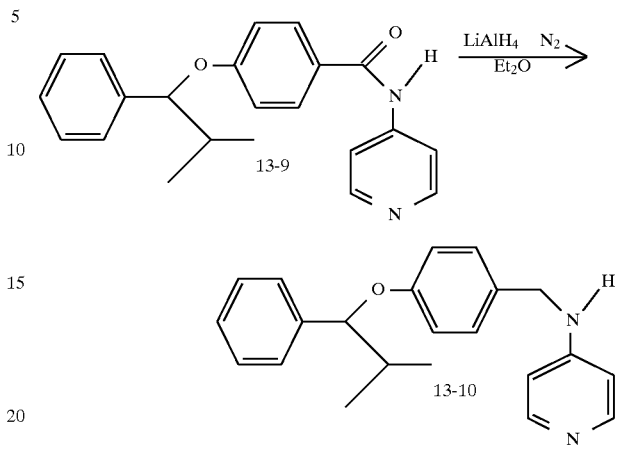

To a stirred suspension of lithium aluminum hydride (0.152 g, 4.0 mmol) in ether (5 ml) under nitrogen was added a solution of 13-9 (0.71 g, 2.0 mmol) in tetrahydrofuran (5 ml) over a 5 min period. The mixture was stirred at ambient temperature overnight and then was decomposed by adding water and sodium hydroxide. Ethyl acetate (25 ml) was added and the mixture was filtered. The filtrate was dried, filtered and concentrated in vacuo to 620 mg of colorless oil which was chromatographed on silica gel. 13-10 was obtained as an oil. The hydrochloride salt melted at 186°–188° C.

$^1$H NMR (d$_6$-DMSO) δ 0.5 (3H, d), 0.99 (3H, d), 1.16 (1H, t), 4.15 (2H, d), 4.99 (1H, d), 6.47 (2H, d), 6.82 (2H, d), 7.05 (1H, t), 7.12 (2 H, d), 7.2–7.25 (1H, m), 7.25–7.36 (4H, m), 7.96 (2H, d).

Analysis calculated for (C$_{22}$H$_{24}$N$_2$O.HCl.0.2 H$_2$O) C, 70.93; H, 6.87; N, 7.52

Found: C, 70.99; H, 6.79; N, 7.62

EXAMPLE 14

Preparation of 4-[4-(2,2-diphenylethoxy)benzylamino]pyridine (14-7)

Step A:

Preparation of ethyl 4-(2,2-diphenylethoxy)benzoate (14-3)

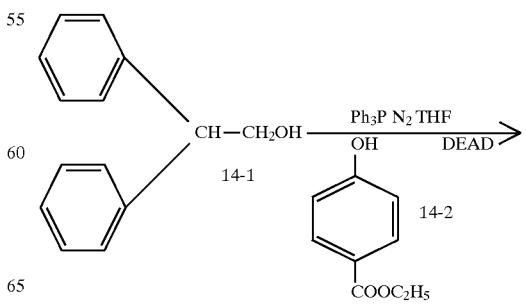

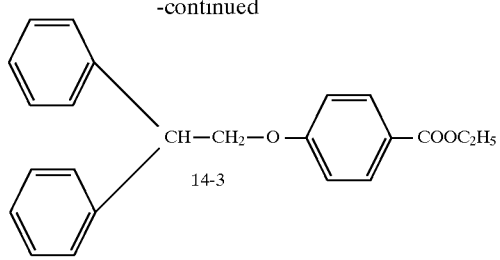
14-3

To 2,2-diphenylethanol (14-1) (5.95 g, 30 mmol) was added ethyl 4-hydroxybenzoate (14-2) (5.40 g, 30 mmol), triphenylphosphine (8.66 g, 33 mmol) and tetrahydrofuran (125 ml). The mixture was cooled in ice and diethyl azodicarboxylate (5.75 g, 33 mmol) was added. The reaction mixture was stirred under nitrogen at ambient temperature overnight and then the volatile components were removed in vacuo. The oil-solid residue was taken up in ethyl acetate (100 ml) and water (50 ml). Work up of the ethyl acetate portion give crude solid. The product 14-3 was purified by silica gel chromatography.

$^1$H NMR (CDCl$_3$) δ 1.37 (3H, t), 4.33 (2H, q), 4.52 (3H, s), 6.9 (2H, d), 7.4–7.66 (10H, m), 7.96 (2H, d).

Step B:

Preparation of 4-(2,2-diphenylethoxy)benzoic acid (14-4)

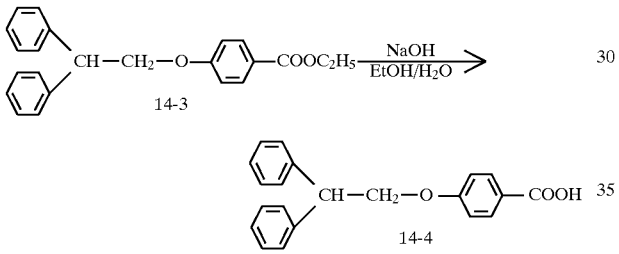

A suspension of 14-3 (346 mg, 1.0 mmol) in 10% aqueous sodium hydroxide (15 ml) and ethanol (5 ml) was stirred at 100° C. overnight. The resulting solution was cooled and acidified with excess HCl. A gum separated which was extracted into ethyl acetate (15 ml), washed with water, dried, filtered and concentrated in vacuo. The acid 14-4 was a pale yellow solid, mp: 140°–146° C.

$^1$H NMR (CDCl$_3$) δ 4.55 (3H, s), 6.94 (2H, d), 7.21–7.37 (10H, m), 8.04 (2H, d).

Step C:

Preparation of 4-(2,2-diphenylethoxy)-N-(4-pyridyl)benzamide (14-6)

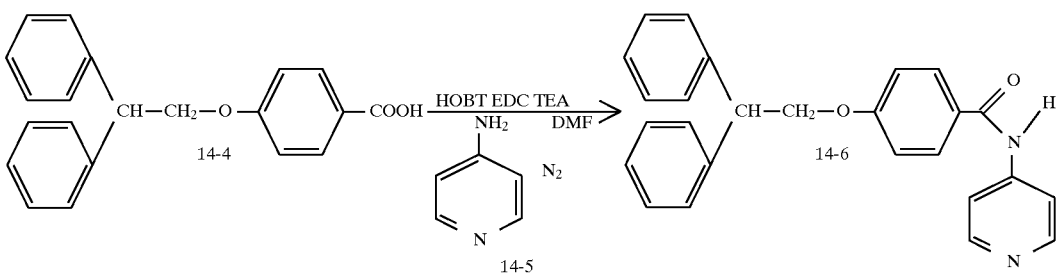

To 14-4 (125 mg, 0.393 mmol), 4-aminopyridine (14-5) (56 mg, 0.59 mmol), 1-hydroxybenzotriazole hydrate (80 mg, 0.59 mmol) and triethylamine (60 mg, 0.59 mmol) in DMF (5 ml) under nitrogen was added 1-ethyl-3-(3-dimethylamino-propyl)carbodiimide hydrochloride (113 mg, 0.59 mmol). The mixture was stirred at ambient temperature overnight and the DMF was removed under high vacuum. The residual oil was taken up in ethyl acetate (15 ml) and washed with water and saturated sodium chloride, dried, filtered and concentrated to an amber gum 14-6.

Step D:

Preparation of 4-[4-(2,2-diphenylethoxy)benzylamino]pyridine (14-7)

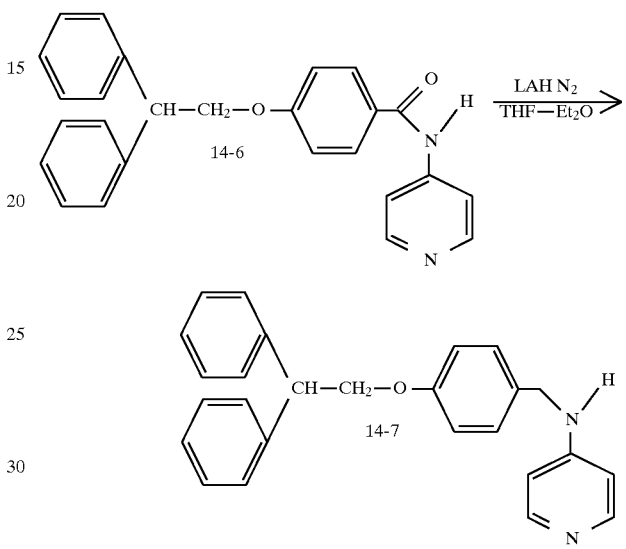

To a solution of 14-6 (0.144 g, 0.365 mmol) in tetrahydrofuran (1 ml) and ether (3 ml) under nitrogen was added lithium aluminum hydride (30 mg, 0.79 mmol). The mixture was stirred at room temperature overnight and then was decomposed with water and sodium hydroxide. The mixture was filtered and concentrated in vacuo to a colorless oil 14-7 which was purified by silica gel chromatography and converted to the HCl salt, mp: 213°–214.5° C.

$^1$H NMR (d$_6$-DMSO) δ 3.36 (1H, s), 4.36–4.58 (6H, d, m), 6.84–7.0 (3H, d, bm), 7.16–7.4 (11H, m), 8.06–8.25 (2H, d), 9.08–9.24 (1H, bs).

Analysis calculated for (C$_{22}$H$_{24}$N$_2$O.HCl) C, 74.48; H, 6.10; N, 6.74

Found: C, 74.89; H, 6.04; N, 6.72

EXAMPLE 15

Preparation of 4-[4-(2-cyclohexylethoxy)benzylamino]pyridine (15-8)

Step A:

Preparation of ethyl 4-(2-cyclohexylethoxy)benzoate (15-3)

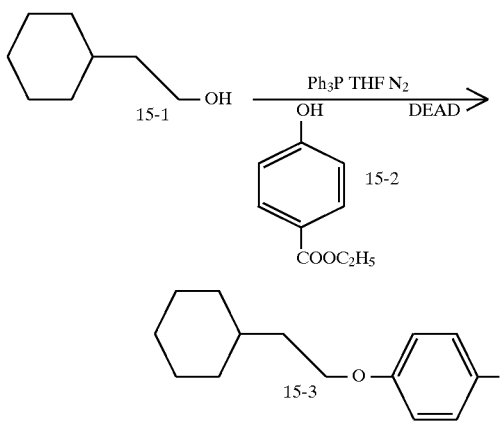

2-Cyclohexylethanol 15-1 (3.2 g, 25 mmol) and ethyl 4-hydroxybenzoate 15-2 (4.15 g, 25 mmol) were reacted as in Example 14. The product 15-3 was obtained as a waxy solid.
$^1$H NMR (CDCl$_3$) δ 1.04 (2H, m), 1.08–1.3 (3H, m), 1.39 (3H, t), 1.42–1.58 (1H, m), 1.62–1.81 (7H, m), 4.04 (2H, t), 4.35 (2H, q), 6.9 (2H, d), 7.98 (2H, d).

Step B:

Preparation of 4-(2-cyclohexylethoxy)benzoic acid (15-4)

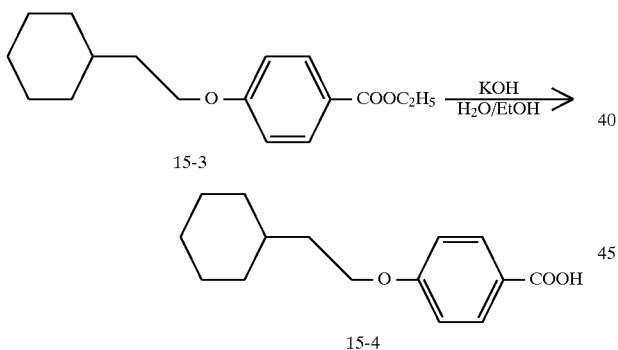

Hydrolysis of 15-3 (1.13 g, 3.1 mmol) as in Example 14 gave the acid 15-4 as a white solid. mp, 129°–132° C.
$^1$H NMR (CDCl$_3$) δ 0.9–1.07 (2H, m), 1.08–1.36 (3H, m), 1.43–1.6 (1H, m), 1.6–1.82 (7H, m), 4.06 (2H, t), 6.92 (2H, d), 8.03 (2H, d).

Step C:

Preparation of 4-(2-cyclohexylethoxy)benzoyl chloride (15-5)

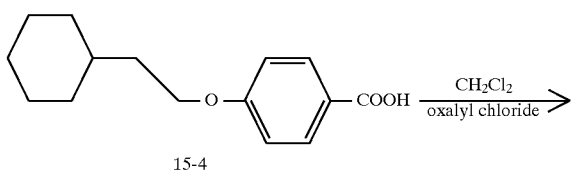

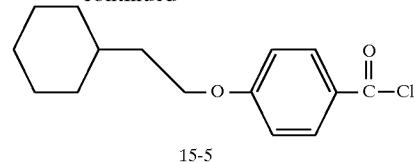

The acid chloride was prepared from 15-4 (0.497 g, 2 mmol) as in Example 13. Crude product was obtained as an oil in quantitative yield and was used without further purification.

Step D:

Preparation of 4-(2-cyclohexylethoxy)-N-(4-pyridyl)-benzamide (15-7)

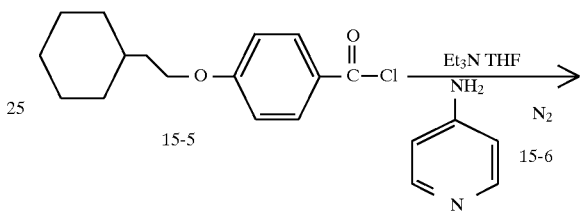

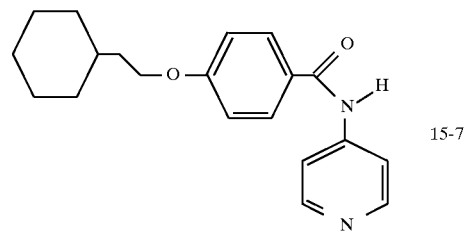

This amide was prepared from 15-5 (0.53 g, 2 mmol) and 4-aminopyridine (15-6) (0.188 g, 2 mmol) as in Example 13. The solid obtained, 15-7, melted at 123°–125° C.

$^1$H NMR (d$_6$-DMSO) δ 0.88–1.03 (2H, m), 1.05–1.3 (3H, m), 1.4–1.56 (1H, m), 1.56–1.8 (7H, m), 4.1 (2H, t), 7.08 (2H, d), 7.78 (2H, d), 7.95 (2H, d), 8.45 (2H, d), 10.42 (1H, s).

Step E:

Preparation of 4-[4-(2-cyclohexylethoxy)-benzylamino]pyridine (15-8)

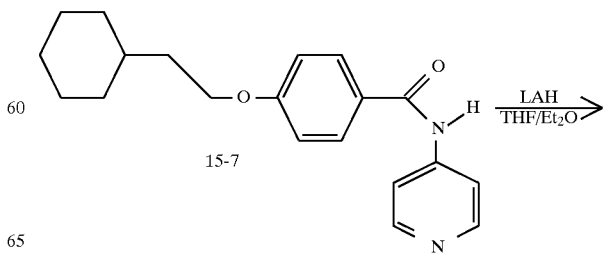

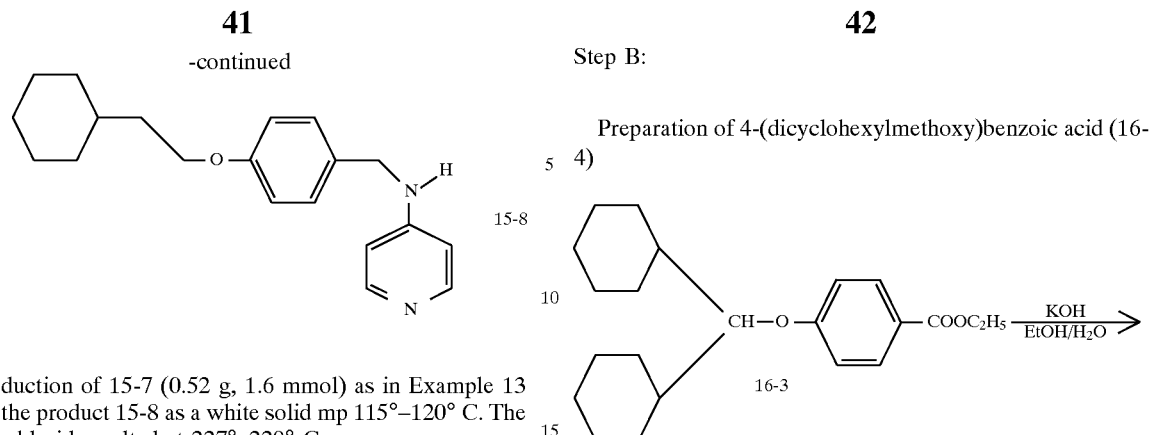

Reduction of 15-7 (0.52 g, 1.6 mmol) as in Example 13 gave the product 15-8 as a white solid mp 115°–120° C. The hydrochloride melted at 227°–229° C.

$^1$H NMR (d$_6$-DMSO) δ 0.81–1.0 (3H, m), 1.02–1.3 (3H, m), 1.37–1.52 (1H, m), 1.53–1.78 (7H, m), 3.95 (2H, t), 4.43 (2H, d), 6.91 (2H, d), 6.82–7.04 (2H, m), 7.28 (2H, d), 8.15 (2H, d), 9.25 (1H, t);

Analysis calculated for C$_2$OH$_{26}$N$_2$O.HCl C, 69.24; H, 7.58; N, 8,08

Found: C, 69.16; H, 7.80; N, 8.08

EXAMPLE 16

Preparation of 4-[4-(dicyclohexylmethoxy)-benzylamino]pyridine (16-8)

Step A:

Preparation of ethyl 4-(dicyclohexylmethoxy)benzoate (16-3)

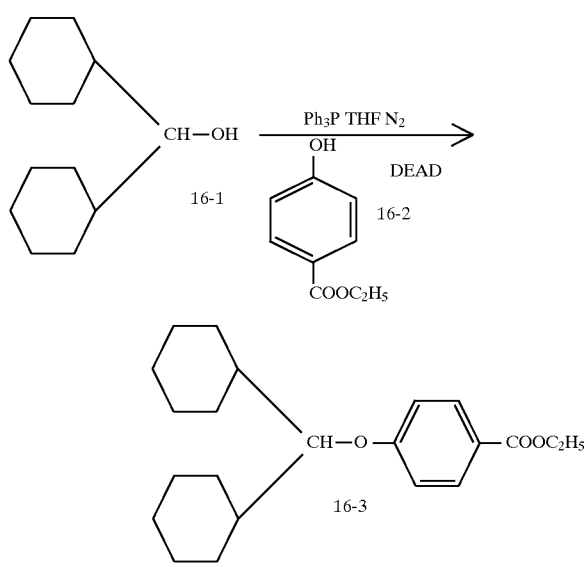

Dicyclohexylmethanol (16-1) (6.97 g, 35.5 mmol) andl ethyl 4-hydroxybenzoate (16-2) (5.9 g, 35.5 mmol) were reacted as in Example 14 and the product 16-3 was isolated as a colorless oil.

$^1$H NMR (CDCl$_3$) δ 0.98–1.3 (11H, m), 1.35 (3H, t), 1.52–1.86 (11H, m), 4.02 (1H, t), 4.33 (2H, q), 6.91 (2H, d), 7.94 (2H, d).

Step B:

Preparation of 4-(dicyclohexylmethoxy)benzoic acid (16-4)

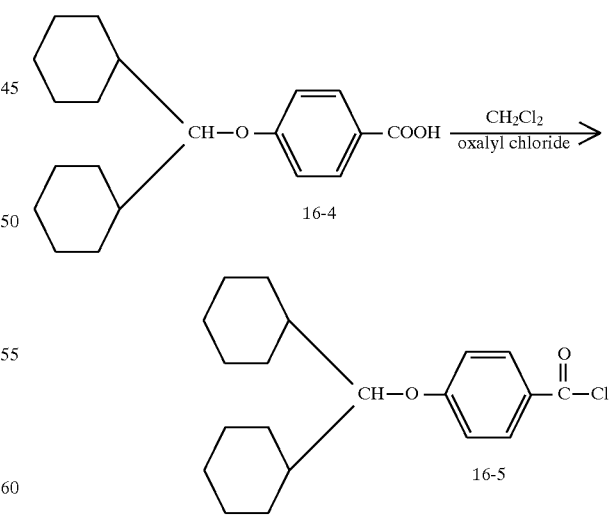

Hydrolysis of 16-3 (7.9 g, 23 mmol) as in Example 14 produced slightly crude acid 16-4.

$^1$H NMR (CDCl$_3$) δ 0.98–1.32 (11H, m), 1.54–1.84 (11H, m), 4.05 (1H, t), 6.92 (2H, d), 8.0 (2H, d).

Step C:

Preparation of 4-(dicyclohexylmethoxy)benzyl chloride (16-5)

Preparation of the acid chloride of 16-4 (1.54 g, 5 mmol) as in Example 13 gave the product 16-5 as a pale yellow oil. It was used without purification.

Step D:
Preparation of 4-(4-dicyclohexylmethoxy)-N-(4-pyridyl)benzamide (16-7)

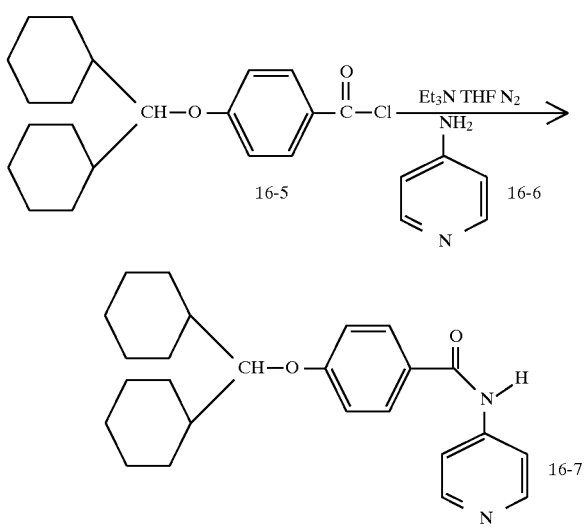

4-Aminopyridine 16-6 (0.47 g, 5 mmol) was acylated with 4-(dicyclohexylmethoxy)benzyl chloride 16-5 (5 mmol) as in Example 13 to give the amide 16-7 as a white solid.
$^1$H NMR (d$_6$-DMSO) δ 0.97–1.3 (11H, m), 1.53–1.76 (11H, m), 4.25 (1H, t), 7.1 (2H, d), 7.76 (2H, d), 7.88 (2H, d), 8.43 (2H, d), 10.38 (1H, s).

Step E:
Preparation of 4-[4-(dicyclohexylmethoxy)-benzylamino]pyridine (16-8)

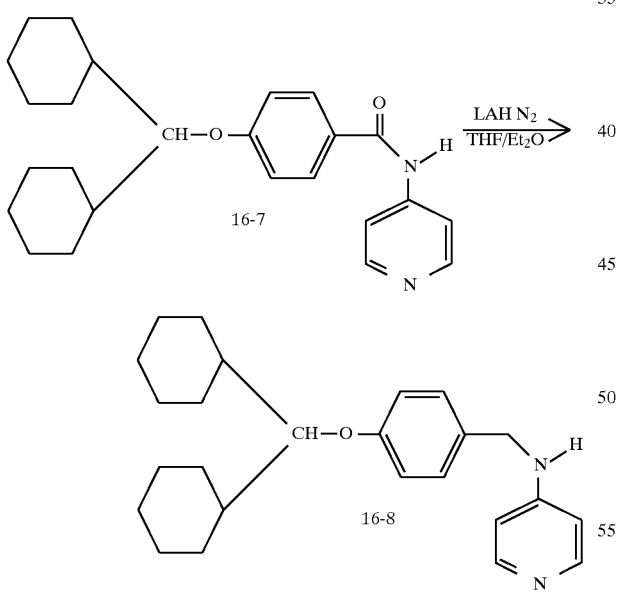

Lithium aluminum hydride reduction of 16-7 (1.28 g, 3.3 mmol) as in Example 14 gave product 16-8 as a colorless oil. The hydrochloride melted at 213°–215° C.
$^1$H NMR (d$_6$-DMSO) δ 0.93–1.28 (11H, m), 1.5–1.77 (11H, m), 4.04 (1H, t), 4.41 (2H, d), 6.95 (4H, d), 7.22 (2H, d), 8.16 (2H, bd), 9.15 (1H, t).
Analysis calculated for C$_{25}$H$_{34}$N$_2$O·HCl C, 72.35; H, 8.50; N, 6.75
Found: C, 72.63; H, 8.47; N, 6.76

EXAMPLE 17

Preparation of 4-[4-(1,3-diphenyl-2-propoxy)benzylamino]pyridine (17-9)

Step A:
Preparation of 1,3-diphenyl-2-propanol (17-2)

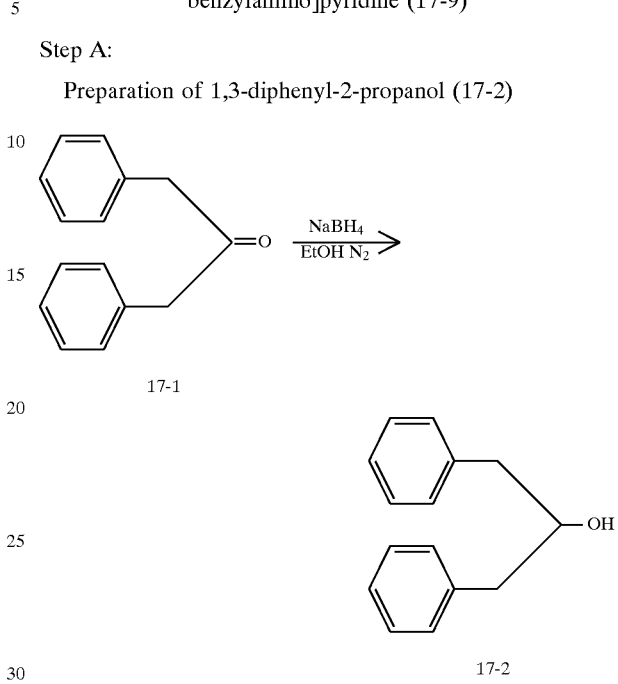

Reduction of 1,3-diphenylacetone 17-1 (21.0 g, 0.10 mole) was accomplished as in Example 13 in quantitative yield. The alcohol 17-2 was a colorless oil.
$^1$H NMR (CDCl$_3$) δ 1.64 (1H, d), 2.71–2.91 (4H, dd), 4.07 (1H, m), 7.18–7.37 (10H, m).

Step B:
Preparation of ethyl 4-(1,3-diphenyl-2-propoxy)benzoate (17-4)

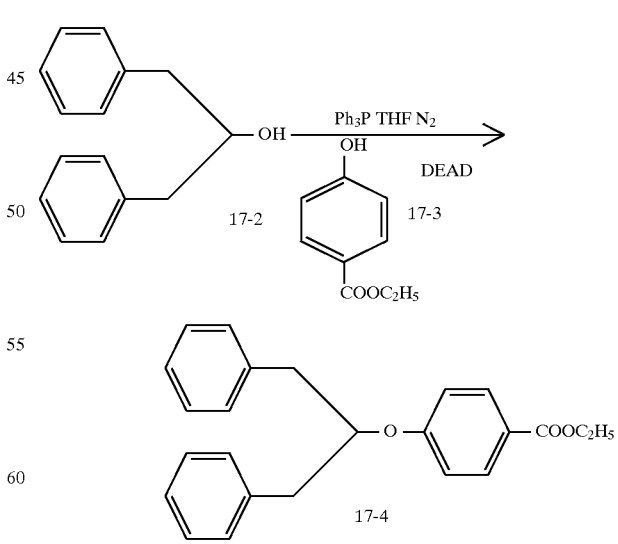

Reaction of 17-2 (5.3 g, 0.025 mol) and ethyl 4-hydroxybenzoate 17-2 (6.56 g, 0.025 mol) as in Example 14 gave the product 17-4 as a colorless oil.

Step C:
Preparation of 4-(1,3-diphenyl-2-propoxy)benzoic acid (17-5)

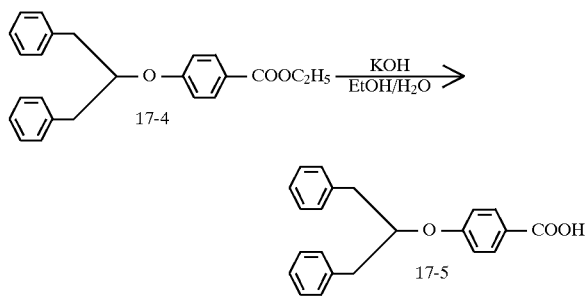

Hydrolysis of 17-4 (7.47 g, 21 mmol) as in Example 14 gave the acid 17-5 as a viscious oil (4.28 g).
$^1$H NMR (CDCl$_3$) δ 2.91–3.08 (4H, m), 4.77 (1H, m), 6.84 (2H, d), 7.16–7.33 (10H, m), 7.96 (2H, d).

Step D:
Preparation of 4-(1,3-diphenyl-2-propoxy)benzoyl chloride (17-6)

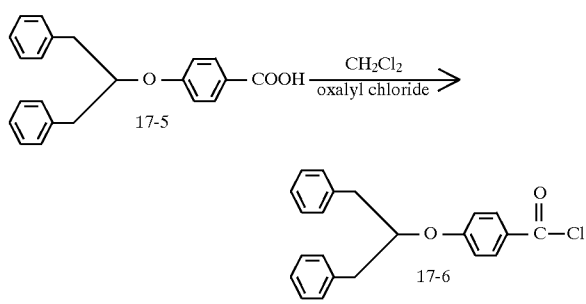

17-5 (1.66 g, 5 mmol) was converted to the acid chloride 17-6 as in Example 13. The viscous oil was used without further purification.

Step E:
Preparation of 4-(1,3-diphenyl-2-propoxy)-N-(4-pyridyl)benzamide (17-8)

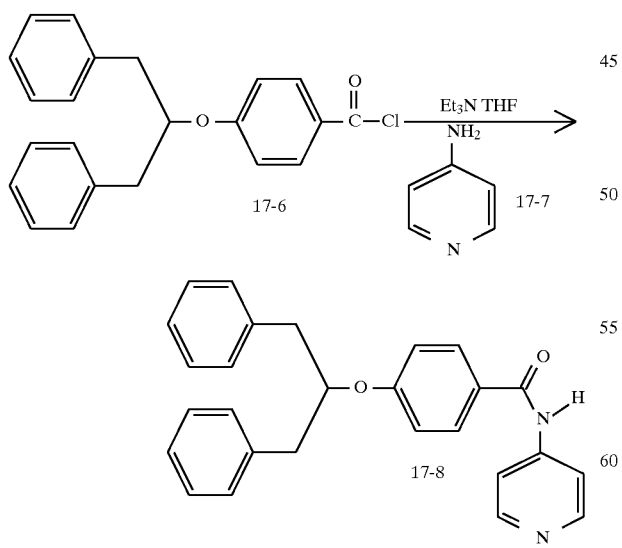

4-Aminopyridine 17-7 (0.471 g, 5 mmol) was acylated with 17-6 (1.75 g, 5 mmol) using the conditions of Example 13. The amide 17-8 was obtained as a solid foam.

Step F:
Preparation of 4-[4-(1,3-diphenyl-2-propoxy)-benzylamino]pyridine (17-9)

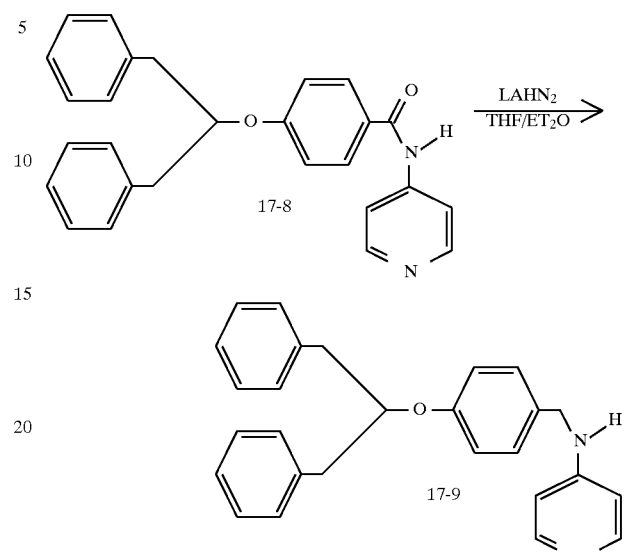

Lithium aluminum hydride reduction of 17-8 (1.36 g, 3.3 mmol) as described in Example 14 gave a quant. yield of the product 17-9 as a viscous oil. The hydrochloride melted at 151°–154° C.
$^1$H NMR (d$_6$-DMSO) δ 2.88 (4H, d), 4.41 (2H, d), 4.73 (1H, m), 6.9 (2H, d), 6.83–7.0 (2H, m), 7.16–7.82 (12H, m), 9.15 (2H, bd), 9.15 (1H, t).
Analysis calculated for C$_{27}$H$_{26}$N$_2$O.HCl.0.4 H$_2$O C, 74.00; H, 6.40; N, 6.39
Found: C, 73.94; H, 6.28; N, 6.30

EXAMPLE 18

Preparation of 4-[4-(3,4-methylenedioxybenzyloxy)benzylamino]pyridine (18-7)

Step A:
Preparation of ethyl 4-(3,4-methylenedioxybenzyloxy)benzoate (18-3)

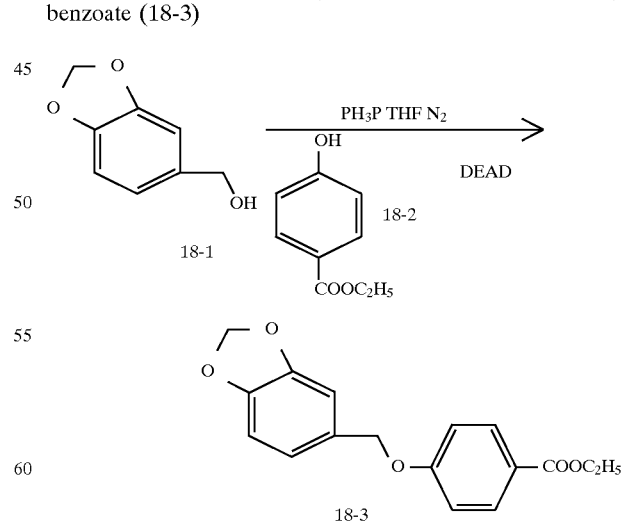

3,4-Methylenedioxybenzyl alcohol 18-1 (6.2 g, 40.0 mmol) and ethyl 4-hydroxybenzoate 18-2 (6.65 g, 40.0 mmol) were reacted as in Example 14. The desired ester 18-3 was obtained as a white solid.

Step B:
Preparation of ethyl 4-(3,4-methylenedioxybenzyloxy) benzoic acid (18-4)

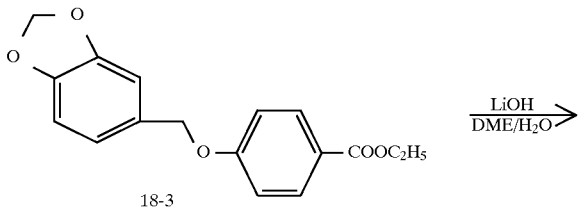

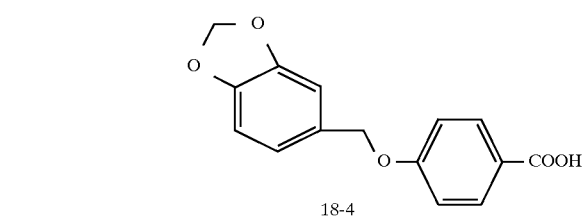

18-3 (2.5 g, 8.3 mmol) was hydrolyzed with lithium hydroxide (0.8 g, 33.4 mmol) in dimethoxyethane (60 ml) and water (30 ml) at room temperature overnight. Then water (50 ml) was added and the solution was acidified with 6N HCl. Filtered the white solid which had precipitated and obtained a quantitative yield of crude acid which was recrystallized from butyl chloride-ethyl acetate. The pure products 18-4 melted at 192°–194° C.
$^1$H NMR ($d_6$-DMSO) δ 5.06 (2H, s), 6.02 (2H, s), 6.9–6.99 (2H, m), 7.02–7.12 (3H, m), 7.9 (2H, d).

Step C:
Preparation of 4-(3,4-methylenedioxybenzyloxy)-N-(4-pyridyl)benzamide (18-6)

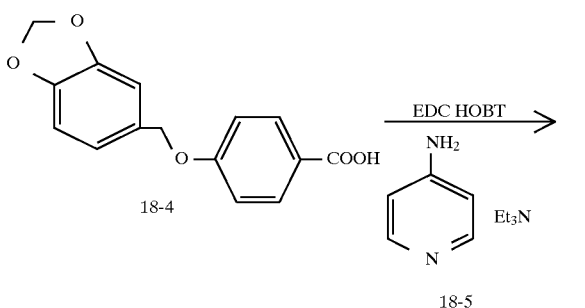

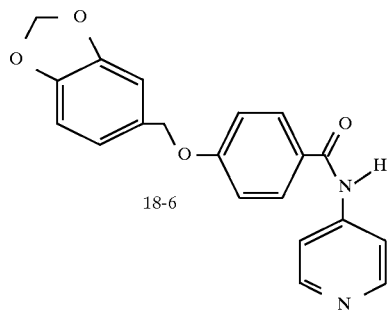

To 18-4 (0.545 g, 2 mmol) was added 4-aminopyridine 18-5 (0.235 g, 2.5 mmol), 1-hydroxy-benzotriazole hydrate (0.338 g, 2.5 mmol), 1-ethyl-3-(3-dimethyl-aminopropyl) carbodiimide (0.479 g, 2.5 mmol) and dry DMF (5 ml) followed by triethylamine (0.35 ml, 2.5 mmol). The mixture was stirred at ambient temperature overnight. Then the DMF was removed under high vacuum. The residual oil was chromatographed on silica gel to obtain a white solid 18-6.

Step D:
Preparation of 4-[4-(3,4-methylenedioxybenzyloxy) benzylamino]pyridine (18-7)

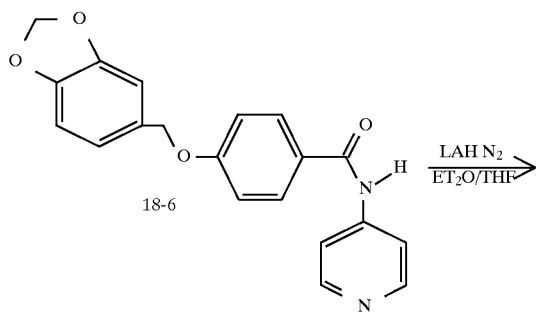

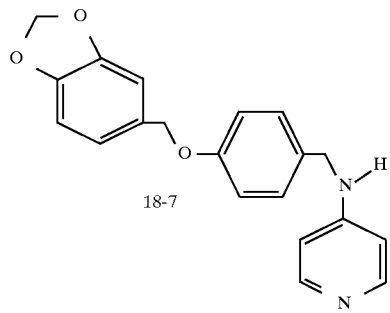

18-6 (0.32 g, 0.9 mmol) was reduced with lithium aluminum hydride (0.30 g, 8 mmol) as in Example 10. The product 18-7 was obtained as an oil. The hydrochloride salt melted at 190°–193° C.

$^1$H NMR ($d_6$-DMSO) δ 4.45 (2H, d), 4.99 (2H, s), 6.02 (2H, s), 6.83–7.06 (7H, m), 7.3 (2H, d), 8.16 (2H, bd), 9.2 (1H, t).

Analysis calculated for $C_{20}H_{18}N_2O_3 \cdot HCl \cdot 0.2\ H_2O$ C 64.15, H 5.22, N 7.48

Found: C 63.82, H 5.16, N 7.51.

The compounds shown in the table below are exemplary compounds of the present invention. The range of Ki values associated with the specifically listed compounds is represented as follows:

| | |
|---|---|
| + | <0.1 μM |
| ++ | >0.1 μM and <1.0 μM |
| +++ | >1.0 μM |

TABLE 2

Structure: R-CH(R¹)-X-[phenyl]-CH₂-NH-[4-pyridyl]

| R | R¹ | X | Ki (thr) μM | mp (HCl) |
|---|---|---|---|---|
| phenyl | H | O | +++ | 224–6° |
| phenyl | phenyl | O | +++ | 220–1° |
| cyclohexyl | H | O | +++ | 273–4° |
| (phenyl)₂CH— | H | O | +++ | 213–14.5° |
| phenyl | (CH₃)₂CH— | O | +++ | 186–8° |
| cyclohexyl-CH₂— | H | O | +++ | 227–8° |
| cyclohexyl | cyclopropyl | O | ++ | — |
| cyclohexyl | cyclohexyl | O | +++ | 213–5° |
| phenyl-CH₂— | phenyl-CH₂— | O | +++ | 151–4° |
| benzo[1,3]dioxol-5-yl | H | O | +++ | 190–3° |
| phenyl | H | S | +++ | 211–3° |
| cyclohexyl | H | NH | +++ | 202–5° |
| (cyclohexyl)₂CH— | H | O | +++ | 171–3° |

TABLE 2-continued

| R | R¹ | X | Ki (thr) µM | mp (HCl) |
|---|---|---|---|---|
| phenyl | H | NH | +++ | 200–2° |
| phenyl | —CO₂CH₂ | O | +++ | 182–5° |
| phenyl | —C(O)NH₂ | O | +++ | — |
| cyclohexyl | phenyl | O | +++ | 176–182° |
| cyclohexyl-CH₂-CH₂CH₂ | H | O | +++ | 101–2° (freebase) |
| benzodioxole-CH₂ | H₃C-CH(CH₃)- | O | +++ | 210–11° |
| phenyl | CH₂CH₂— | O | +++ | 163–4° |
| phenyl | CH₃— | O | +++ | 128–30° |

EXAMPLE 19

Preparation of 4'-(4-cyclohexylmethyloxy-2-benzylphenylmethyl)-aminopyridine (19-3)

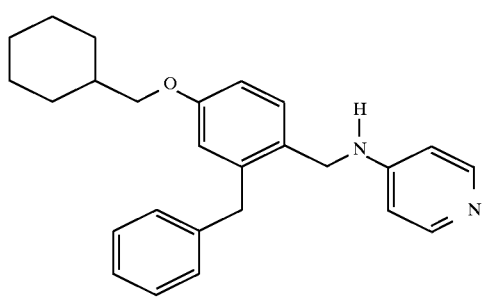

Step 2 A:
Preparation of 4-cyclohexylmethyloxy-2-benzyl-benzoic acid (19-2)

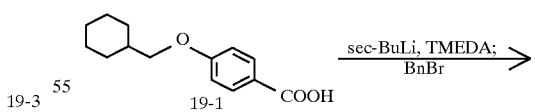

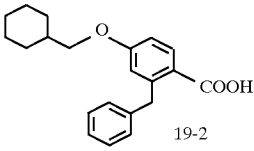

A solution of 4-cyclohexylmethyloxybenzoic acid (19-1) (1.00 g, 4.27 mmol, 1 equiv) in tetrahydrofuran (10 mL) was added to a solution of sec-butyllithium (1.3M, 8.21 mL, 10.7 mmol, 2. 50 equiv) and N, N, N', N'-tetramethylethylenediamine (1.61 mL, 10.7 mmol, 2.50 equiv) in tetrahydrofuran (10 mL) at −100 ° C. (ethanol-$N_2$(l)). The resultant orange suspension was stirred at −100° C. for 1 h, then warmed to −78 ° C. and held at that temperature for 15 min. Benzyl bromide (2.00 mL, 16.8 mmol, 3.93 equiv) was added to the cold reaction mixture, causing the color to change to light yellow. The suspension was stirred at −78° C. for 35 min, then was poured into water (150 mL). The aqueous mixture was acidified to approximately pH 2 with an aqueous 1N hydrochloric acid solution and was extracted with ethyl acetate (2×100 mL). The combined organic layers were dried over magnesium sulfate and were concentrated. The residue was purified by flash column chromatography (40% hexanes in ethyl acetate initially, grading to 100% ethyl acetate) to afford the desired carboxylic acid 19-2 as a white solid.

The coupling 19-2 and 4-aminopyridine and subsequent reduction of the amide product were carried out as described in Example 14 to afford the final product 19-3.

$^1$H NMR (400 MHz, $CDCl_3$), δ: 8.12 (br d, 2H, J=6.4 Hz, PyH), 7.26 (m, 2H, PhH), 7.20 (m, 1H, PhH), 7.20 (d, 1H J=8.4 Hz, ArH), 7.09 (br d, 1H, J=7.1 Hz, PhH), 6.80 (d, 1H, J=2.8 Hz, ArH), 6.75 (dd, 1H, J=8.4, 2.6 Hz, ArH), 6.26 (br d, 2H, J=6.4 Hz, PyH), 4.12 (m, 3H, $CH_2$NH and NH), 4.00 (s, 2H, ArC$H_2$Ph), 3.73 (d, 2H, J=6.4 Hz, OC$H_2$Cy), 1.86 (br d, 2H, J=12.8 Hz, CyH), 1.81–1.65 (m, 4H, CyH), 1.37–1.13 (m, 3H, CyH), 1.05 (qd, 2H, J=12.1, 2.9 Hz, CyH); mp: 114°–116° C.

EXAMPLE 20

Preparation of 4-(4-cyclohexylmethyloxy-2-benzyloxybenzyl)aminopyridine (20-6)

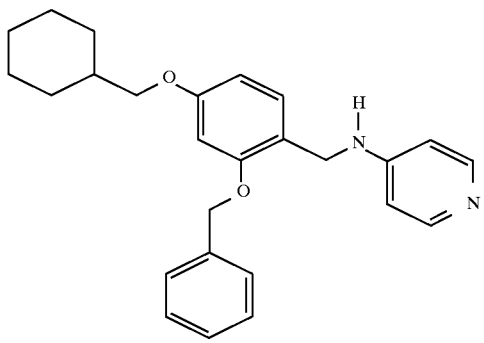

20-6

Step A:

Preparation of Methyl-(4-cyclohexylmethyloxy-2-hydroxy)benzoate (20-2)

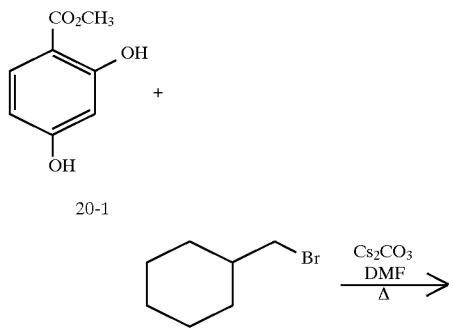

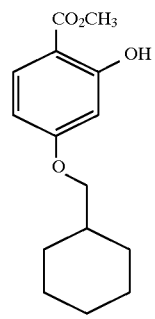

20-2

Cyclohexylmethyl bromide (4.56 mL, 32.67 mmol, 1.1 equiv) was added to a suspension of methyl 2,4-dihydroxybenzoate (20-1) (5.0 g, 29.7 mmol, 1 equiv) and cesium carbonate (33.9 g, 104.1 mmol, 3.5 equiv) in N, N-dimethylfonnamide (100 mL) at 23° C. The reaction mixture was heated to 70° C. and was stirred at that temperature for 5 h. The solution was cooled to 23° C. and was concentrated. The residue was diluted with ethyl acetate, and the resulting solution was washed with an aqueous saturated ammonium chloride solution (2×25 mL). The combined aqueous layers were further extracted with 50% ethyl acetate in hexane (2×100 mL). The combined organic layers were dried over magnesium sulfate and were concentrated. The residue was purified by flash column chromatography (3% ethyl acetate in hexanes) to afford 20-2. TLC (30% EtOAc-hexane), $R_f$=0.35 (UV)TLC (5% EtOAc-hexane), $R_f$=0.51 (UV);

$^1$H NMR (400 MHz, $CDCl_3$), δ: 10.94 (s, 1H, OH), 7.71 (d, 1H, J=9.52 Hz, ArH [ortho to $CO_2CH_3$]), 6.41 (m, 2H, ArH [meta to $CO_2CH_3$]), 3.90 (s, 3H, $CO_2CH_3$), 3.76 (d, 2H, J=6.04 Hz, OC$H_2$Cy), 1.77 (m, 6H, CyH), 1.26 (m, 3H, CyH), 1.05 (m, 2H, CyH).

Step B:

Preparation of Methyl(4-cyclohexylmethyloxy-2-benzyloxy)benzoate (20-3)

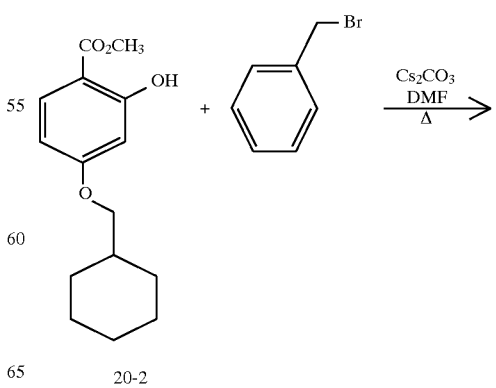

20-2

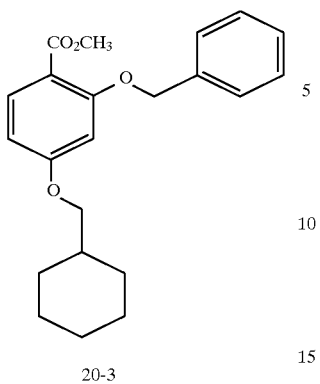

20-3

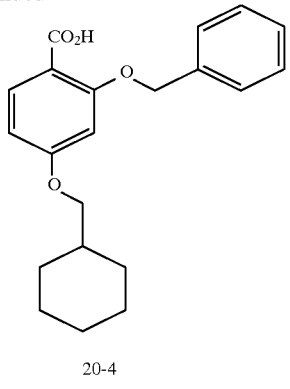

20-4

Benzyl bromide (0.216 mL, 1.81 mmol, 1.2 equiv) was added to a suspension of 20-2 (400 mg, 1.51 mmol, 1 equiv) and cesium carbonate (1.72 g, 5.30 mmol, 3.5 equiv) in N,N-dimethylformamide (15 mL) at 23° C. The reaction mixture was heated to 70° C. and was stirred at that temperature for 2 h. The solution was cooled to 23° C. and was concentrated. The residue was diluted with ethyl acetate (60 mL), and the resulting solution was washed with an aqueous saturated ammonium chloride solution (2×30 mL). The organic layer was dried over magnesium sulfate and was concentrated to afford the product 20-3 as a pale yellow oil which was used without further purification.

$^1$H NMR (400 MHz, CDCl$_3$), δ: 7.87 (d, 1H, J= =8.61 Hz, ArH [ortho to CO$_2$CH$_3$]), 7.53 (d, 2H, J=7.32 Hz, PhH), 7.39 (d, 2H, J=6.95 Hz, PhH), 7.32 (m, 1H, PhH), 6.53 (s, 1H, ArH [meta to CO$_2$CH$_3$]), 6.51 (d, 1H, J=8.79 Hz, ArH [meta to CO$_2$CH$_3$]), 5.17 (s, 2H, CH$_2$Ph), 3.87 (s, 3H, CO$_2$CH$_3$), 3.77 (d, 2H, J=6.22 Hz, CH$_2$Cy), 1.85 (d, 2H, J=13.36 Hz, CyH), 1.76 (m, 4H, CyH), 1.27 (m, 2H, CyH), 1.05 (m, 2H, CyH); TLC (10% EtOAc-hexane), R$_f$=0.14 (UV)

Step C:

Preparation of (4-cyclohexylmethyloxy-2-benzyloxy)benzoic acid (20-4)

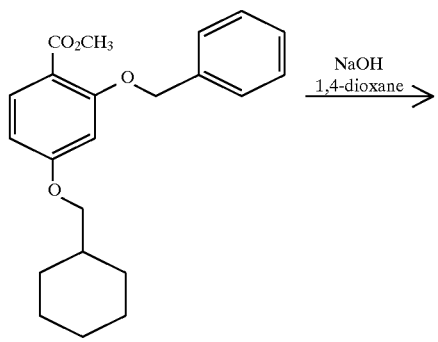

20-3

A solution of sodium hydroxide (302 mg, 7.55 mmol, 5 equiv) in water (3 mL) was added to a solution of 20-3 (1.51 mmol, 1 equiv) in 1,4-dioxane (7 mL). The reaction mixture was heated at reflux for 16 h. The solution was cooled to 23° C., and then was diluted with ethyl acetate (60 mL). The organic layer was washed with an aqueous 10% potassium hydrogen sulfate solution (2×30 mL) and was dried over magnesium sulfate and was concentrated to afford 20-4 as a white solid, which was used without further purification.

$^1$H NMR (400 MHz, CD$_3$OD), δ: 7.85 (d, 1H, J= =8.79 Hz, ArH [ortho to CO$_2$H]), 7.51 (d, 2H, J= =7.51 Hz, PhH), 7.35 (m, 3H, PhH), 6.65 (d, 1H, J= =2.01 Hz, ArH [meta to CO$_2$H]), 6.57 (dd, 1H, J= =8.79, 2.20 Hz, ArH [meta to CO$_2$H]), 5.25 (s, 2H, CH$_2$Ph), 3.80 (d, 2H, J= =6.22 Hz, CH$_2$Cy), 1.85 (d, 2H, J= =14.10 Hz, CyH), 1.76 (m, 4H, CyH), 1.29 (m, 3H, CyH), 1.10 (m, 2H, CyH).

Step D:

Preparation of N-4-pyridyl-(4-cyclohexylmethyloxy-2-benzyloxy)benzamide (20-5)

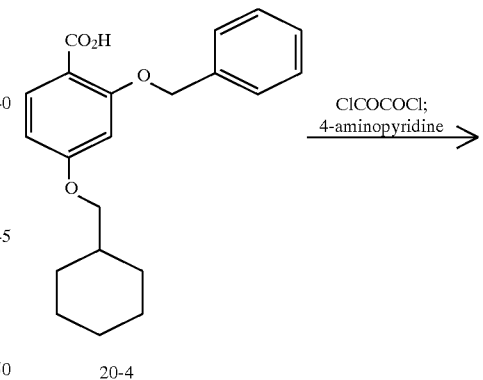

20-4

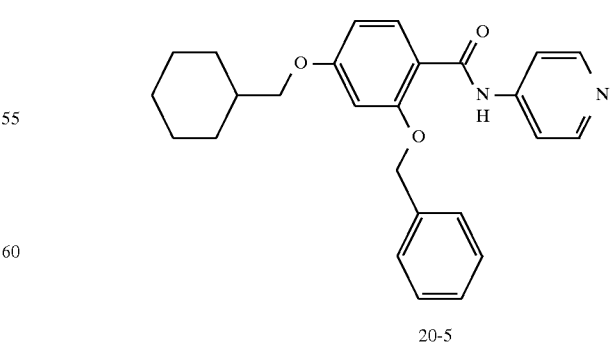

20-5

Oxalyl chloride (0.391 mL, 4.49 mmol, 3 equiv) was added to a solution of 20-4 (509 mg, 1.49 mmol, 1 equiv) in dichloromethane (6 mL) at 23° C. Once gas evolution ceased (approximately 5 min after the addition of oxalyl chloride), the volatiles were removed in vacuo. The residue was dissolved in dichloromethane (11 mL), and the resulting solution was transferred via cannula to a suspension of 4-aminopyridine (704 mg, 7.47 mmol, 5 equiv) and triethylamine (1.67 mL, 11.96 mmol, 8 equiv) in dichloromethane (10 mL) at 23° C. The reaction mixture was stirred for 2 h at 23° C., then was concentrated in vacuo. The residue was purified by flash column chromatography (15% hexanes in ethyl acetate) to afford the product 20-5 as a white solid.

$^1$H NMR (400 MHz, CDCl$_3$), δ: 9.99 (s, 1H, NH), 8.34 (d, 2H, J= =4.95 Hz, PyH), 8.24 (d, 1H, J= =8.79 Hz, ArH [meta to OCH$_2$Cy]), 7.55 (d, 2H, J= =7.69 Hz, PhH), 7.52 (m, 3H, PhH), 7.06 (dd, 2H, J= =4.95, 1.28 Hz, PyH), 6.68 (d, 1H, J= =8.79 Hz, ArH [ortho to OCH$_2$Cy]), 6.65 (s, 1H, ArH [ortho to OCH$_2$Cy]), 5.19 (s, 2H, CH$_2$Ph), 3.85 (d, 2H, J= =6.23 Hz, CH$_2$Cy), 1.89 (d, 2H, J= =12.64 Hz, CyH), 1.77 (m, 4H, CyH), 1.29 (m, 2H, CyH), 1.09 (m, 2H, CyH); TLC (100% EtOAc), R$_f$=0.38 (UV)

Step E:

Preparation of 4-(4-cyclohexylmethyloxy-2-benzyloxybenzyl)aminopyridine (20-6)

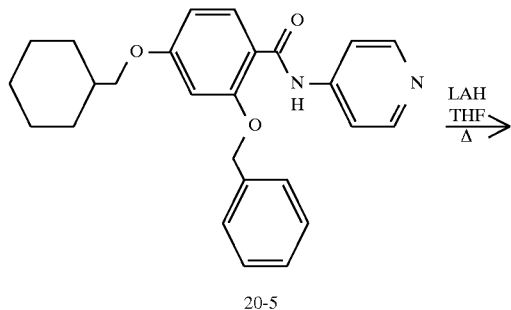

A solution of lithium aluminum hydride in tetrahydrofuran (1.0M, 4.12 mL, 4.12 mmol, 4 equiv) was added to a solution of 20-5 (430 mg, 1.03 mmol, 1 equiv) in tetrahydrofuran (3 mL) at 0° C. The reaction mixture was heated to 50° C. and held at that temperature for 2 h. The mixture was cooled to 0C, and excess lithium aluminum hydride was quenched by the consecutive addition of water (0.155 mL), aqueous 15% sodium hydroxide solution (0.155 mL), and water (0.467 mL). The resulting aluminum salts were removed by filtration. The filtrate was concentrated, and the residue was purified by flash column chromatography (0.5% methanol in chloroform saturated with ammonia) to afford the product 20-6 as a white solid (mp=131°–132° C., 330 mg, 80%).

$^1$H NMR (400 MHz, CDCl$_3$), δ: 8.16 (dd, 2H, J= =4.77, 1.46 Hz, PyH), 7.37 (m, 5H, PhH), 7.15 (d, 1H, J= =8.24 Hz, ArH [meta to OCH$_2$Cy]), 6.57 (d, 1H, J= =2.02 Hz, ArH [ortho to OCH$_2$Cy]), 6.46 (dd, 1H, J= =8.24, 2.19 Hz, ArH [ortho to OCH$_2$Cy]), 6.43 (dd, 2H, J= =4.77, 1.46 Hz, PyH), 5.09 (s, 2H, CH$_2$Ph), 4.50 (br s, 1H, NH), 4.32 (d, 2H, J= =5.86 Hz, CH$_2$NH), 3.73 (d, 2H, J= =6.41 Hz, CH$_2$Cy), 1.86 (d, 2H, J= =12.27 Hz, CyH), 1.75 (m, 4H, CyH), 1.27 (m, 3H, CyH), 1.04 (m, 2H, CyH); TLC (0.5% CH$_3$OH—CHCl$_3$ sat'd with NH$_3$), R$_f$=0.19 (UV)

EXAMPLE 21

Preparation of 4-{[3-amino-4-(cyclohexylmethyloxy)phenyl]methylamino}pyridine dihydrochloride (21-6)

Step A:

Preparation of Ethyl 4-(cyclohexylmethyloxy)-3-nitrobenzoate (21-2)

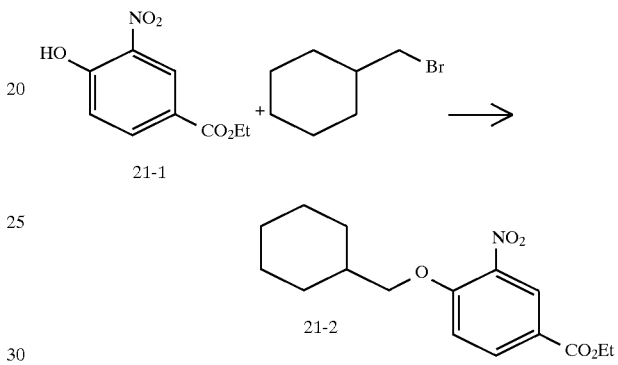

To a mixture of ethyl 4-hydroxy-3-nitrobenzoate (2-1) (2.11g, 10.0 mmol), cesium carbonate (6.52 g, 20.0 mmol), and sodium iodide (0.15g, 1.0 mmol) in DMF (20 ml) under nitrogen was added cyclohexylmethylbromide (1.67 ml, 12.0 mmol). The mixture was stirred 48 h at 60° C. The resulting mixture was evaporated under reduced pressure. To the residue was added water (100 ml), and the aqueous mixture was extracted with methylene chloride (2×200 ml). The organic fraction was washed with saturated sodium carbonate solution (100 ml) and brine (100 ml), dried (sodium sulfate), and the solvent was evaporated under reduced pressure. The residue was crystallized from ether/hexane to give product 21-2 as yellow crystals, mp: 79°–80° C.

$^1$H NMR (CDCl$_3$) δ 8.49 (1H, d, J=2 Hz), 8.19 (1H, dd, J=9, 2 Hz), 7.09 (1H, d, J=9 Hz), 4.39 (2H, q, J=7 Hz), 3.95 (2H, d, J=6 Hz), 1.69–1.89 (6H, m), 1.40 (3H, t, J=7 Hz), 1.06–1.38 (5H, m).

Step B:

Preparation of 4-(cyclohexylmethyloxy)-3-nitrobenzoic acid (21-3)

To a solution of 21-2 (1.38 g, 4.50 mmol) in THF (22.5 ml) cooled in an ice-bath was added 1N lithium hydroxide solution (22.5 ml). The resulting solution was stirred 18 h while warming to ambient temperature. The solution was partially evaporated at reduced pressure, and the remaining aqueous solution was washed with ethyl acetate (20 ml). The aqueous layer was cooled in an ice-bath, stirred rapidly, and concentrated hydrochloric acid (2 ml) was added dropwise, resulting in formation of a precipitate. The mixture was stirred 1 h, the precipitate was collected and dried in vacuo to give product 21-3 as a white solid, mp: 200°–202° C.

$^1$H NMR (CDCl$_3$) δ 8.56 (1H, d, J=2 Hz), 8.24 (1H, dd, J=9, 2 Hz), 7.13 (1H, d, J=9 Hz), 3.98 (2H, d, J=6 Hz), 1.70–1.90 (6H, m), 1.08–1.40 (5H, m).

Step C:
Preparation of N-(4-pyridyl)-4-(cyclohexylmethyloxy)-3-nitrobenzamide (21-4)

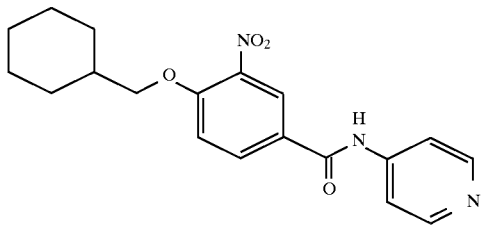

21-4

To a mixture of 21-3 (0.307 g, 1.1 mmol) and DMF (1 drop) in methylene chloride (3 ml) under nitrogen cooled in an ice-bath was added dropwise a solution of oxalyl chloride (0.113 ml, 1.3 mmol) in methylene chloride (1 ml). The resulting solution was stirred 1 h with ice-bath cooling, 1 h at ambient temperature, then was evaporated at reduced pressure to give crude 4-(cyclohexylmethyloxy)-3-nitrobenzoyl chloride as an oil.

To a mixture of the crude 4-(cyclohexylmethyloxy)-3-nitrobenzoyl chloride in methylene chloride (2 ml) under nitrogen cooled in an ice-bath was added dropwise a solution of 4-aminopyridine (0.282 g, 3.0 mmol) in methylene chloride (1 ml). The resulting solution was stirred 1 h with ice-bath cooling, then 2 h at ambient temperature. The mixture was diluted with methylene chloride (10 ml) and washed with saturated sodium bicarbonate solution (5 ml). The aqueous layer was extracted with methylene chloride (2×10 ml). The combined organic fractions were washed with water (10 ml), brine (10 ml), dried (sodium sulfate), and the solvent was evaporated under reduced pressure. The residue was purified by flash column chromatography on silica gel, eluting with methanol:ethyl acetate (5:95), to give a solid. The solid was recrystallized from ethyl acetate to give the product 21-4 as white crystals, mp: 197°–198° C.
$^1$H NMR (CDCl$_3$) δ 8.57 (2H, d, J=6 Hz), 8.37 (1H, d, J=2 Hz), 8.14 (2H, m), 7.62 (2H, d, J=8 Hz), 7.13 (1H, d, J=9 Hz), 3.98 (2H, d, J=6 Hz), 1.71–1.90 (6H, m), 1.08–1.38 (5H, m).
Analysis calculated for $C_{19}H_{21}N_3O_4$ C, 64.21; H, 5.96; N, 11.82
Found: C, 64.18; H, 5.97; N, 11.70

Step D:
Preparation of N-(4-pyridyl)-3-amino-4-(cyclohexylmethyloxy)benzamide (21-5)

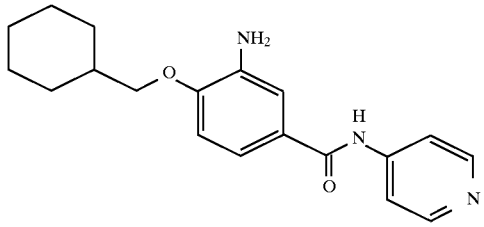

(21-5)

A mixture of 21-4 (0.171g, 0.48 mmol) and 10% palladium on carbon (0.040g) in ethanol (50 ml) was shaken on a Parr hydrogenation apparatus under hydrogen (50 psi) for 20 h. The mixture was filtered through filter aid and the filtrate was evaporated under reduced pressure to give a solid. The solid was dissolved in hot ethyl acetate (50 ml), treated with charcoal, and the mixture was filtered through filter aid. The filtrate was evaporated to one-third volume and cooled. The resulting precipitate was collected and dried in vacuo to give product 21-5 as a white crystalline solid, mp: 193°–194° C.

$^1$H NMR (CDCl$_3$) δ 8.52 (2H, d, J=6 Hz), 7.89 (1H, br s), 7.58 (2H, d, J=6 Hz), 7.25 (1H, d, J=2 Hz), 7.20 (1H, dd, J=8, 2 Hz), 6.80 (1H, d, J=8 Hz), 3.98 (2H, br s), 3.86 (2H, d, J=6 Hz), 1.66–1.91 (6H, m), 1.08–1.38 (5H, m);
Analysis calculated for $C_{19}H_{23}N_3O_2$.0.10 ethyl acetate C, 69.71; H, 7.18; N, 12.57
Found: C, 69.71; H, 7.17; N, 12.57

Step E:: Preparation of 4-{[3-amino-4-(cyclohexylmethyloxy)phenyl]methylamino}pyridine dihydrochloride (21-6)

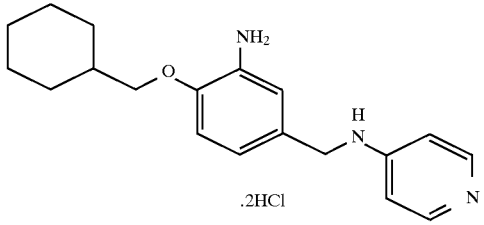

21-6

In a dry three-necked round bottom flask equipped with a condenser, nitrogen inlet, and septum, was placed a solution of 21-5 (0.059 g, 0.18 mmol) in anhydrous THF (2 ml). To the solution was added 2.0M borane-dimethylsulfide complex in THF (0.38 ml, 0.76 mmol) dropwise via syringe. The resulting mixture was stirred 1 h at 60° C. The mixture was cooled to ambient temperature, and 6N hydrochloric acid (1 ml) was added dropwise. The mixture was heated in a 60° C. oil-bath for five minutes, cooled to ambient temperature, and poured into saturated sodium carbonate solution (10 ml). The mixture was extracted with ethyl acetate (3×20 ml). The combined organic fractions were washed with brine (20 ml), dried (sodium sulfate), and the solvent was evaporated under reduced pressure. The residue was purified by flash column chromatography on silica gel, eluting with methanol:ethyl acetate (10:90), to give a gummy solid. The solid (0.052 g) was suspended in ethanol (1 ml) and ethanolic HCl (6M, 0.065 ml, 0.39 mmol) was added. The mixture was stirred, diluted with ether (10 ml), and the resulting precipitate was collected and dried in vacuo to give 21-6, as a white solid, mp: 173°–175° C.
$^1$H NMR (DMSO-d$_6$) δ 9.26 (1H, t, J=6 Hz), 8.7–9.8 (2H, br s), 8.22 (1H, d, J=7 Hz), 8.11 (1H, d, J=7 Hz), 7.25 (1H, s), 7.19 (1H, d, J=8 Hz), 7.09 (1H, d, J=8 Hz), 7.00 (1H, dd, J=7, 2 Hz), 6.85 (1H, dd, J=7, 2 Hz), 4.47 (2H, d, J=6 Hz), 3.84 (2H, d, J=6 Hz), 3.3–4.1 (2H, br s), 1.86 (2H, d, J=12 Hz), 1.60–1.82 (4H, m), 1.11–1.32 (3H, m), 1.00–1.10 (2H, m);
Analysis calculated for $C_{19}H_{25}N_3O.2$ HCl.0.25 H$_2$O C, 58.68; H, 7.13; N, 10.81
Found: C, 58.64; H, 6.99; N, 10.72

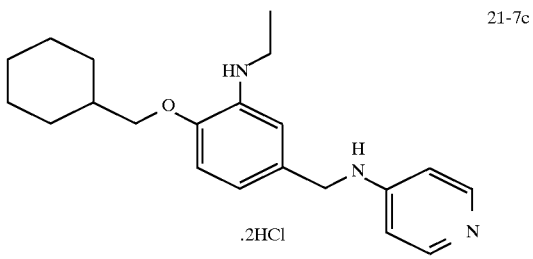

21-7c

Step F:
Preparation of 4-{[3-ethylamino-4-(cyclohexylmethyloxy)phenyl]methylaminol}pyridine dihydrochloride (21-7c)
Step 1: To a mixture of N-(4-pyridyl)-3-amino-4-(cyclohexylmethyloxy)benzamide (21-7a) (0.065 g, 0.20 mmol) in methylene chloride (1 ml) under nitrogen cooled in ice-bath was added acetic anhydride (0.040 ml, 0.42 mmol). The resulting mixture was stirred with ice-bath cooling for 2 h. The mixture was diluted with methylene chloride (4 ml), washed with 10% citric acid solution (2 ml), water (2 ml), saturated sodium bicarbonate solution (2 ml), water (2 ml), and brine (2 ml), dried over sodium sulfate, and concentrated in vacuo to give N-(4-pyridyl)-3-amino-4-(cyclohexylmethyloxy)benzamide (21-7b) (0.060 g, 82%) as a foam.

$^d$H(CDCl$_3$) 8.84 (1H, d, J 2 Hz), 8.52 (2H, d, J 6 Hz), 8.46 (1H, br s), 7.81 (1H, br s), 7.76 (1H, dd, J9,2 Hz), 7.65 (2H, dd, J 5,1 Hz), 6.96 (1H, d, J 8 Hz), 3.91 (2H, d, J 6 Hz), 2.24 (3H, s), 1.70–1.95 (6H, m), 1.07–1.42 (5H, m).

Step 2

Employing the procedure substantially as described for the preparation of 21-6, but starting with 21-7b (0.055g, 0.15 mmol), 21-7c was obtained as a white solid, mp: 137°–145° C.

$^d$H(DMSO-d6) 9.16 (1H, bs), 8.22 (1H, m), 8.13 (1H, m), 6.95–7.15 (3H, m), 6.97 (1H, d, J 7 Hz), 6.87 (1H, d, J 7 Hz), 4.45 (2H, d, J 5 Hz), 3.83 (2H, d, J 5 Hz), 3.4–3.8 (2H, br s), 3.18 (2H, q, J7 Hz), 1.60–1.90 (6H, m), 1.17 (3H, t, J7 Hz), 1.04–1.82 (5H, m).

Analysis calculated for C$_{21}$H$_{29}$N$_3$O.2 HCl.0.50 H2O C, 59.85; H, 7.65; N, 9.97

Found: C, 59.90; H, 7.49; N, 9.94

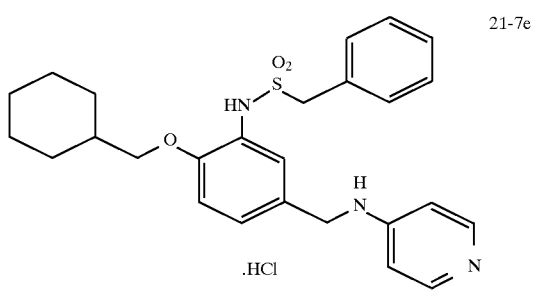

21-7e

Step G:

4-{[3-(phenylmethylsulfonamido)-4-(cyclohexylmethyloxy)phenyl]methylamino}pyridine dihydrochloride (21-7e)

Step 1: To a mixture of 21-7a (0.065 g, 0.20 mmol) and pyridine (0.032 ml, 0.40 mmol) in methylene chloride (2 ml) under nitrogen cooled in ice-bath was added alpha-toluenesulfonyl chloride (0.050 g, 0.26 mmol). The resulting mixture was stirred with ice-bath cooling for 3 h. The mixture was diluted with ethyl acetate (15 ml), washed with saturated sodium bicarbonate solution (5 ml) and brine (5 ml), dried over sodium sulfate, and concentrated in vacuo to give a gum (0.106 g). The gum was flash chromatographed on silica gel eluting with ethyl acetate to give N-(4-pyridyl)-3-(phenylmethylsulfonamido)-4-(cyclohexylmethyl-oxy)benzamide (21-7d) as a gum.

$^d$H(CDCl$_3$) 8.55(1H, d, J 6 Hz), 8.06 (1H, bs), 8.46 (1H, br s), 7.80 (1H, d, J 2 Hz), 7.71 (1H, dd, J9,2 Hz), 7.62 (2H, d, J 6 Hz),7.25–7.32 (3H, m), 7.26 (2H, m), 6.94 (1H, d, J 9 Hz), 6.83 (1H, bs), 4.39 (2H, s), 3.81 (2H, d, J 6 Hz), 1.65–1.82 (6H, m), 1.13–1.33 (3H, m), 0.90–1.08 (2H, m).

Step 2: Employing the procedure substantially as described for the preparation of 21-6, but starting with 21-7d (0.077 g, 0.16 mmol), 21-7e, was obtained as a white solid, mp: 135°–140° C.

$^d$H(DMSO-d6) 9.07 (1H, bs), 8.79 (1H, bs), 8.17 (2H, d, J 6 Hz), 7.26–7.35 (5H, m), 7.19 (1H, d, J 2 Hz),7.12 (1H, d, J 8Hz), 7.03 (1H, d, J 9 Hz), 6.92 (2H, bs), 4.43 (4H, m), 3.80 (2H, d, J 6 Hz), 1.62–1.82 (6H, m), 1.12–1.30 (3H, m), 0.95–1.10 (2H, m).

Analysis calculated for C26H31N3O3S.HCl: C, 62.20; H, 6.42; N, 8.37

Found: C, 62.31; H, 6.44; N, 8.36

EXAMPLE 22

Preparation of 4-{[3-propyl-4-(cyclohexylmethyloxy)phenyl]methylamino}pyridine (22-8)

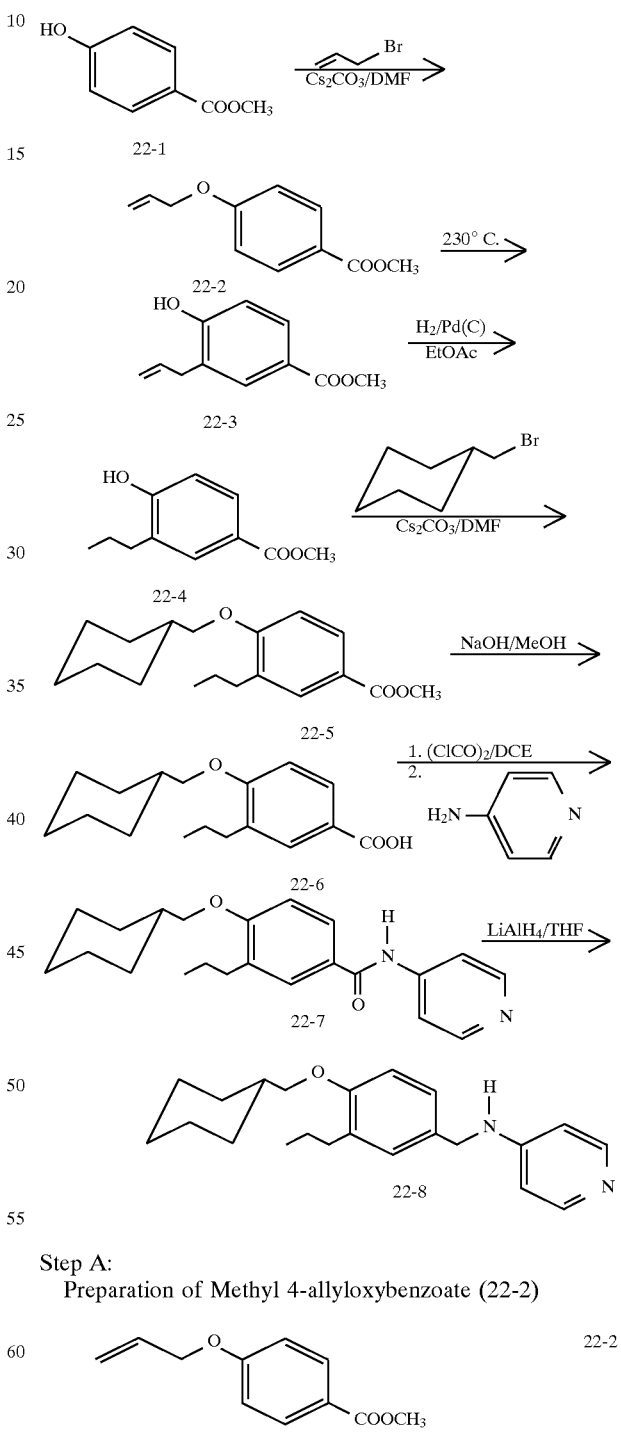

Step A:

Preparation of Methyl 4-allyloxybenzoate (22-2)

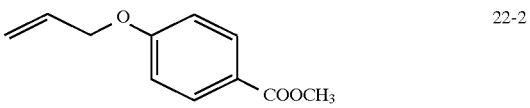

22-2

To a solution of methyl 4-hydroxybenzoate (22-1) (9.72 g, 64.36 mmol) in 100 mL of DMF was added 24.8 g (76.0 mmol) of Cs$_2$CO$_3$ followed by 5.0 mL (58.5 mmol) of allyl bromide. The resulting solution was then heated at 50° C. for 5 h. The solvent was distilled under reduced pressure and the residue was taken up in 200 mL of EtOAc. The organic phase was extracted with 1N NaOH (2×50 mL), water (5×50 mL) and brine (50 mL), dried (MgSO$_4$) and concentrated to afford product 22-2 as a white solid.

$^1$H NMR (CDCl$_3$) δ 8.00 (d, J=7.8 Hz, 2H), 6.95 (d, J=7.8 Hz, 2H), 6.05 (m, 1H), 5.45 (d, 1H), 5.30 (d, 1H), 4.60 (d, J=6.4 Hz, 2H), 3.85 (s, 3H).

Step B:

Preparation of Methyl 4-hydroxy-3-allylbenzoate (22-3)

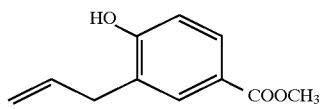

The neat allyl ether 22-2 from Step A (7.0 g, 38.6 mmol) was heated in an oil bath at 230° C. for 1 h. The reaction was followed by NMR and was found to be complete after 90 min. The resulting brown oil was cooled and subjected to column chromatography (1:1 EtOAc/Hexane) to afford 22-3 as a white solid.

$^1$H NMR (CDCl$_3$) δ 7.80 (m, 2H), 6.90 (d, J=7.8 Hz, 1H), 6.00 (m, 1H), 5.60 (s, 1H), 5.20 (s, 1H), 5.15 (d, J=6 Hz, 1H), 3.85 (s, 3H), 3.45 (d, J=6.4 Hz, 2H),

Step C:

Preparation of Methyl 4-hydroxy-3-propylbenzoate (22-4)

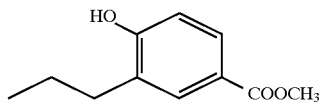

To 22-3 (6.0 g, 33.2 mmol) in 50 mL of EtOAc was added 60 mg of 5% Pd on carbon and the whole was hydrogenated at atmospheric pressure for 24 h. Hydrogen was removed from the reaction mixture and the solution was filtered through Celite. Evaporation of the solvent afforded product 22-4 as a white solid.

$^1$H NMR (CDCl$_3$) δ 7.84 (d, J=1.9 Hz, 1H), 7.79 (dd, J=2.0, 8.3 Hz, 1H), 6.79 (d, J=8.3 Hz, 1H), 5.49 (s, 1H), 3.88 (s, 3H), 2.60 (t, J=7.8 Hz, 2H), 1.65 (m, 2H), 0.97 (t, J=7.3 Hz, 3H).

Step D:

Preparation of Methyl 4-(cyclohexylmethyloxy)-3-propylbenzoate (22-5)

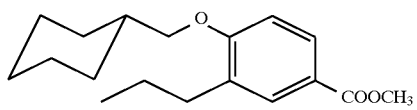

To a solution of 22-4 (915 mg, 5.0 mmol) in 10 mL of DMF was added 1.78 g (5.50 mmol) of Cs$_2$CO$_3$ followed by 0.68 mL (4.9 mmol) of bromomethyl cyclohexane. The resulting solution was then heated at 50° C. for 24 h. The solvent was distilled under reduced pressure and the residue was taken up in 20 mL of EtOAc. The organic phase was extracted with 1N NaOH (2×50 mL), water (5×5 mL) and brine (5 mL), dried (MgSO$_4$) and concentrated to afford 22-5 as an oil.

$^1$H NMR (CDCl$_3$) δ 7.84 (dd, J=2.4, 8.8 Hz, 1H), 7.80 (d, J=2.4, Hz, 1H), 6.80 (d, J=8.8 Hz, 1H), 3.87 (s, 3H), 3.80 (d, J=15.9 Hz, 2H), 2.60 (t, J=7.8 Hz, 2H), 1.95–1.00 (m, 13H), 0.93 (t, J=7.3 Hz, 3H).

Step E:

Preparation of 4-(cyclohexylmethyloxy)-3-propylbenzoic acid (22-6)

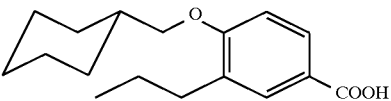

To a solution of 22-5 (1.0 g, 3.44 mmol) in 10 mL of MeOH and 2 mL of THF was added 3.5 mL (14 mmol) of 4N NaOH. The resulting solution was heated at 50° C. for 24 h, cooled and acidified by the addition of 15 mL of 1N HCl. The aqueous phase was extracted with 2×40 mL of EtOAc. The organic extracts were washed with brine (5 mL) and dried over MgSO$_4$. Evaporation of the solvent afforded 22-6 which was used without purification.

Step F:

Preparation of N-(4-pyridyl)-3-propyl-4-(cyclohexylmethyloxy)benzamide (22-7)

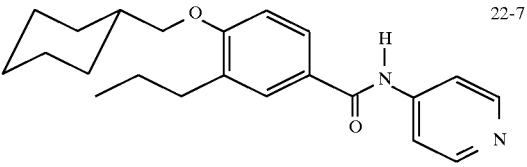

To a solution of 22-6 (770 mg, 2.78 mmol) in 10 mL of (CH$_2$Cl)$_2$ and 0.05 mL of DMF was added 0.26 mL (3.05 mmol) of oxalyl chloride. The resulting solution was heated at 50° C. for 30 min, cooled to 0° C. and treated with 1.20 g (13.8 mmol) of 4-aminopyridine. Stirring was continued for 2 h before the heterogeneous mixture was diluted with 50 mL of EtOAc and quenched with 25 mL of 5% Na$_2$CO$_3$. The organic extract was washed with sat'd NH$_4$Cl (3×50 mL), water (2×25 mL), brine (25 mL) and dried over MgSO$_4$. Evaporation of the solvent and column chromatography (EtOAc) afforded product 22-7.

$^1$H NMR (CDCl$_3$) δ 8.55 (d, J=8.0 Hz, 2H), 8.10 (bs, 1H), 7.75 (dd, J=2.4, 8.8 Hz, 1H), 7.70 (s, 1H), 7.60 (d, J=8.0 Hz, 2H), 6.85 (d, J=8.8 Hz, 1H), 3.80 (d, J=15.9 Hz, 2H), 3.70 (s, 3H), 2.60 (t, J=7.8 Hz, 2H), 1.95–1.00 (m, 13H), 0.90 (t, J=7.3 Hz, 3H).

Step G:

Preparation of 4-{[3-propyl-4-(cyclohexylmethyloxy) phenyl]methylamino}pyridine (22-8)

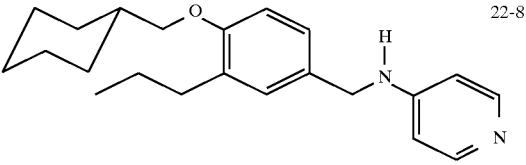

To a solution of 22-7 (1.0 g, 2.8 mmol) in 30 mL of THF was added 10.0 mL (10.0 mmol) of LiAlH$_4$ (1M in THF) and the resulting solution was stirred at room temperature for 16 h, cooled to 0° C. and quenched with 1 mL of water, 1 mL of 15% NaOH then 3 mL of water. The heterogeneous mixture was diluted with 50 mL of EtOAc and washed with 3×5 mL of sodium potassium tartrate, water (2×5 mL), brine (5 mL) and dried over MgSO$_4$. Evaporation of the solvent and column chromatography (9:1 CHCl$_3$ (sat'd NH$_3$)/isopropyl alcohol) afforded 22-8.

$^1$H NMR (CDCl$_3$) δ 8.18 (d, J=8.1 Hz, 2H), 7.10 (d, J=7.5 Hz, 1H), 7.07 (s, 1H), 6.77 (d, J=7.5 Hz, 2H), 6.41 (d, J=8.1 Hz, 2H), 4.45 (bs, 1H), 4.24 (d, J=15.9 Hz, 2H), 3.74 (d, J=5.1 Hz, 2H), 2.57 (t, J=7.8 Hz, 2H), 2.00–1.00 (m, 13H), 0.94 (t, J=7.3 Hz, 3H);

Analysis calculated for $C_{22}H_{30}N_2O$ C, 78.06; H, 8.93, N, 8.28
Found: C, 78.33; H, 8.99; N, 8.56

EXAMPLE 23

Preparation of 4-{[3-ethyl-4-(cyclohexylmethyloxy) phenyl]methylamino}pyridine (23-8)

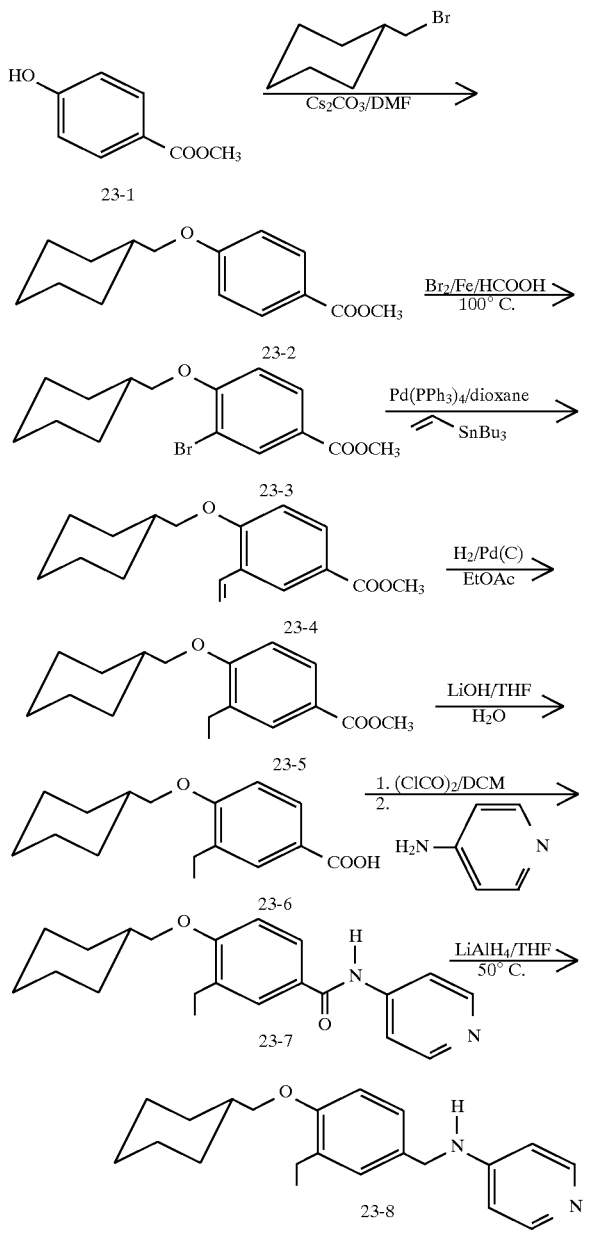

Step A:

Preparation of Methyl 4-cyclohexylmethyloxy-benzoate (23-2)

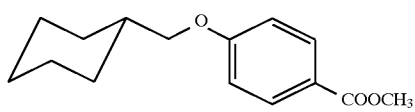

To a solution of methyl 4-hydroxybenzoate 23-1 (24.3 g, 160 mmol) in 250 mL of DMF was added 62 g (190 mmol) of $Cs_2CO_3$ followed by 20.4 mL (146 mmol) of cyclohexylmethyl bromide. The resulting slurry was then heated at 50° C. for 20 h. The solvent was distilled under reduced pressure and the residue was taken up in 500 mL of EtOAc. The organic phase was extracted with 1N NaOH (2×150 mL), water (5×150 mL) and brine (150 mL), dried ($MgSO_4$) and concentrated to afford product 23-2 as a white solid.
$^1$H NMR ($CDCl_3$) δ 7.98 (d, J=8.5 Hz, 2H), 6.90 (d, J=8.5 Hz, 2H), 3.88 (s, 3H), 3.78 (d, J=6.1 Hz, 2H), 2.00–1.00 (m, 11H).

Step B:

Preparation of Methyl 4-cyclohexylmethoxy-3-bromobenzoate (23-3)

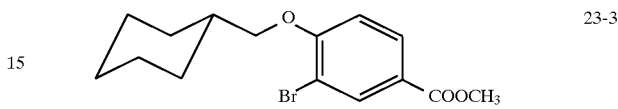

A solution of 23-2 (26.3 g, 106 mmol) was warmed on a steam bath in 110 mL of HCOOH with 592 mg (10.6 mmol) of Fe powder. Bromine (7.6 mL, 147.4 mmol) in 50 mL of HCOOH was added by dropping funnel over a period of 10 min. The reaction mixture was stirred an additional 1 h, cooled and poured onto ice. The resulting gum was taken up in 500 mL of EtOAc and washed with sat'd $Na_2S_2O_3$ (2×150 mL), water (5×100 mL), sat'd $NaHCO_3$ (3×100 mL) and brine (50 mL), dried ($MgSO_4$) and concentrated to afford product 23-3 as a white solid.
$^1$H NMR ($CDCl_3$) δ 8.22 (s, 1H), 7.98 (d, J=8.5 Hz, 1H), 6.90 (d, J=8.5 Hz, 1H), 3.88 (s, 3H), 3.78 (d, J=6.1 Hz, 2H), 2.00–1.00 (m, 11 H).

Step C:

Preparation of Methyl 4-cyclohexylmethyloxy-3-ethenylbenzoate (23-4)

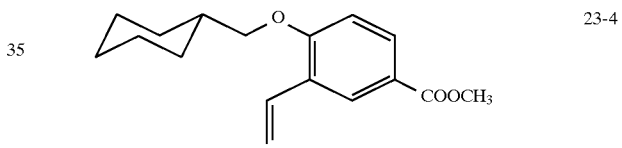

To a solution of 23-3 (810 mg, 2.5 mmol) in 11.5 mL of dioxane was added 820 mg (2.6 mmol) of vinyltributyl tin followed by 58 mg (0.05 mmol) of $Pd(PPh_3)_4$. The resulting solution was then heated at 100° C. for 20 h. The solvent was distilled under reduced pressure and the residue was chromatographed to afford product 23-4.
$^1$H NMR ($CDCl_3$) δ 8.19 (s, 1H), 7.85 (d, J=8.5 Hz, 1H), 7.00 (dd, J=, 1H), 6.92 (m, 1H), 5.85 (d, J=Hz, 1H), 5.35 (d, J=Hz, 1H), 3.88 (s, 3H), 3.78 (d, J=6.1 Hz, 2H), 2.00–1.00 (m, 11H).

Step D:

Preparation of Methyl 4-cyclohexylmethyloxy-3-ethylbenzoate (23-5)

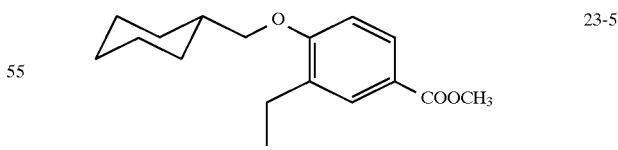

To 23-4 (560 mg, 2.0 mmol) in 15 mL of EtOAc was added 56 mg of 10% Pd on carbon and the whole was hydrogenated at atmospheric pressure for 24 h. Hydrogen was removed from the reaction mixture and the solution was filtered through Celite. Evaporation of the solvent afforded 23-5 as a white solid.
$^1$H NMR ($CDCl_3$) δ 7.84 (dd, J=2.4, 8.8 Hz, 1H), 7.80 (d, J=2.4 Hz, 1H), 6.80 (d, J=8.8 Hz, 1H), 3.87 (s, 3H), 3.80 (d, J=15.6 Hz, 2H), 2.60 (q, J=7.5 Hz, 2H), 1.95–1.00 (m, 14H).

Step E:
Preparation of 4-cyclohexylmethyloxy-3-ethyl-benzoic acid (23-6)

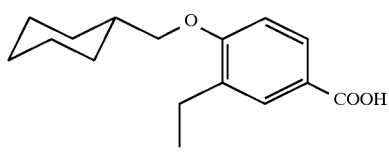
23-6

To a solution of 23-5 (290 mg, 1.0 mmol) in 7.6 mL of THF and 10 mL of water was added 210 mg (5.0 mmol) of LiOH. The resulting solution was stirred for 40 h, then acidified by the addition of 10 mL of 1N HCl. The aqueous phase was extracted with 2×20 mL of EtOAc. The organic extracts were washed with brine (5 mL) and dried over $MgSO_4$. Evaporation of the solvent afforded acid 23-6 which was used without purification.

Step F:
Preparation of N-(4-pyridyl)-3-ethyl-4-(cyclohexylmethyloxy)benzamide (23-7)

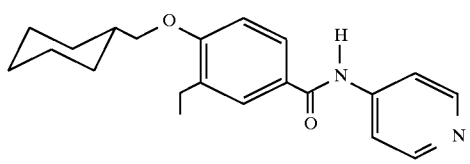
23-7

To a solution of 23-6 (270 mg, 1.0 mmol) in 3.6 mL of $CH_2Cl_2$ was added 0.13 mL (1.5 mmol) of oxalyl chloride. The resulting solution was stirred for 1 h, cooled to 0° C. and treated with 380 mg (4.0 mmol) of 4-aminopyridine. Stirring was continued for 1 h before the heterogeneous mixture was diluted with $CH_2Cl_2$ and quenched with sat'd $NaHCO_3$. The organic extract was washed with water, brine and dried over $Na_2SO_4$. Evaporation of the solvent and column chromatography (3:1 EtOAc/Hexane) afforded product 23-7.
$^1$H NMR ($CDCl_3$) δ 8.55 (d, J=8.0 Hz, 2H), 8.10 (bs, 1H), 7.75 (dd, J=2.4, 8.8 Hz, 1H), 7.70 (s, 1H), 7.60 (d, J=5.0 Hz, 2H), 6.85 (d, J=8.8 Hz, 1H), 3.80 (d, J=15.9 Hz, 2H), 2.60 (q, J=7.8 Hz, 2H), 1.95–1.00 (m, 14H).

Step G:

Preparation of 4-{[3-ethyl-4-(cyclohexylmethyloxy)phenyl]methylamino} pyridine (23-8)

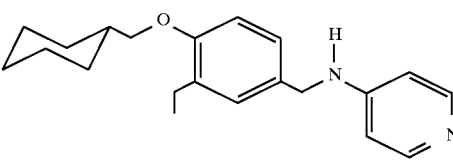
23-8

To a solution of 23-7 (290 mg, 0.86 mmol) in 5 mL of THF was added 1.7 mL (1.7 mmol) of $LiAlH_4$ (1M in THF) and the resulting solution was heated at 50° C. for 2 h, cooled to 0° C. and quenched with 0.07 mL of water, 0.07 mL of 15% NaOH and 0.2 mL of water. The precipitate was filtered, concentrated and purified by column chromatography (94:6:0.6 $CHCl_3$/IPA/$NH_4OH$) to afford product 23-8.

$^1$H NMR ($CDCl_3$) δ 8.18 (d, J=8.1 Hz, 2H), 7.10 (d, J=7.5 Hz, 1H), 7.07 (s, 1H), 6.77 (d, J=7.5 Hz, 1H), 6.41 (d, J=8.1 Hz, 2H), 4.39 (bs, 1H), 4.24 (d, J=15.9 Hz, 2H), 3.74 (d, J=5.1 Hz, 2H), 2.60 (q, J=7.8 Hz, 2H), 2.00–1.00 (m, 14H);

Analysis calculated for $C_{21}H_{28}N_2O$ C, 77.72; H, 8.71, N, 8.63

Found: C, 77.53; H, 8.62; N, 8.56

The compounds shown in the table below are exemplary compounds of the present invention. The range of Ki values associated with the specifically listed compounds is represented as follows:

| | |
|---|---|
| + | <0.1 μM |
| ++ | >0.1 μM and <1.0 μM |
| +++ | >1.0 μM and <10.0 μM |
| ++++ | >10.0 μM |

TABLE 3

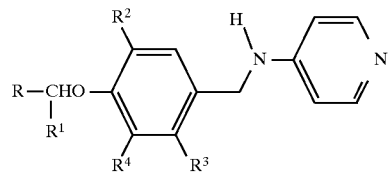

| R | R$^1$ | R$^2$ | R$^3$ | R$^4$ | Ki(th)μM | mp |
|---|---|---|---|---|---|---|
| cyclohexyl | H | —CH$_2$CH$_3$ | H | H | 0.64 | 116–9° |
| cyclohexyl | H | CH$_2$CH$_2$CH$_3$ | H | H | 0.50 | ? |

TABLE 3-continued
| R | R¹ | R² | R³ | R⁴ | Ki(th)μM | mp |
|---|---|---|---|---|---|---|
| 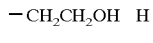 cyclohexyl | H | —CH₂CH₂OH | H | H | 4.4 | ? |
|  cyclohexyl | H |  cyclopropyl | H | H | 3.2 | 113–5° |
| 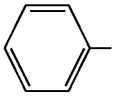 phenyl |  cyclopropyl | CH₂CH₂CH₃ | H | H | 0.8 | oil |
|  cyclohexyl | H | CH₂CH(CH₃)₂ | H | H | 1.5 | 103–6° |
| 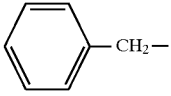 benzyl (Ph-CH₂—) |  cyclopropyl | CH₂CH₂CH₃ | H | H | 1.3 | ? |
| 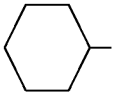 cyclohexyl | H | —CH=CH₂ | H | H | 0.26 | ? |
|  cyclohexyl | H | H | CH₂—Ph | H | 1.8 | 114–6° |
|  cyclohexyl | H | H | 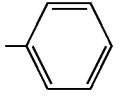 Ph | H | 6.4 | 125–6° |
| 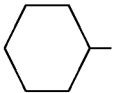 cyclohexyl | H | CH₂CH₂CH₃ | H | —CH₂OH | 3.8 | — |
|  cyclohexyl | H | H | H | —CH₂CH₂CH(CH₃)₂ | 3.2 | ? |

TABLE 3-continued
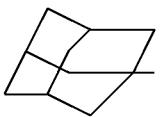
| R | R$^1$ | R$^2$ | R$^3$ | R$^4$ | Ki(th)μM | mp |
|---|---|---|---|---|---|---|
| 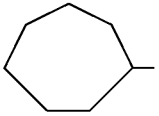 | H | CH$_2$CH$_2$CH$_3$ | H | H | 0.22 | ? |
| 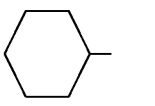 | H | CH$_2$CH$_2$CH$_3$ | H | H | 0.74 | ? |
| 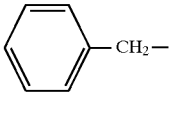 | H | H | OCH$_3$ | H | 3.2 | 128–9° |
| 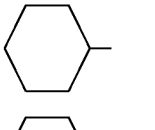 | —CH(CH$_3$)$_2$ | CH$_2$CH$_2$CH$_3$ | H | H | 0.5 | 179–80° |
| 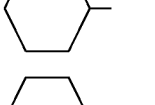 | H | H | OCH$_2$Ph | H | 1.8 | 131–2° |
|  | H | CH$_2$CH$_2$CH$_3$ | CH$_2$—Ph | H | >0.9 | 182–3° |
|  | H | H | OH | H | 1.6 | 150° |
| 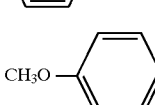 | H | —NH$_2$ | H | H | 2.9 | 173–5° |
| 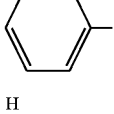 | H | 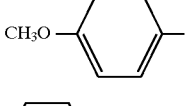 | CH$_2$CH$_2$CH$_3$ | H | H | 0.32 | 140–3° |
| 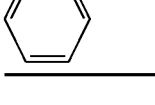 | H | CH$_2$CH$_2$CH$_3$ | H | H | 1.8 | 94–6° (freebase) |
|  | H | CH$_2$CH$_2$CH$_3$ | H | H | 1.8 | 85–7° (freebase) |

TABLE 4

| R | W | X | Y | Z | Ki (thr) |
|---|---|---|---|---|---|
| cyclohexyl | i-amyl | H | H | H | +++ |
| cyclohexyl | Ph | H | H | H | ++++ |
| cyclohexyl | CH$_2$OH | H | H | H | ++++ |
| cyclohexyl | CH$_2$NH$_2$ | H | H | H | ++++ |
| cyclohexyl | CH$_2$NHCH$_3$ | H | H | H | +++ |
| cyclohexyl | CONCH$_3$ | H | H | H | ++++ |
| cyclohexyl | CH$_2$CH$_2$O$^t$Bu | H | H | H | ++++ |
| cyclohexyl | n-Pr | piperidyl-methyl | H | H | +++ |
| cyclohexyl | n-Pr | H | Et | H | ++++ |
| cyclohexyl | n-Pr | H | H | CH$_3$ | +++ |
| norbornenyl | n-Pr | H | H | H | ++ |
| i-butyl | n-Pr | H | H | H | +++ |
| naphthyl | n-Pr | H | H | H | +++ |

EXAMPLE 24

Preparation of N-((4-benzyloxy)phenylsulfonyl)-N'-aminomethyliminopiperazine

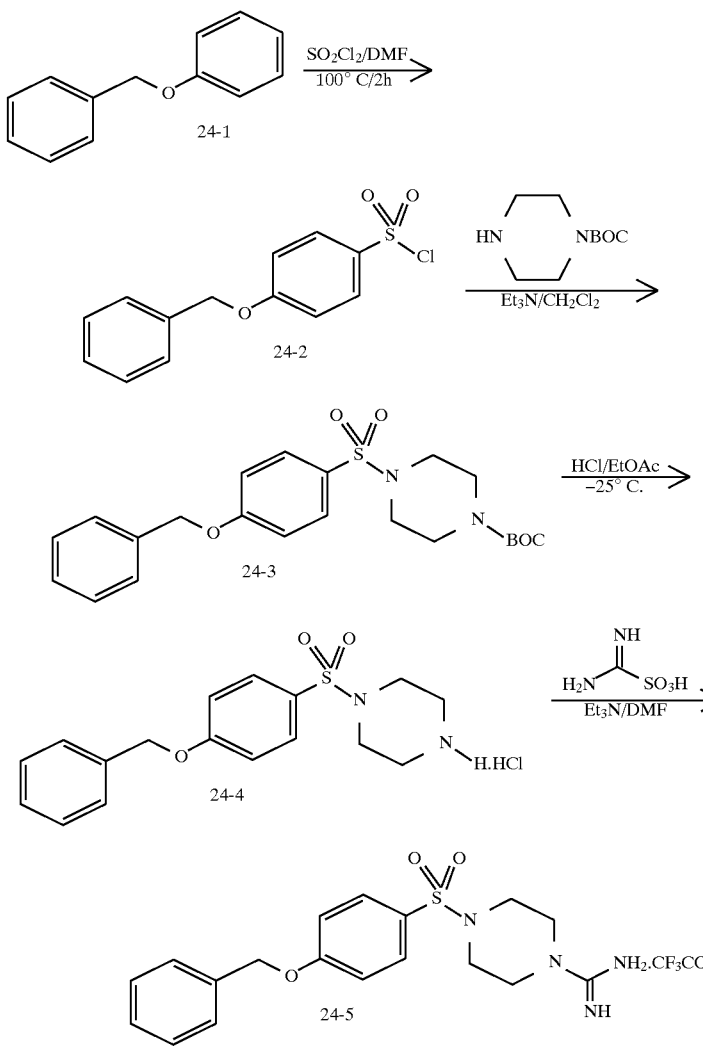

Step A:

Preparation of 4-benzyloxyphenylsulfonyl chloride (24-2)

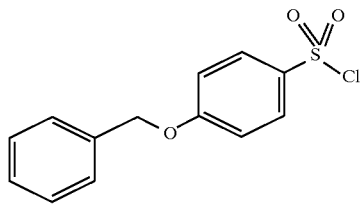

To a 0° C. solution of sulfonyl chloride (1.9 mL, 23.8 mmol) in 2 mL of DMF was added 4.0 g (21.7 mmol) of benzyl phenyl ether (24-1). The resulting solution was then heated at 100° C. for 2 h. The reaction mixture was then cooled and poured onto crushed ice. The aqueous layer was extracted with $CH_2Cl_2$ (x3). The combined organic extracts were dried ($Na_2SO_4$) and concentrated. Column chromatography (95:5 Hexane/EtOAc) and trituration (hexane) of the pure fractions afforded 24-2 as a pink solid.

$^1$H NMR (CDCl$_3$) δ 8.00 (d, J=7.8 Hz, 2H), 7.45 (m, 5H), 7.10 (d, J=7.8 Hz, 2H), 5.15 (s, 2H).

Step B:

Preparation of N-((4-benzyloxy)phenylsulfonyl)-N'-t-Butyloxycarbonylpiperazine (24-3)

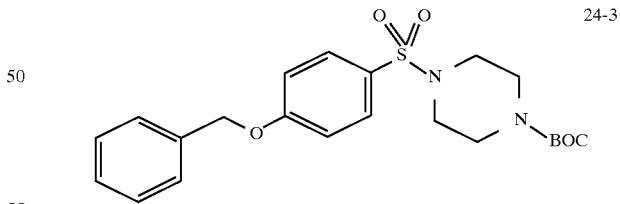

To a 0° C. solution of 24-2 (250 mg, 1.0 mmol) in 3 mL of $CH_2Cl_2$ was added 0.15 mL (1.1 mmol) of $Et_3N$ followed by 204 mg (1.1 mmol) of BOC piperazine. The resulting solution was allowed to stir to rt over 72 h. The reaction mixture was diluted with $CH_2Cl_2$ and washed with sat'd $NaHCO_3$ (3×5 mL). The organic phase was dried ($Na_2SO_4$) and concentrated to afford product 24-3 which was used directly without any purification.

$^1$H NMR (CDCl$_3$) δ 7.70 (d, J=7.8 Hz, 2H), 7.40 (m, 5H), 7.10 (d, J=7.8 Hz, 2H), 5.18 (s, 2H), 3.58 (t, J=7 Hz, 4H), 2.95 (t, J=7 Hz, 4H), 1.40 (s, 9H).

Step C:
Preparation of N-((4-benzyloxy)phenylsulfonyl)-piperazine (24-4)

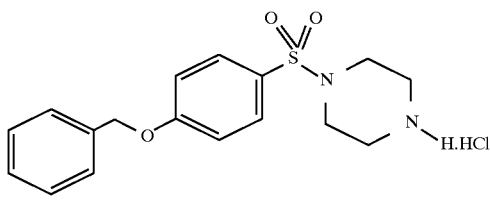

A −25° C. solution of crude 24-3 (390 mg, 0.94 mmol) in 10 mL of EtOAc was treated with HCl gas for 5 min and then stirred for 2 h at this temperature. Excess HCl was displaced from the solution by bubbling $N_2$ through the reaction mixture. The resulting solution was concentrated to give the amine hydrochloride as a white solid which was triturated (EtOAc) to give product 24-4.
$^1$H NMR (CDCl$_3$) δ 7.80 (d, J=7.8 Hz, 2H), 7.40 (m, 5H), 7.20 (d, J=7.8 Hz, 2H), 5.10 (s, 2H), 3,30 (m, 4H), 3.20 (m, 4H).

Step D:
Preparation of N-((4-benzyloxy)phenylsulfonyl)-N'-aminomethyliminopiperazine (24-5)

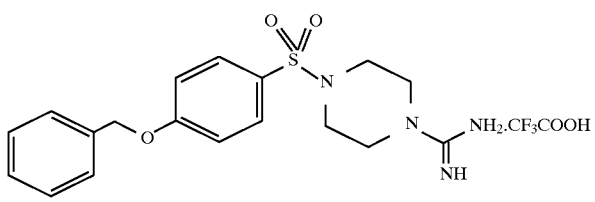

To a −25° C. solution of 24-4 (300 mg, 0.90 mmol) in 10 mL of DMF and 0.25 mL (1.79 mmol) of Et$_3$N was added 111 mg (0.895 mmol) of guanidine sulfonic acid. The resulting solution was allowed to stir to RT over 16 h. The reaction mixture was concentrated and subjected to preparative HPLC to afford product 24-5 as its TFA salt.
$^1$H NMR (CD$_3$OD) δ 7.80 (d, J=7.8 Hz, 2H), 7.40 (m, 5H), 7.20 (d, J=7.8 Hz, 2H), 5.20 (s, 2H), 3,60 (m, 4H), 3.05 (m, 4H); MS (FAB)=375;
Analysis calculated for C$_{18}$H$_{22}$N$_4$O$_3$S.0.4 H$_2$O.CF$_3$COOH C, 48.46; H, 4.84, N, 11.30
Found: C, 48.76; H, 4.69; N, 10.94

EXAMPLE 25

Preparation of N-((4-cyclohexylmethyloxy)-3-ethyl-phenylsulfonyl)-N'-aminomethyliminopiperazine (25-1)

25-1 was synthesized in the same manner as 24-5 by substituting 4-cyclohexylmethyloxy-3-ethylbenzene for 4-benzyloxybenzene in Step A, Example 24.

The compounds shown in the table below are exemplary compounds of the present invention. The range of Ki values associated with the specifically listed compounds is represented as follows:

| | |
|---|---|
| + | <0.1 µM |
| ++ | >0.1 µM and <1.0 µM |
| +++ | >1.0 µM and <10.0 µM |
| ++++ | >10.0 µM |

TABLE 5

R—CH$_2$O— (phenyl with R$^1$) —SO$_2$—N(piperazine)N—C(=NH)NH$_2$

| R | R1 | Ki(thr) µM | mp |
|---|---|---|---|
| phenyl | H | +++ | — |
| cyclohexyl | —CH$_2$CH$_3$ | ++ | 237–9° |

EXAMPLE 26

Preparation of 4-{[4-(Phenylmethyloxy)phenyl]methyl}benzamidine hydrochloride (26-6)

Step A:

Preparation of 4-[(4-Methoxyphenyl)hydroxymethyl]benzonitrile (26-2)

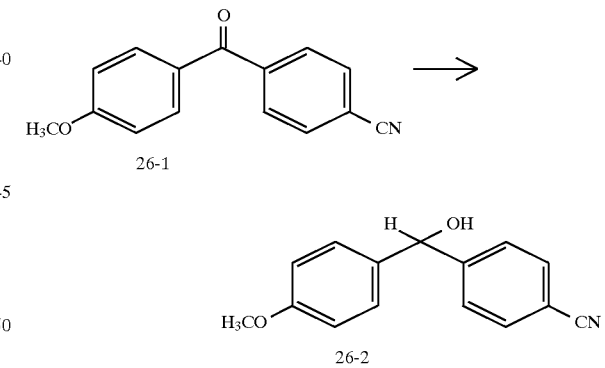

To a suspension of 4-(4-methoxybenzoyl)benzonitrile 26-1 (J. Med. Chem. 1991, 34, 2768–2778) (0.783 g, 3.3 mmol) in ethanol (35 ml) under nitrogen cooled in an ice-bath was added sodium borohydride (0.250 g, 6.6 mmol). The mixture was stirred 4 h with ice-bath cooling. To the resulting solution was added saturated ammonium chloride solution (35 ml). The mixture was partially evaporated under reduced pressure, and the resulting aqueous mixture was extracted with ethyl acetate (2×100 ml). The combined organic fractions were washed with brine (50 ml), dried (sodium sulfate), and the solvent was evaporated under reduced pressure. The residue was purified by flash column chromatography on silica gel, eluting with ethyl acetate/hexane (1:6 increasing to 1:3), to give product 26-2 as an oil.

NMR δ H(CDCl₃) 7.61 (2H, d, J=8 Hz), 7.50 (2H, d, J=8 Hz), 7.23 (2H, d, J=9 Hz), 6.87 (2H, dd, J=9, 2 Hz), 5.82 (1H, d, J=3 Hz), 3.79 (3H, s), 2.37 (1H, bs); IR 2227 cm⁻¹.

Step B:

Preparation of 4-[(4-Methoxyphenyl)methyl]benzonitrile (26-3)

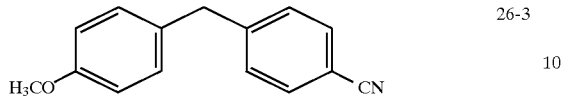

26-3

To a mixture of 26-2 (0.622 g, 2.6 mmol) and sodium iodide (1.56 g, 10.4 mmol) in acetonitrile (7 ml) at ambient temperature in a 3-necked round bottom flask equipped with a nitrogen inlet and rubber septum was added dichlorodimethylsilane (0.63 ml, 5.2 mmol) via syringe. The resulting mixture was stirred 60 min. Saturated sodium bicarbonate solution (30 ml) was added and the mixture was extracted with ethyl acetate (2×90 ml). The combined organic fractions were washed with 10% sodium thiosulfate solution (30 ml), brine (30 ml), dried (sodium sulfate), and the solvent was evaporated under reduced pressure. The residue was purified by flash column chromatography on silica gel, eluting with ethyl acetate/hexane (1:6 increasing to 1:5), to give product 26-3 as a white solid, mp: 41.5°–43.5° C.
ᵈH(CDCl₃) 7.56 (2H, d, J=8 Hz), 7.27 (2H, d, J=8 Hz), 7.07 (2H, d, J=9 Hz), 6.85 (2H, d, J=9 Hz), 3.97 (2H, s), 3.79 (3H, s).
IR 2224 cm⁻¹.

Step C:

Preparation of 4-[(4-Hydroxyphenyl)methyl]benzonitrile (26-4)

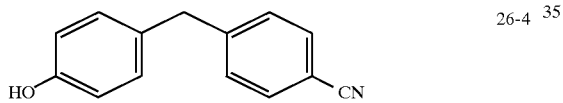

26-4

To a solution of 26-3 (0.391 g, 1.75 mmol) in methylene chloride (6 ml) cooled in an ice-bath in a 3-necked round bottom flask equipped with a nitrogen inlet and rubber septum was added 1.0M boron tribromide in methylene chloride (3.9 ml, 3.9 mmol) via syringe. The resulting mixture was stirred 18 h while warming to ambient temperature. Water (7 ml) was added and the mixture was extracted with ether (35 ml). The organic fraction was washed with brine (10 ml), dried (sodium sulfate), and the solvent was evaporated under reduced pressure. The residue was purified by flash column chromatography on silica gel, eluting with ethyl acetate/hexane (1:5 increasing to 1:3), to give product 26-4 as a white solid, mp: 163°–164° C.
δ H(CDCl₃) 7.56 (2H, d, J=8 Hz), 7.26 (2H, d, J=8 Hz), 7.02 (2H, d, J=8 Hz), 6.78 (2H, d, J=8 Hz), 4.78 (1H, s), 3.96 (2H, s).
IR 2230 cm⁻¹.

Step D:

Preparation of 4-{[4-(Phenylmethyloxy)phenyl]methyl}benzonitrile (26-5)

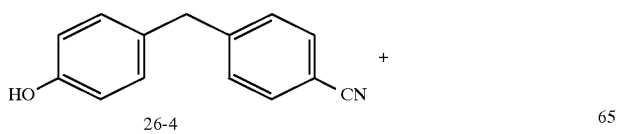

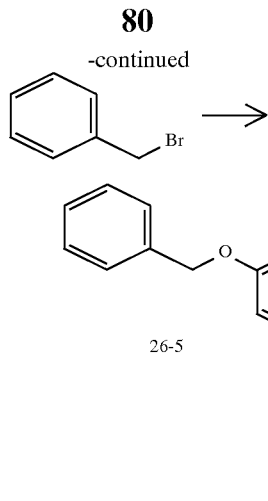

To a mixture of 26-4 (0.105 g, 0.50 mmol) and cesium carbonate (0.326 g, 1.0 mmol) in dimethylformamide (1 ml) under nitrogen was added benzyl bromide (0.071 ml, 0.60 mmol). The mixture was stirred 18 h at ambient temperature. The resulting mixture was evaporated under reduced pressure. To the residue was added saturated sodium bicarbonate solution (15 ml), and the aqueous mixture was extracted with methylene chloride (2×30 ml). The organic fraction was washed with brine (10 ml), dried (sodium sulfate), and the solvent was evaporated under reduced pressure. The residue was purified by flash column chromatography on silica gel, eluting with ethyl acetate/hexane (1:6 increasing to 1:5), to give a white solid. The solid was recrystallized from ethyl acetate/hexane to give product 26-5 as white crystals, mp: 110°–111° C.

δ H(CDCl₃) 7.56 (2H, d, J=8 Hz), 7.32–7.44 (5H, m), 7.27 (2H, d, J=8 Hz), 7.07 (2H, d, J=9 Hz), 6.92 (2H, d, J=9 Hz), 5.04 (2H, s), 3.97 (2H, s); IR 2223 cm⁻¹;

Analysis calculated for C₂₁H₁₇NO C, 84.25; H, 5.72; N, 4.68

Found: C, 84.02; H, 5.66; N, 4.74

Step E:

Preparation of 4-{[4-(Phenylmethyloxy)phenyl]methyl}benzamidine hydrochloride (26-6)

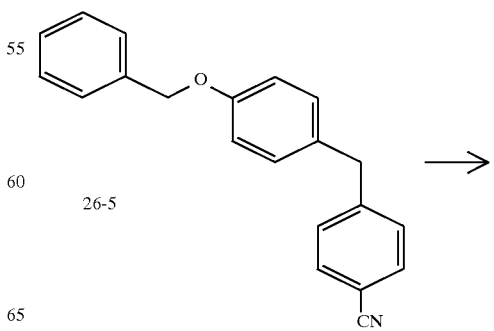

81

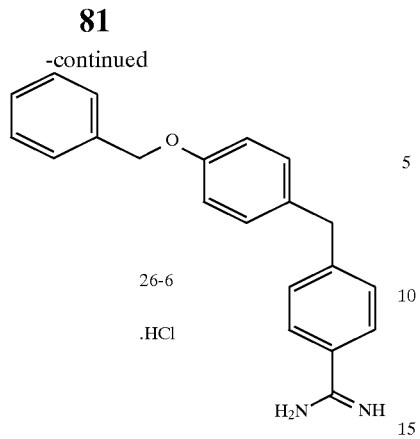

26-6

.HCl

To a solution of 26-5 (0.081 g, 0.27 mmol) in anhydrous ether (4 ml) at ambient temperature in a 3-necked round bottom flask equipped with a nitrogen inlet and rubber septum was added 1.0M lithium bis(trimethysilyl)-amide in THF (0.30 ml, 0.30 mmol) via syringe. The resulting solution was stirred 18 h at ambient temperature. To the solution was added ethanolic HCl (6M, 0.18 ml, 1.1 mmol, 4 equivalents). The mixture was stirred 4 h and the resulting precipitate was filtered off to give a solid (0.094 g). The solid was placed in saturated sodium bicarbonate solution (3 ml) and was extracted with ethyl acetate (5×10 ml). The combined organic fractions were washed with brine (10 ml), dried (sodium sulfate), and the solvent was evaporated under reduced pressure. The residue (0.017 g) was suspended in ethanol (1 ml) and ethanolic HCl (6M, 0.010 ml) was added. The mixture was stirred, diluted with ether (5 ml), and the resulting precipitate was collected. The precipitate was then stirred under water (1 ml) for 1 h. The resulting solid was collected and dried in vacuo to give product 26-6, as an off-white solid, mp: 234°–236° C.

δ H(DMSO-$d_6$) 9.30 (2H, br s), 9.09 (2H, br s), 7.74 (2H, d, J=8 Hz), 7.32–7.47 (7H, m), 7.17 (2H, d, J=8 Hz), 6.95 (2H, d, J=8 Hz), 5.06 (2H, s), 3.98 (2H, s).

Analysis calculated for $C_{21}H_{20}N_2O \cdot HCl \cdot 0.65 H_2O$ C, 69.18; H, 6.17; N, 7.68

Found: C, 69.24; H, 5.93; N, 7.40

EXAMPLE 27

Preparation of 4-{[4-(Cyclohexylmethyloxy)phenyl] methyl}-benzamidine hydrochloride (27-1)

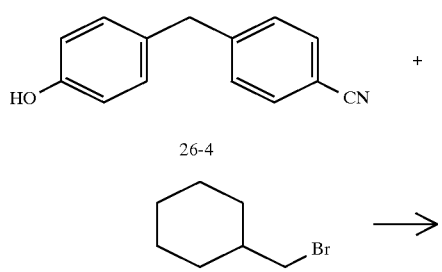

26-4

82

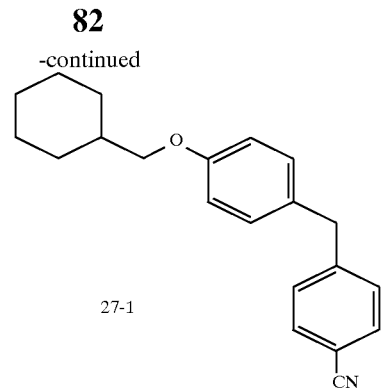

27-1

Step A:

Preparation of 4-{[4-(Cyclohexylmethyloxy)phenyl]-methyl}benzonitrile (27-1)

Employing the procedure substantially as described above, but substituting cyclohexylmethyl bromide for the benzyl bromide, the desired compound 27-1 was prepared: mp: 104°–106° C.;

$^1$H NMR (CDCl$_3$) δ 7.56 (2H, d, J=8 Hz), 7.26 (2H, d, J=8 Hz), 7.05 (2H, d, J=8 Hz), 6.83 (2H, d, J=8 Hz), 3.96 (2H, s), 3.72 (2H, d, J=6 Hz), 1.68–1.87 (6H, m), 1.17–1.38 (3H, m), 0.97–1.08 (2H, m); IR 2223 cm$^{-1}$.

Step B:

Preparation of 4-{[4-(Cyclohexylmethyloxy)phenyl]-methyl}benzamidine hydrochloride (27-3)

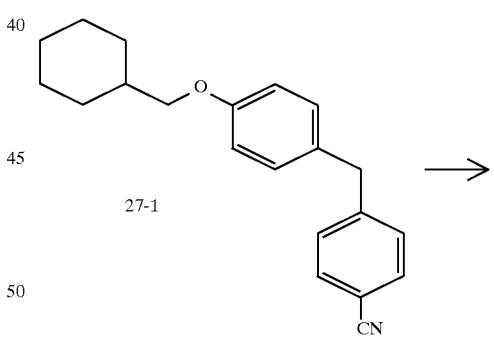

27-1

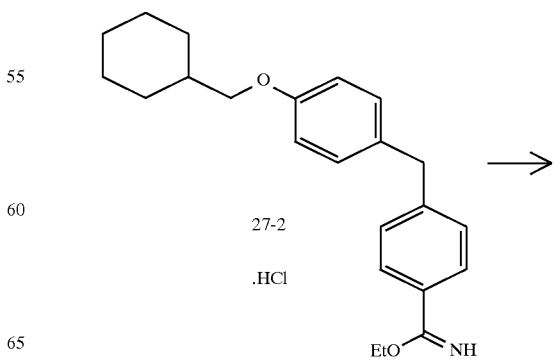

27-2

.HCl

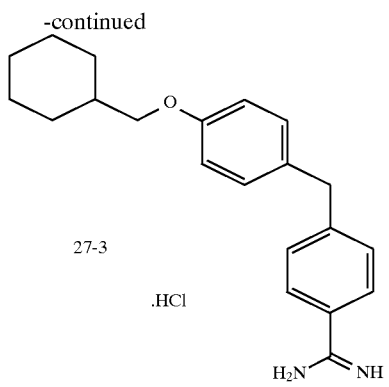

27-3 .HCl

Into a suspension of 27-1 (0.101 g, 0.33 mmol) in ethanol (3 ml) under nitrogen cooled in an ice-bath was bubbled hydrogen chloride until the mixture was saturated. The mixture was stirred 18 h while warming to ambient temperature. To the resulting solution was added ether (12 ml) resulting in formation of a precipitate. The precipitate was collected and dried in vacuo to give ethyl 4-{[4-(cyclohexylmethyloxy)phenyl]-methyl}benzimidate hydrochloride 27-2 as a white solid. NMR δ H(DMSO-$d_6$) 11.0–11.8 (2H, br s), 7.98 (2H, d, J=8 Hz), 7.48 (2H, d, J=8 Hz), 7.13 (2H, d, J=8 Hz), 6.85 (2H, d, J=8 Hz), 4.57 (2H, q, J=7 Hz), 3.99 (2H, s), 3.72 (2H, d, J=6 Hz), 1.68–1.80 (6H, m), 1.47 (3H, t, J=7 Hz), 1.19–1.26 (3H, m), 0.99–1.06 (2H, m).

Into a suspension of 27-2 (0.101 g, 0.26 mmol) in ethanol (5 ml) cooled in an ice-bath was bubbled ammonia until the mixture was saturated. The mixture was stirred 18 h while warming to ambient temperature. The resulting solution was evaporated to one-half volume under reduced pressure. Addition of ether (2 ml) resulted in formation of a precipitate. The precipitate was filtered off. The filtrate was evaporated under reduced pressure, and the residue was stirred under ether (5 ml). The resulting precipitate was collected and dried to give a solid. The solid (0.042 g) was suspended in ethanol (1 ml) and ethanolic HCl (6M, 0.025 ml) was added. The mixture was stirred, diluted with ether (10 ml), and the resulting precipitate was collected and dried in vacuo to give 27-3, as a white solid, mp: 257°–258° C.

δ H(DMSO-$d_6$) 9.1 (4H, br s), 7.73 (2H, d, J=8 Hz), 7.45 (2H, d, J=8 Hz), 7.14 (2H, d, J=8 Hz), 6.84 (2H, d, J=8 Hz), 3.97 (2H, s), 3.72 (2H, d, J=6 Hz), 1.63–1.80 (6H, m), 1.15–1.30 (3H, m), 0.95–1.10 (2H, m);

Analysis calculated for $C_{21}H_{26}N_2O \cdot HCl \cdot 0.40 H_2O$ C, 68.89; H, 7.65; N, 7.68

Found: C, 68.84; H, 7.45; N, 7.75

TABLE 6

R—X—Y—(phenyl with $R^2$)—$CH_2$—$R^1$

| R | X | Y | R¹ | R² | Ki(thr) μM | mp |
|---|---|---|----|----|----|-----|
| phenyl | —CH₂— | —O— | benzamidine | H | 0.39 | 234–6° |
| cyclohexyl | —CH₂— | —O— | benzamidine | H | 0.17 | 257–8° |
| cyclohexyl | —CH₂— | —O— | benzamidine | —CH₂CH₂CH₃ | 0.3 | 241–2° |
| cyclohexyl | —CH(CH(CH₃)₂)— | —O— | benzamidine | —CH₂CH₂CH₃ | 0.28 | 172–184° |
| cyclohexyl | —CH₂— | —O— | benzamidine | —CH₃ | 0.102 | 249–250° |
| cyclohexyl | —CH₂— | —O— | benzamidine | —CH₂CH₃ | 0.077 | 252–3° |
| cyclohexyl | —CH(CH(CH₃)₂)— | —O— | benzamidine | —CH₃ | 0.020 | 197–200° |

TABLE 6-continued
R—X—Y—[phenyl with R² ortho, CH₂—R¹ para]
| R | X | Y | R¹ | R² | Ki(thr) μM | mp |
|---|---|---|---|---|---|---|
| cyclohexyl | —CH—<br>CH(CH₃)₂ | —O— | 4-(C(=NH)NH₂)phenyl | —CH₂CH₃ | 0.020 | 198–9° |
EXAMPLE 28
Preparation of N-(4-phenoxymethylbenzyl) aminopyridine (28-6)
Step A:
Preparation of methyl 4-(phenoxymethyl)benzoate (28-3)
In a round bottom flask under $N_2$ was placed 28-1 (1.49 g, 15.9 mmol), $Cs_2CO_3$ (5.2 g, 16 mmol), 28-2 (3.6 g, 15.7
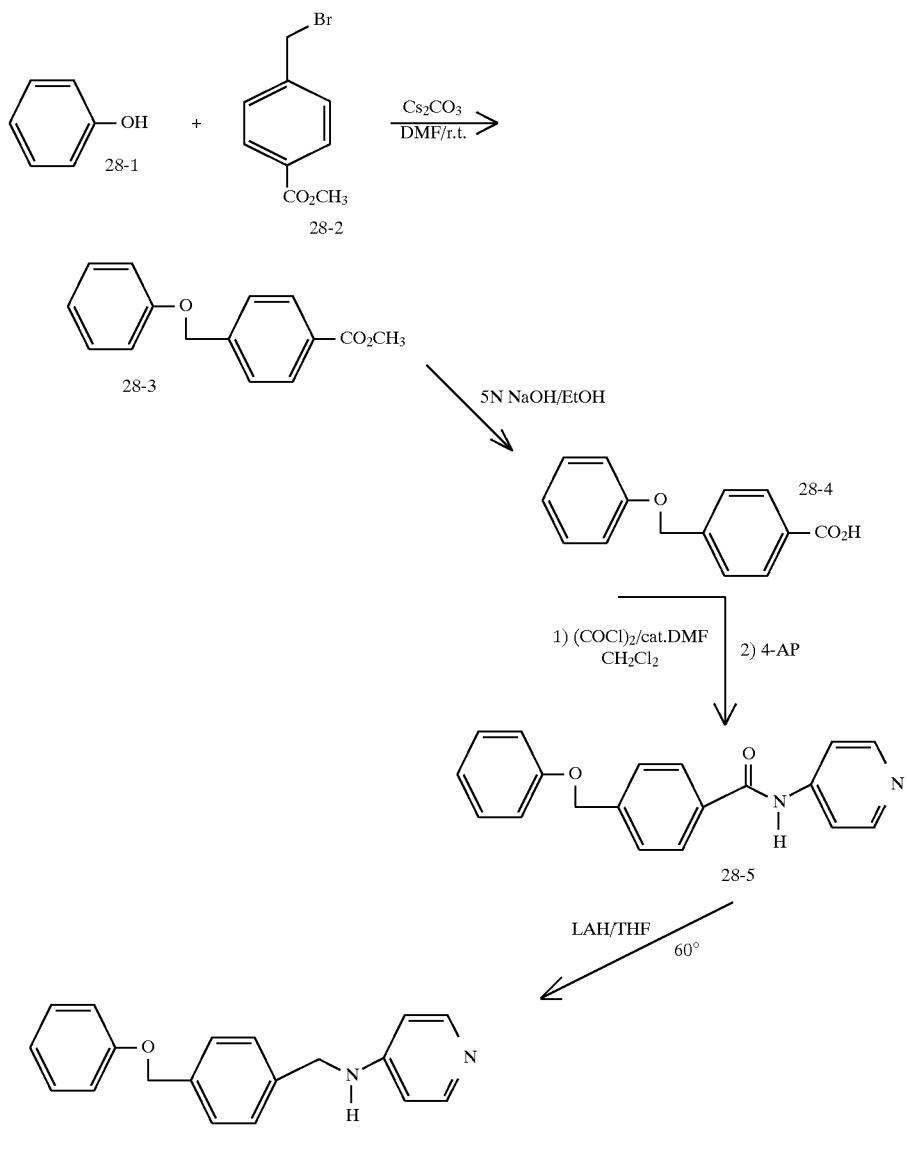

mmol) in DMF (250 ml) and the suspension stirred at room temperature. After 18 h, the mixture was poured into saturated $Na_2CO_3$ and extracted with EtOAc (3×). The organic extracts were dried, filtered and conc'd to dryness to yield 28-3.
$^1$H NMR (CDCl$_3$) δ 3.85 (3H, s), 5.05 (2H, s), 6.9 (3H, m), 7.2 (2H, d), 7.45 (2H, d), 8.0 (2H, d).
Step B:

Preparation of 4-(phenoxymethyl)benzoic acid (28-4)
Under $N_2$, a mixture of 28-3 (4.1 g, 15.9 mmol) in EtOH (100 ml) and 5N NaOH (100 ml) was stirred at room temperature. After 18 h, the reaction was heated at 80° C. for ½ h, cooled to room temperature and then acidified with 6N HCl. The mixture was extracted with EtOAc (3×) and the combined organic layer was washed with brine, dried, filtered and concentrated to dryness. The residue was triturated with Et$_2$O to yield 28-4.
$^1$H NMR (d$_6$-DMSO) δ 5.5 (2H, s), 7.35 (3H, m), 7.6 (H, m), 7.9 (2H, d), 8.35 (2H, d).
Step C:

Preparation of N-(4-(phenoxymethyl)benzcarboxamido)pyridine (28-5)

To a suspension of 28-4 (2.5 g, 11 mmol) in CH$_2$Cl$_2$ (40 ml) with 4 drops of DMF was added with stirring under $N_2$ at room temperature oxalyl chloride (1.7 g, 14 mmol). After 2 h, the solution was concentrated to dryness, flushed with CHCl$_3$ and then dissolved in CHCl$_3$ (30 ml). This solution was then added dropwise to a suspension of 4-aminopyridine (3.1 g, 33 mmol) in CHCl$_3$ (50 ml). After stirring at room temperature overnight, a sat'd solution of Na$_2$CO$_3$ was added and separated. The aqueous was further extracted with EtOAc (3×). The combined extracts were backwashed with H$_2$O, dried, filtered and concentrated to dryness. The residue was chromatographed on a Still column (60 mm) and the product eluted with 10% CH$_3$OH/CHCl$_3$ to yield 28-5; mp: 195°–197° C. (EtOH—CH$_3$OH);
$^1$H NMR (d$_6$-DMSO) δ 5.2 (2H, s), 6.95 (1H, t), 7.03 (2H, d), 7.3 (2H, t), 7.62 (2H, d), 7.79 (2H, d), 7.99 (2H, d), 8.48 (2H, d).
Analysis calculated for C$_{19}$H$_{16}$N$_2$O$_2$ C 74.98, H 5.30, N 9.21
Found: C 74.63, H 5.32, N 9.17
Step D:

Preparation of N-(4-phenoxymethylbenzyl)aminopyridine (28-6)

Under $N_2$, a solution of LAH 1.0M in hexane (10 ml, 10 mmol) was added dropwise to a suspension of 28-5 (1.75 g, 5.8 mmol) in THF (200 ml). After heating at 60° overnight with stirring, a sat'd solution of Na$_2$SO$_4$ was added until a white suspension was formed. The mixture was poured through super cel and washed with EtOAc. The organic layer was washed with water and the aqueous layer further extracted with EtOAc (2×). The combined organic extracts were dried, filtered and concentrated to dryness. The residue was chromatographed on a Still column (40 mm) and the product eluted with 10% CH$_3$OH—CHCl$_3$. The hydrochloride salt was prepared from EtOH—HCl and the product crystallized from EtOH to yield 28-6; mp: 213°–215° C. The compound analyzed for C$_{19}$H$_{18}$N$_2$O.HCl;
$^1$H NMR (d$_6$-DMSO) δ 4.55 (2H, d), 5.05 (2H, s), 6.95 (5H, m), 7.25 (2H, t), 7.4 (4H, q), 8.15 (2H, bd).
Analysis calculated for C, 69.82; H, 5.86; N 8.57 C, 69.82; H, 5.86; N, 8.57
Found: C, 69.73; H, 5.88; N, 8.58

The compounds shown in the table below are exemplary compounds of the present invention. The range of Ki values associated with the specifically listed compounds is represented as follows:

| | |
|---|---|
| + | <0.1 μM |
| ++ | >0.1 μM and <1.0 μM |
| +++ | >1.0 μM and <10.0 μM |
| ++++ | >10.0 μM |

TABLE 7

R—X—Y—⟨phenyl⟩—CH$_2$—R$^1$

| R | X | Y | R1 | Ki(thr) μM | mp |
|---|---|---|---|---|---|
| cyclohexyl | —CH$_2$— | —CH$_2$— | 4-pyridyl | +++ | 117–9° |
| phenyl | —O— | —CH$_2$— | 4-pyridyl | +++ | 213–5° |

EXAMPLE 29

Preparation of 4-(2-(3-cyclohexylmethyloxy-phenyl)ethyl)aminopyridine (29-6

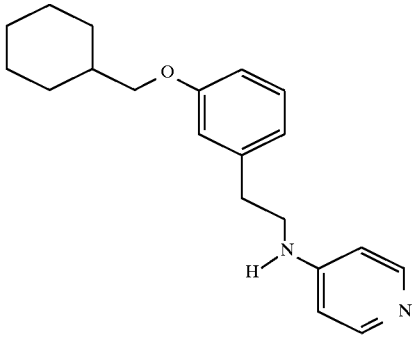

29-6

Step A:

Preparation of ethyl 3-hydroxy-phenylacetate (29-2)

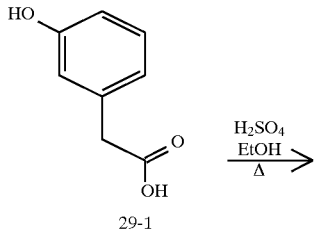

29-1

-continued

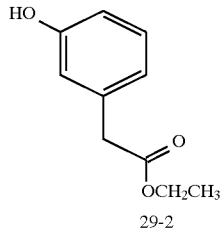

29-2

Sulfuric acid (0.018 mL, 0.329 mmol, 0.1 equiv) was added to a solution of 3-hydroxy-phenylacetic acid (29-1) (500 mg, 3.29 mmol, 1 equiv) in ethanol (10 mL) at 23° C. The reaction mixture was heated at reflux for 1.5 h. The solution was cooled to 23° C., then was concentrated. The residue was diluted with ethyl acetate, and the resulting solution was washed with water (2×20 mL). The organic layer was dried over magnesium sulfate and was concentrated to afford the product as a colorless oil 29-2 which was used without further purification.

$^1$H NMR (400 MHz, CDCl$_3$), δ: 7.17 (t, 1H, J= =7.88 Hz, ArH [meta to OH]), 6.83 (d, 1H, J= =7.51 Hz, ArH [ortho to OH]), 6.78 (s, 1H, ArH [ortho to OH]), 6.74 (d, 1H, J= =8.05 Hz, ArH [para to OH]), 5.90 (br s, 1H, ArOH), 4.17 (q, 2H, J= =7.15 Hz, CO$_2$CH$_2$CH$_3$), 3.57 (s, 2H, CH$_2$CO$_2$CH$_2$CH$_3$), 1.26 (t, 3H, J= =7.14 Hz, CO$_2$CH$_2$CH$_3$).

Step B:

Preparation of ethyl 3-cyclohexylmethyloxy-phenylacetate (29-3)

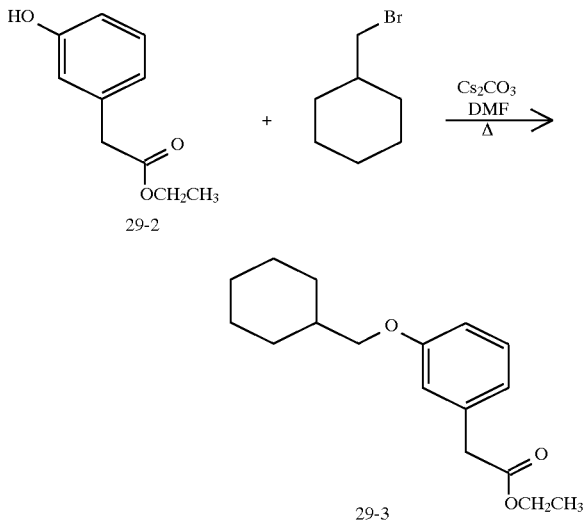

Cyclohexylmethyl bromide (0.459 mL, 3.29 mmol, 1 equiv) was added to a suspension of 29-2 (592 mg, 3.29 mmol, 1 equiv) and cesium carbonate (1.07 g, 3.29 mmol, 1 equiv) in N, N-dimethylformamide (6 mL) at 23° C. The reaction mixture was heated to 70° C. and was stirred at that temperature for 3 h. The solution was cooled to 23° C. and was concentrated. The residue was diluted with ethyl acetate, and the resulting solution was washed with an aqueous saturated ammonium chloride solution (2×20 mL). Organic layer was dried over magnesium sulfate and was concentrated. The resulting oil was purified by flash column chromatography (5% ethyl acetate in hexane) to afford the product as a colorless oil 29-3 as well as recovered ethyl 3-hydroxy-phenylacetate.

$^1$H NMR (400 MHz, CDCl$_3$), δ: 7.21 (t, 1H, J=7.69 Hz, ArH [meta to OCH$_2$Cy]), 6.81 (m, 2H, ArH [ortho and para to OCH$_2$Cy]), 6.83 (s, 1H, ArH [ortho to the OCH$_2$Cy]), 4.15 (q, 2H, J=7.14 Hz, CO$_2$CH$_2$CH$_3$), 3.74 (d, 2H, J=6.40 Hz, OCH$_2$Cy), 3.57 (s, 2H, CH$_2$CO$_2$CH$_2$CH$_3$), 1.86 (d, 2H, J=12.6 Hz, CyH), 1.74 (m, 4H, CyH), 1.24 (m, 3H, CyH), 1.25 (t, 3H, J=7.14 Hz, CO$_2$CH$_2$CH$_3$), 1.05 (m, 2H, CyH); TLC (10% EtOAc-hexane), R$_f$=0.50 (UV)

Step C:

Preparation of 3-cyclohexylmethyloxy-phenylacetic acid (29-4)

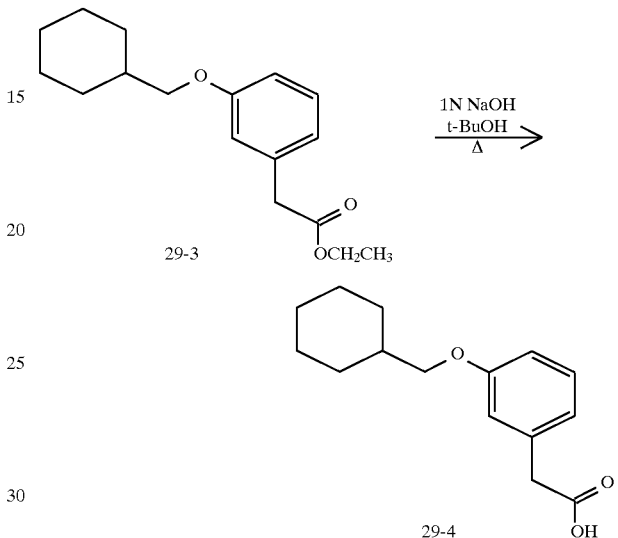

A solution of aqueous sodium hydroxide (1N, 14 mL, 14.0 mmol, 10 equiv) was added to a solution of ethyl 3-cyclohexylmethyloxy-phenylacetate 29-3 (384 mg, 1.39 mmol, 1 equiv) in a mixture of t-butanol (8 mL) and water (4 mL) at 23° C. The reaction mixture was heated at reflux for 2 h. The solution was cooled to 23° C. and was diluted with ethyl acetate (50 mL). The organic layer was washed with an aqueous 10% potassium hydrogen sulfate solution (2×25 mL), then was dried over magnesium sulfate and was concentrated to afford the product 29-4 as a white solid, which was used without further purification.

$^1$H NMR (400 MHz, CD$_3$OD), δ: 7.19 (t, 1H, J=7.88 Hz, ArH [meta to OCH$_2$Cy]), 6.83 (s, 1H, ArH [ortho to OCH$_2$Cy]), 6.79 (m, 2H, ArH [ortho and para to OCH$_2$Cy]), 3.75 (d, 2H, J=6.04 Hz, OCH$_2$Cy), 3.55 (s, 2H, CH$_2$CO$_2$H), 1.87 (d, 2H, J=12.5 Hz, CyH), 1.74 (m, 4H, CyH), 1.29 (m, 3H, CyH), 1.10 (m, 2H, CyH).

Step D:

Preparation of N-4'-pyridyl-(3-cyclohexylmethyloxy) phenylacetamide (29-5)

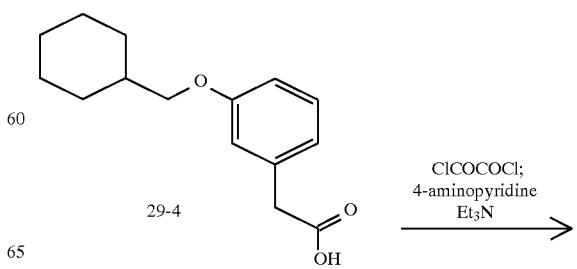

91

-continued

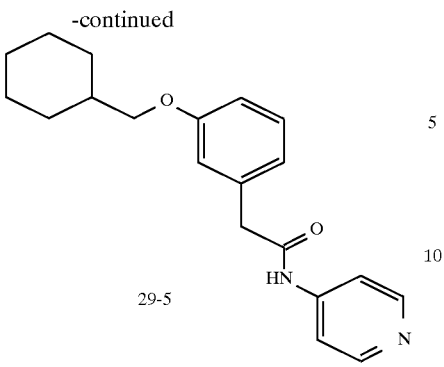

29-5

Oxalyl chloride (0.158 mL, 1.81 mmol, 3 equiv) and a catalytic amount of N, N-dimethylformamide (2 mL) were added consecutively to a solution of 29-4 (150 mg, 0.604 mmol, 1 equiv) in dichloromethane (2 mL) at 23° C. Once gas evolution ceased (approximately 2 min following the addition of the N, N-dimethylformamide), the volatiles were removed in vacuo. The residue was dissolved in dichloromethane (2 mL), and the resulting solution was transferred via cannula to a suspension of 4-aminopyridine (284 mg, 3.02 mmol, 5 equiv) and triethylamine (0.673 mL, 4.83 mmol, 8 equiv) in dichloromethane (2 mL) at 23° C. The reaction mixture was stirred for 2.5 h at 23° C. and then was concentrated in vacuo. The residue was diluted with ethyl acetate (50 mL), and the resulting solution was washed with an aqueous saturated ammonium chloride solution (2×20 mL). The organic layer was dried over magnesium sulfate and was concentrated. The residue was purified by flash column chromatography (100% ethyl acetate) to afford 29-5 as a yellow oil (36 mg, 18.4%).

$^1$H NMR (400 MHz, CDCl$_3$), δ: 8.46 (dd, 2H, J=4.86, 1.56Hz, PyH), 7.36 (dd, 2H, J=4.85, 1.56 Hz, PyH), 7.32 (t, 1H, J=7.88 Hz, ArH [meta to OCH$_2$Cy]), 7.17 (s, 1H, Amide H), 6.88 (m, 2H, ArH [ortho to OCH$_2$Cy]), 6.84 (d, 1H, J=1.83 Hz, ArH [para to OCH$_2$Cy]), 3.76 (d, 2H, J=6.23 Hz, OCH$_2$Cy), 3.72 (s, 2H, CH$_2$-amide), 1.86 (d, 2H, J=13.18 Hz, CyH), 1.76 (m, 4H, CyH), 1.29 (m, 3H, CyH), 1.04 (m, 2H, CyH). TLC (EtOAc), R$_f$=0.20 (UV).

Step E:

Preparation of 4-(2-(3-cyclohexylmethyloxyphenyl)ethyl)aminopyridine (29-6)

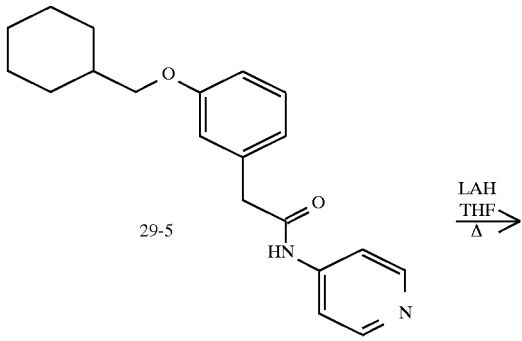

92

-continued

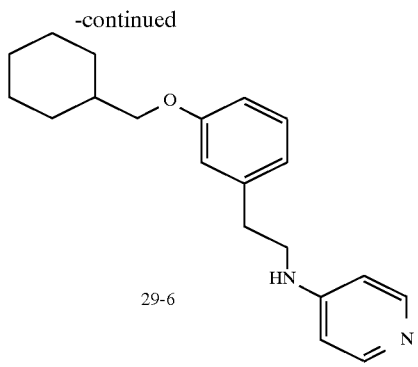

29-6

A solution of lithium aluminum hydride in tetrahydrofuran (1.0M, 0.308 ml, 0.308 mmol, 4 equiv) was added to a solution of 29-5 (25 mg, 0.077 mmol, 1 equiv) in tetrahydrofuran (2 mL) at 0° C. The reaction mixture was heated to 50° C. and was held at that temperature for 2 h. The mixture was cooled to 0° C., and excess lithium aluminum hydride was quenched by the consecutive addition of water (12 μl), aqueous 15% sodium hydroxide solution (12 μl), and water (36 μl). The resulting aluminum salts were removed by filtration. The filtrate was concentrated, and the residue was purified by flash column chromatography (1% methanol in chloroform saturated with ammonia) to afford the product 29-6 as a pale yellow solid (mp:=81°–83° C.).

$^1$H NMR (400 MHz, CDCl$_3$), δ: 8.20 (dd, 2H, J=4.94, 1.47Hz, PyH), 7.23 (t, 1H, J=7.84 Hz, ArH [meta to OCH$_2$Cy]), 6.78 (m, 3H, ArH [ortho and para to OCH$_2$Cy]), 6.43 (dd, 2H, J=4.85, 1.56 Hz, PyH), 4.15 (s, 1H, NH), 3.74 (d, 2H, J=6.22 Hz, OCH$_2$Cy), 3.44 (q, 2H, J=6.87 Hz, CH$_2$NH), 2.89 (t, 2H, J=6.87 Hz, CH$_2$CH$_2$NH), 1.87 (d, 2H, J=13.37 Hz, CyH), 1.77 (m, 4H, CyH), 1.27 (m, 3H, CyH), 1.06 (m, 2H, CyH); TLC (1% MeOH—CHCl$_3$ sat'd with NH$_3$), R$_f$0.27 (UV)

In vitro assay for determining proteinase inhibition

Assays of human a-thrombin and human trypsin were performed at 25° C. in 0.05M TRIS buffer pH 7.4, 0.15M NaCl, 0.1% PEG. Trypsin assays also contained 1 mM CaCl2.

In assays wherein rates of hydrolysis of a p-nitroanilide (pna) substrate were determined, a Thermomax 96-well plate reader was used to measure (at 405 nm) the time dependent appearance of p-nitroaniline. sar-PR-pna (sarcosine-Pro-Arg-p-nitroanilide) was used to assay human a-thrombin (K$_m$=125 μM) and human trypsin (K$_m$=59 μM). p-Nitroanilide substrate concentration was determined from measurements of absorbance at 342 nm using an extinction coefficient of 8270 cm$^{-1}$M$^{-1}$.

In certain studies with potent inhibitors (Ki<10 nM) where the degree of inhibition of thrombin was high, a more sensitive activity assay was employed. In this assay the rate of thrombin catalyzed hydrolysis of the fluorogenic substrate Z-GPR-afc (Cbz-Gly-Pro-Arg-7-amino-4-trifluoromethyl coumarin) (Km=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethylcoumarin produced upon complete hydrolysis of an aliquot of the stock solution by thrombin.

Activity assays were performed by diluting a stock solution of substrate at least tenfold to a final concentration 0.5 K$_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, $[I]/e$, and $[I]/e$ (where $[S]$, $[I]$, and e respectively represent the total concentrations, of substrate, inhibitor and enzyme), the equilibrium constant ($K_i$) for dissociation of the inhibitor from the enzyme can be obtained from the dependence of $V_o/V_i$ on $[I]$ shown in equation 1.

$$V_o/V_i = 1 + [I]/K_i \qquad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

Thrombin Inhibitors—Therapeutic Uses

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prothesis, cardiac prosthesis, and extracorporeal circulation systems.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Coming Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.1 mg per kg of body weight per day (mg/kg/day) to about 100 mg/kg/day and preferably 1.0–100 mg/kg/day and most preferably 1–20 mg/kg/day. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

For example, oral tablets can be prepared which contain an amount of active compound of between 100 and 500 mg, typically between 200 and 250 mg. Typically, a patient in need of thrombin inhibitor compound, depending on weight and metabolism of the patient, would be administered between about 100 and 1000 mg active compound per day. For a patient requiring 1000 mg per day, two tablets containing 250 mg of active compound can be administered in the morning and two tablets containing 250 mg of active compound can again be administered in the evening. For a patient requiring 500 mg per day, one tablet containing 250 mg of active compound can be administered in the morning and one tablet containing 250 mg of active compound can again be administered in the evening.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anti-coagulation agents or thrombolytic agents such as plasminogen activators or streptokinase to achieve synergistic effects in the treatment of various ascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfarin.

EXAMPLE 10

Tablet Preparation

Tablets containing 25.0, 50.0, and 100.0 mg., respectively, of the following active compound is prepared as illustrated below:

4-amino-1-(4-(1,1-diphenylmethoxy)benzylpyridinium bromide

TABLE FOR DOSES CONTAINING FROM
25–100 MG OF THE ACTIVE COMPOUND

|  | Amount-mg | | |
|---|---|---|---|
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

What is claimed is:

1. A compounds having the following structure:

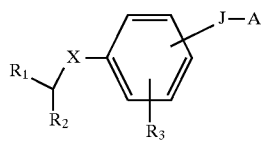

I or a pharmaceutically acceptable salts thereof wherein
X is
—N($R^4$)—,
—O—,
—S—,
—$SO_2$—,
—SO—,
—$OCH_2(CH_2)_n$ aryl-, or
—$OCH_2(CH_2)_n$ $C_{3-8}$cycloalkyl-,
wherein n is 1 or 2;
J is
—$(CH_2)_m$NH—,
—$SO_2$NH—,
—$SO_2(CH_2)_m$—,
—$NHSO_2$—,
—$SO_2$—, or
—$(CH_2)_mSO_2$—,
wherein m is 1 or 2;
$R^1$, $R^2$, and $R^4$ are independently selected from
hydrogen,
aryl,
aryl $C_{1-4}$ alkyl,
diaryl $C_{1-4}$ alkyl,
dicyclo $C_{3-8}$ alkyl $C_{1-4}$ alkyl,
cyclo $C_{3-8}$ alkyl $C_{1-4}$ alkyl,

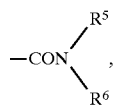

wherein $R^5$ and $R^6$ are independently hydrogen or $C_{1-4}$ alkyl,
substituted aryl with one or two substituents selected from
$C_{1-4}$ alkyl,
$C_{1-4}$ alkoxy,

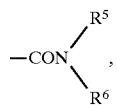

wherein $R^5$ and $R^6$ are independently hydrogen or $C_{1-4}$ alkyl,
aryloxy,
cyclo $C_{3-8}$ alkoxy,
methylenedioxy,
halogen, or
hydroxy,
heteroaryl with one or two heteroatoms selected from N, O, and S,
cyclo $C_{3-7}$ alkyl unsubstituted or substituted with one or
more of $C_{1-4}$ alkyl, $C_{1-4}$ alkoxy, benzyl, cyclohexylmethyl or aryl,
a $C_{4-10}$ carbocyclic or bicyclic ring, or
$R^1$ and $R^2$ along with the carbon to which they attach form a cyclo $C_{3-7}$ alkyl ring;
$R^3$ is
hydrogen,
$C_{1-4}$ alkyl,
$C_{1-4}$ alkenyl,
$C_{1-4}$ alkoxy,
—$NHR^7$ wherein $R^7$ is hydrogen or $C_{1-4}$ alkyl, or
—$NHSO_2CH_2$aryl;

A is selected from one of the following fragments

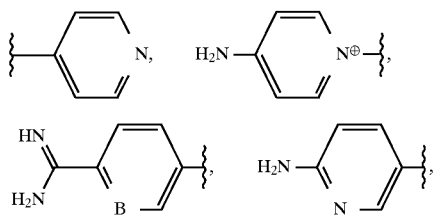

2. A compound of claim 1 having the following structure:

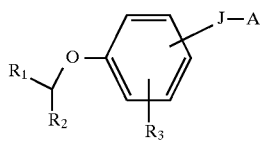

or a pharmaceutically acceptable salts thereof wherein

J is $(CH_2)_mNH$, or $SO_2$, where m is 1 or 2;

$R^1$ and $R^2$ are independently selected from
  hydrogen,
  aryl, or
  cyclo $C_{3-7}$ alkyl unsubstituted or substituted with one or more of $C_{1-4}$ alkyl, $C_{1-4}$ alkoxy, benzyl, cyclohexylmethyl or aryl;

$R^3$ is
  hydrogen,
  $C_{1-4}$ alkyl, or
  $C_{1-4}$ alkenyl;

A is selected from one of the following fragments

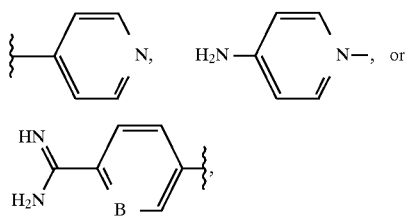

wherein B is N or.

3. A compound of claim 2 having the following structure:

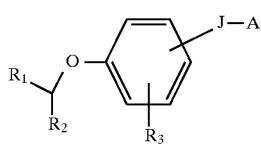

or a pharmaceutically acceptable salts thereof wherein

J is $CH_2NH$, or $SO_2$;

$R^1$ and $R^2$ are independently selected from
  hydrogen,
  aryl, or
  cyclohexyl;

$R^3$ is
  hydrogen,
  —CH=$CH_2$, or
  —$CH_2CH_3$; and

A is

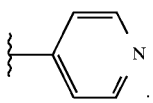

4. A compound of claim 3 which has the structure:

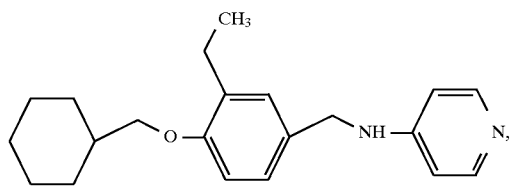

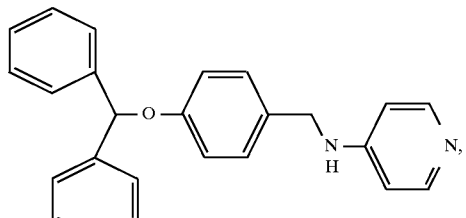

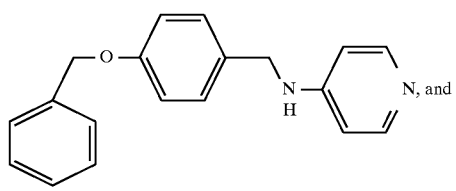

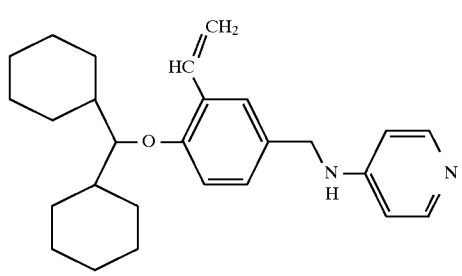

or a pharmaceutically acceptable salts thereof.

5. A composition comprising a therapeutically effective amount of a compound of claim 1 and a pharmaceutically acceptable carrier.

6. A method for inhibiting thrombin in blood in a mammal comprising administering to the mammal in need thereof a thrombin inhibiting amount of a composition of claim 5.

7. A method for inhibiting formation of blood platelet aggregates in blood in a mammal in need thereof a platelet aggregation inhibiting amount of comprising administering to the mammal a composition of claim 5.

8. A method for inhibiting formation of fibrin in blood in a mammal comprising administering to the mammal in need thereof a fibrin formation inhibiting amount of a composition of claim 5.

9. A method for inhibiting thrombus formation in blood in a mammal comprising administering to the mammal in need thereof a thrombus formation inhibiting amount of a composition of claim 5.

10. A method for inhibiting thrombin in stored blood comprising administering to said blood a thrombin inhibiting amount of a composition of claim 5.

11. A method for inhibiting formation of blood platelet aggregates in stored blood comprising administering to said blood a platelet aggregation inhibiting amount of a composition of claim 5.

12. A method for inhibiting formation of fibrin in stored blood comprising administering to said blood a fibrin formation inhibiting amount of a composition of claim 5.

13. A method for inhibiting thrombus formation in stored blood comprising administering to said blood a thrombus inhibiting amount of a composition of claim 5.

* * * * *